US005741926A

United States Patent [19]
Bierer et al.

[11] Patent Number: 5,741,926
[45] Date of Patent: Apr. 21, 1998

[54] ANILINE DERIVATIVES HAVING ANTIHYPERGLYCEMIC ACTIVITY

[75] Inventors: Donald E. Bierer, Daly City; Larisa G. Dubenko, San Francisco, both of Calif.

[73] Assignee: Shaman Pharmaceuticals, Inc., South San Francisco, Calif.

[21] Appl. No.: 799,745

[22] Filed: Feb. 12, 1997

[51] Int. Cl.$^6$ ................................................. C27C 229/00
[52] U.S. Cl. ........................... 562/457; 562/458; 514/563
[58] Field of Search .................................. 562/457, 458; 514/763

[56] References Cited

U.S. PATENT DOCUMENTS

| | | |
|---|---|---|
| 3,374,264 | 3/1968 | Uskovic et al. . |
| 4,113,871 | 9/1978 | Stach et al. . |
| 4,182,776 | 1/1980 | Albright et al. . |
| 4,238,506 | 12/1980 | Stach et al. . |
| 4,260,816 | 4/1981 | Albright et al. . |
| 4,271,188 | 6/1981 | Hindley . |
| 4,307,113 | 12/1981 | Anderson . |
| 4,440,940 | 4/1984 | Shepherd . |
| 4,810,716 | 3/1989 | Conner et al. . |
| 4,826,850 | 5/1989 | Yamato . |
| 5,153,226 | 10/1992 | Chucholowski et al. . |

FOREIGN PATENT DOCUMENTS

| | | |
|---|---|---|
| 0 023 569 A1 | 11/1981 | European Pat. Off. . |
| 0 138 407 A1 | 4/1985 | European Pat. Off. . |
| 0 394 440 B1 | 5/1990 | European Pat. Off. . |
| 0 376 166 A1 | 7/1991 | European Pat. Off. . |
| 2928352 A1 | 1/1981 | Germany . |
| 3332633 A1 | 9/1983 | Germany . |
| 664864 | 8/1952 | South Africa . |
| 1 153 884 | 5/1969 | United Kingdom . |
| 1 484 848 | 9/1977 | United Kingdom . |
| 2 019 214 A | 4/1978 | United Kingdom . |
| 1 533 647 | 11/1978 | United Kingdom . |
| 2 062 621 A | 5/1981 | United Kingdom . |
| 2 062 622 A | 5/1981 | United Kingdom . |
| WO91/11997 | 8/1991 | WIPO . |

OTHER PUBLICATIONS

Asakawa et al., "Chemistry Of Salicyclic Acid And Anthranilic Acid III. Hypoglycemic Screen Tests For Salicyclic And Anthranilic Acid Derivatives", Chem. Pharm. Bull. 27(6):1468–1472 (1979).

Bever et al., "Plants With Oral Hypoglycaemic Action", Quart J. Crude Drug Res. 17(3–4):139–196 (1979).

Blackshear et al., "Metabolic Interactions Of Dichloroacetate And Insulin In Experimental Diabetic Ketoacidosis", Biochem. J. 145:447–456 (1975).

Blank et al., "Mercapto Heterocyclic Carboxylic Acids, Analogues Of 3–Mercaptopicolinic Acid", J. –Med. Chem. 20(4):572–576 1977.

Blank et al., "Mercaptopyridinecarboxylic Acids, Synthesis And Hypoglycemic Activity", J. Med Chem. 17(10):1065–1071 (1974).

Chang et al., "Synthesis Of 7–Substituted Indolo[3,2–b]–Quinoline Derivatives", Heterocycles 33(1):147–152 (1992).

Chen et al., "3–Aminopicolinate Inhibits Phosphoenolpyruvate Carboxykinase In Hepatocytes And Increase Release Of Gluconeogenic Precursors From Peripheral Tissues", J. Biol. Chem. 259:6920–6924 (1984).

DiTullio et al., "3–Mercaptopicolonic Acid, An Inhibitor Of Gluconeogenesis", Biochem. J. 138:387–394 (1974).

Frost et al., "Evidence For The Involvement Of Vicinal Sulfhydryl Groups In Insulin–Activated Hexose Transport By 3T3–L1 Adipocytes", J. Biol. Chem. 260:2646–2652 (1985).

Görlitzer et al. Pharmazie 49:231–235 (1994).

Görlitzer et al., Arch. Pharm. 314:852–861 (1981).

Grote et al., "Stereocontrolled Synthesis of DPTA Analogues Branched In The Ethylene Unit", J. Org. Chem. 60:6987–6997 (1995).

Hipskind et al., "Practical And Enantiospecific Synthesis of LY303870, A Novel NK–1 Antagonist", J. Org. Chem. 60:7033–7036 (1995).

Jörgensen et al., "Neurohypophysis And Water Metabolism In The Toad, Bufo Bufo (L)", Endicrinology 59(6):601, 715–718 (1956).

Marles et al. "Antidiabetic Plants And their Active Constituents", Phytomedicine 2(2):137–189 (1995).

Ossman et al., "Synthesis Of 2–Cyanomethyl–3, Benzoxazine–4 (H)–One", Egypt J. Chem 31(3):381–385 (1988).

Sandhu et al., "Triorganotin Derivatives Of 1,2-Bis(2'–Carboxyphenylamino) Ethane And –Propane, And Ethylenediaminetetraacetic Acid", J. Organomettallic Chemistry 315:309–319 (1986).

Snell, "Hypoglycaemia Caused By Indole And Quinoline Derivatives", pp. 745–748, Non–Hormonal Hypoglycaemic Compounds–Colloquium Organized On Behalf Of The Pharmacological Biochemistry Group By J.W. Bridges, 579th Meeting, London, Nov. 8–10, 1978.

Sunder et al., "Synthesis of Benzofurol[3.2–b] Quinoline–6(11H)One And Derivatives", J. Heterocyclic Chem. 15:1379–1382 (1978).

Takeuchi et al., "Synthesis And Antitumor Activity Of 7–(N–Glycosylamino)–Indolo[3,2–b] Quinolines", Chem. Pharm. Bull. 39(6):1629–1631 (1991).

Takechi et al., "Synthesis And Antitumor Activity Of Fused Quinoline Derivatives III.$^{1,2)}$ Novel N–Glycosylamino–Indolo[3,2–b] Quinoline", Chem. Pharm. Bull. 40(6):1481–1485 (1992).

(List continued on next page.)

Primary Examiner—Paul J. Killos
Attorney, Agent, or Firm—Pennie & Edmonds

[57] ABSTRACT

Aniline derivatives useful as antihyperglycemic agents, pharmaceutical compositions comprising the aniline derivatives and methods for their use are described. The aniline derivatives are useful for the treatment of insulin-dependent diabetes mellitus (IDDM or Type I) and non-insulin dependent diabetes mellitus (NIDDM or Type II).

4 Claims, 4 Drawing Sheets

OTHER PUBLICATIONS

Yamato et al., "Synthesis And Antitumor Activity Of Fused Tetracylclic Quinoline Derivatives. 1", J. Med. Chem. 32:1295–1300 (1989).

Yamato et al., "Synthesis And Antitumor Activity Of Fused Quinoline Derivatives", chem.Pharm. Bull. 38(11):3048–3052 (1990).

Yamato et al., "Synthesis And Antitumor Activity Of Fused Quinoline Derivatives . II.[1] Novel 4–and 7–Hydroxyyndolo–[3,2–b] Quinolines", Chem. Pharm. Bull. 40(2):528–530 (1992).

El–Kerdawy et al., "Synthesis and Some Spectral Identification of Certain Triazoles and Benzotriazoles," J. Pharm. Belg. 36(2):103–8 (1981) (Abstract, Chemical Abstracts No. 95:169081z).

K. Goerlitzer, "1,3–Dicarbonyl Compounds. 3. β–Ketoesters," Arch. Pharm. 308(4):272–86 (1975) (Abstract, Chemical Abstracts No. 83:79112h).

U.H. Pandya et al., "Studies on Amides." J. Inst. Chem. (India) 53(2):67–8 (1981) (Abstract, Chemical Abstracts No. 95:132436t).

V.H. Shah et al., "Studies on Acetamide Derivatives. Part–II. Preparation, Antimicrobial and antithelmintic activity of N–arylaminoacetylbenzimidazole/sulfadiazine or sulfamethazine and N–arylbenzimidazol–1–yl/sulfadiazin–4–yl or sulfamethazin–4–yl/acetamides," J. Indian Chem. Soc. 64(11):678–81 (1987) (Abstract, Chemical Abstracts 109:210992v).

ANILINE DERIVATIVES HAVING ANTIHYPERGLYCEMIC ACTIVITY

TABLE OF CONTENTS

1. FIELD OF THE INVENTION
2. BACKGROUND OF THE INVENTION
3. SUMMARY OF THE INVENTION
4. DESCRIPTION OF THE FIGURES
5. DETAILED DESCRIPTION OF THE INVENTION
   5.1 ANILINE DERIVATIVES AND THEIR SYNTHESIS
   5.2 METHODS AND COMPOSITIONS FOR USE OF ANILINE DERIVATIVES
6. EXAMPLES: SYNTHESIS OF ANILINE DERIVATIVES
   6.1 MATERIALS AND METHODS
   6.2 ANILINE DERIVATIVES SYNTHESIZED
7. EXAMPLE: ANTIHYPERGLYCEMIC ACTIVITY
   7.1 IN VIVO ACTIVITY OF THE ANILINE DERIVATIVES
      7.1.1 PROTOCOLS
      7.1.2 RESULTS
   7.2 IN VITRO ACTIVITY OF THE ANILINE DERIVATIVES
      7.2.1 PROTOCOLS
         7.2.1.1 METHOD A: CELL CULTURE AND 2-DEOXY-D-GLUCOSE UPTAKE IN IN DIFFERENTIATED 3T3-L1 ADIPOCYTES WITHOUT EXOGENOUSLY ADDED INSULIN
         7.2.1.2 METHOD B: CELL CULTURE AND 2-DEOXY-D-GLUCOSE UPTAKE IN DIFFERENTIATED 3T3-L1 ADIPOCYTES WITH EXOGENOUSLY ADDED INSULIN
      7.2.2 RESULTS USING METHOD A
      7.2.3 RESULTS USING METHOD B

The present invention claims priority benefits of copending U.S. patent application Ser. No. 08/600,725, filed Feb. 13, 1996, which is incorporated by reference herein in its entirety.

1. FIELD OF THE INVENTION

This invention pertains to a novel group of aniline derivatives that are useful as antihyperglycemic agents and useful for the treatment of diabetes mellitus, pharmaceutical compositions comprising the aniline derivatives and methods of using the same.

2. BACKGROUND OF THE INVENTION

Various chemical compounds have been known to exhibit antihyperglycemic activity.

ZA Patent 664864 discloses that compounds of formula (A):

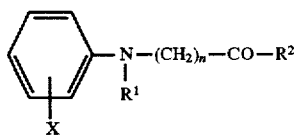

wherein X is a hydrogen or halogen atom, or a straight or branched alkyl group having from 1 to 4 carbon atoms; $R^1$ is a hydrogen atom or a straight or branched alkyl group having from 1 to 4 carbon atoms; $R^2$ is an hydroxy, amino, hydrazino or alkoxy group, where alkoxy has from 1 to 4 carbon atoms; and n is 1 or 2, have antihyperglycemic activity.

U.K. Patent 1,153,884 discloses that the administration to mammals of N-phenylglycine compounds, including N-o-fluorophenylglycine, results in antihyperglycemia.

In addition, plant growth regulators such as indole-3-acetic acid and L- tryptophan, and natural and synthetic analogues such as anthranilic acid, nicotinic acid, and 4-chlorophenoxyacetic acid have been shown to inhibit insulinase in vitro, potentiate the effect of insulin in vitro, and to act as hypoglycemic agents in vivo in normal rats ((1) Oliver-Bever, B.; Zahnd, G. R. *Quart. J. Crude Drug Res.* 1979, 17, 139–196; (2) Mirsky, J. A.; Diengott, D.; Perisutti, G. *Endocrinology* 1956, 59, 715–718; (3) Marles, R. J.; Farnsworth, N. J. *Phytomedicine* 1995, 2, 137–189). 3-Aminopicolinate, 3-mercaptopicolinic acid and related analogues have also been reported to possess hypoglycemic activity ((1) Blank, B.; DiTullio, N. W.; Miao, C. K., Owings, F. F.; Gleason, J. G.; Ross, S. T.; Berkoff, C. E.; Saunders, H. L.; Delarge, J.; Lapiere, C. L. *J. Med. Chem.*, 1974, 17, 1065–1071; (2) DiTullio, N. W.; Berkoff, C. E.; Blank, B.; Kostos, V.; Stack, E. J.; Saunders, H. L. *Biochem. J.* 1974, 138, 387–394; (3) Blackshear, P. J., Holloway, P. A. H.; Alberti, K. G. M. N. *Biochem. J.* 1975, 447–456; (4) Blank, B.; DiTullio, N. W.; Owings, F. F.; Deviney, L; Miao, C. K.; Saunders, H. L. *J. Med. Chem.* 1977, 20, 572–576) through the inhibition of gluconeogenesis (Chen, K. S.; Lardy, H. A. *J. Biol. Chem.*, 1984, 259, 6920–6924).

WO 91/11997 discloses that hydroxy- or nitro-substituted aminobenzoic acids are useful for treating or preventing various complications of diabetes.

U.S. Pat. No. 4,307,113 discloses that anthranilic acid derivatives of Formula (C)

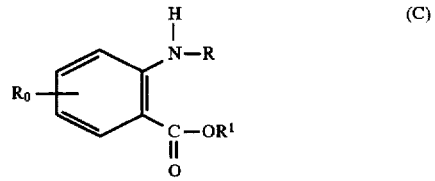

wherein
$R_o$ is fluorine, chlorine, bromine, nitro or trifluoromethyl;
R is hydrogen, $C_{1-6}$ alkyl or $C_{2-4}$ alkanoyl; and
$R_1$ is hydrogen or $C_{1-6}$ alkyl, possess antidiabetic activity.
See also U.K. Patent Application GB2019214A.

U.S. Pat. No. 4,113,871 discloses that phenyl-alkane carboxylic acids of Formula (E):

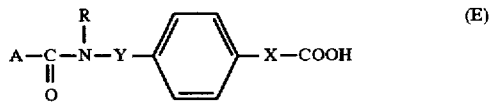

wherein
A is an aryl, aralkyl or arylvinyl radical optionally substituted by hydroxy, halogen, trifluromethyl, alkyl, alkylthio, alkoxy, alkenyloxy, alkoxyalkoxy, alkyl-substituted amino, aryloxy or alkoxy-substituted aryloxy, or is an aryloxyalkyl or arylthioalkyl radical or a heterocyclic ring system optionally substituted by halogen, alkyl or alkoxy;

Y is a valency bond or an unbranched or branched lower alkylene radical containing up to 3 carbon atoms, X is a straight or branched, saturated or unsaturated divalent aliphatic hydrocarbon radical containing 2 to 8 carbon atoms, there being at least 2 carbon atoms between the benzene ring and the carboxyl group; and R is a hydrogen atom or a lower alkyl radical; and the physiologically compatible salts, esters and amides thereof, have hypoglycemic properties. Also see GB 1484848.

UK patent application GB 2090834A describes amides according to the general formula (F):

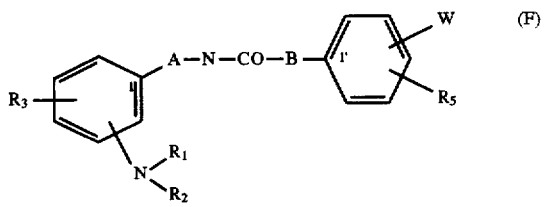

wherein $R_1$ and $R_2$, which may be the same or different, each represents an alkyl group containing 1 to 6 carbon atoms or a cycloalkyl group containing 6 to 7 carbon atoms, or $R_1$ and $R_2$ together with the nitrogen atom to which they are attached represent an unbranched alkyleneimino group containing 3 to 6 carbon atoms optionally substituted by 1 or 2 alkyl groups, each containing 1 to 3 carbon atoms, or by a hydroxy group and in which a methylene group may optionally be replaced by a carbonyl group, by an oxygen or sulfur atom or by an imino group (which may optionally be substituted by an alkyl group containing 1 to 3 carbon atoms, an aralkyl group containing 7 to 10 carbon atoms or by a phenyl or halophenyl group) or an ethylene group may optionally be replaced by an O-phenylene group; and unbranched alkenyleneimino group containing 4 to 6 carbon atoms; a saturated or partly unsaturated azabicycloalkyl group containing 6 to 10 carbon atoms; an aza-1,4-dioxaspiro-alkyl group containing 6 to 8 carbon atoms; or a heptamethyleneimino, octamethyleneimino, nonamethyleneimino or decamethyleneimino group;

$R_3$ represents a hydrogen or halogen atom, a trifluoromethyl, alkyl, hydroxy, alkoxy, alkanoyloxy, mercapto, alkylmercapto, nitro, amino, cyano, alkanoyl, carboxy, alkoxycarbonyl, aminocarbonyl, alkylaminocarbonyl, dialkylaminocarbonyl, aminosulfonyl, alkylamino, dialkylamino, alkanoylamino, alkoxycarbonylamino or alkylsulfonylamino group (wherein each alkyl part in the above mentioned groups may contain from 1 to 3 carbon atoms), an aralkoxy group containing 7 to 10 carbon atoms or an arylcarbonylamino group;

$R_4$ represents a hydrogen atom or an alkyl group containing 1 to 3 carbon atoms;

$R_5$ represents a hydrogen atom, a halogen atom or an alkyl group containing 1 to 3 carbon atoms;

A represents a bond, a methylene or ethylene group optionally substituted by an alkyl group containing 1 to 5 carbon atoms, a methylene or ethylene group substituted by two alkyl groups each containing 1 to 3 carbon atoms, a methylene group substituted by a cycloalkyl group containing 3 to 7 carbon atoms or by a hydroxyalkyl, alkoxyalkyl, cyano, carboxyl, alkoxycarbonyl, aminocarbonyl, alkylaminocarbonyl, dialkylaminocarbonyl, aryl or aralkyl group, wherein each of the alkyl parts may contain from 1 to 3 carbon atoms, a cycloalkylidene group containing 3 to 7 carbon atoms or a vinylidene group of formula

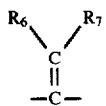

wherein $R_6$ and $R_7$, which may be the same or different, each represents a hydrogen atom or an alkyl group containing 1 to 3 carbon atoms or one of the radicals $R_6$ and $R_7$ represents a cycloalkyl group containing 3 to 7 carbon atoms or an aryl or aralkyl group and the other is as defined above or $R_6$ and $R_7$ together with the carbon atom to which they are attached, represent a cycloalkylidene radical containing 5 to 7 carbon atoms;

B represents a methylene or ethylene group optionally substituted by an alkyl group containing 1 to 3 carbon atoms and W represents a hydrogen or halogen atom, a nitro group, an amino group (optionally substituted by an alkanoyl group containing 1 to 3 carbon atoms) an alkyl group containing 1 to 3 carbon atoms (optionally substituted by a hydroxy or carboxy group or by one or two alkoxycarbonyl groups containing 2 to 4 carbon atoms each), an alkenyl group containing 2 to 5 carbon atoms substituted by a carboxy or alkoxycarbonyl group containing 2 to 4 carbon atoms, an alkanoyl group containing 1 to 3 carbon atoms, a dialkoxymethyl or trialkoxymethyl group containing 1 to 3 carbon atoms in each alkyl part, an alkylenedioxymethyl group containing 2 or 3 carbon atoms in the alkylene part, a 1,3-oxazoline-2-yl or cyano group, an aminocarbonyl group (optionally substituted by one or two alkyl groups containing 1 to 4 carbon atoms in each alkyl part), an unbranched alkyleneiminocarbonyl group containing 5 to 8 carbon atoms, a morpholinocarbonyl group, a (dialkyldioxolane-yl)alkoxy-carbonyl group containing 7 to 10 carbon atoms or a carboxy group or esterfied carboxy group wherein if the said ester group consists of an alkyl group containing 1 to 6 carbon atoms this may be substituted, in any but the α-position, by a hydroxy, alkoxy, amino, alkylamino, dialkylamino, 1,3-dimethylxanthine-7-yl, alkanoyloxy, aroyloxy, aralkanoyloxy or pyridine-carbonyloxy group or by two hydroxy groups—except in the case of any methyl or methylene group in the above cases, which can only be substituted by one hydroxy group or by a group of formula

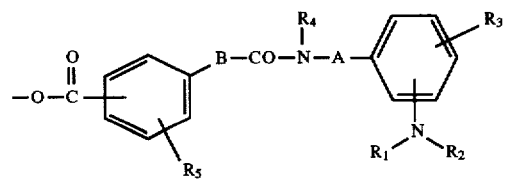

wherein A, B, $R_1$, $R_2$, $R_3$, $R_4$ and $R_5$, are as hereinbefore defined whereby each alkyl part of the above alkyl ester substituents may contain from 1 to 3 carbon atoms), as useful agents for lowering blood glucose.

BE Patent 890 948 discloses that anthranilic acid derivatives of general formula (G)

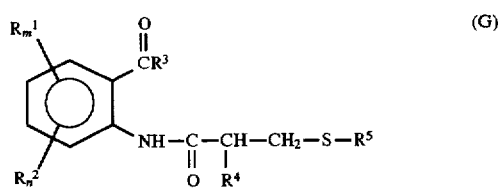

wherein $R^1$ and $R^2$ independently represent one or the other of a hydrogen, a halogen, a small alkyl radical, a nitro radical, the radical $—OR^6$, the radical R—

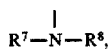

a small alkanoyloxy radical or a trifluoromethyl radical;

R³ represents the radical OR⁶ or the radical R⁷—

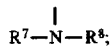

R⁴ represents a hydrogen atom, a halogen atom, a trifluoromethyl radical, a small alkyl radical, a cycloalkyl radical, a bridged cycloalkyl radical, an aryl radical, or a small aryl radical;

R⁵ represents a hydrogen atom, a small alkyl radical, a cycloalkyl radical, a bridged cycloalkyl radical, an aryl radical, a small arylalkyl radical, a small alkanoyl radical, or the radical R⁹;

m and n represent 1, 2, or 3, or less than or equal to 4;

R⁶, R⁷, and R⁸ represent independently one or the other of a hydrogen atom, a small alkyl radical, a cycloalkyl radical, a bridged cycloalkyl radical, an aryl radical, or a small arylalkyl radical; and R⁹ represents the formula

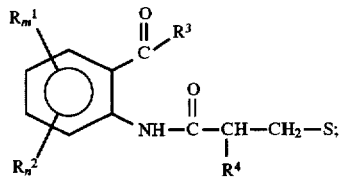

are useful as antidiabetic and antilipidemic agents.

Asakawa et al. (Asakawa, H.; Imamiya, E.; Hamura, Y. *Chem. Pharm. Bull.* 1979, 27, 1468–1472) discloses that anthranilic acid derivatives of the general formula (H)

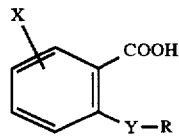

wherein:

X is halogen of hydrogen;

Y is NH; and

R is benzyl, substituted benzyl, benzoyl, heteroaroyl, arylalkyl, or heteroarylalkyl are hypoglycemic agents.

EP Patent Application 023 569A1 discloses that anthranilic acid derivatives of the general formula (D)

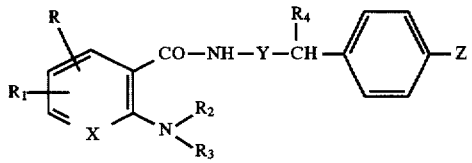

wherein:

R is hydrogen, halogen, dialkylamino or a hexamethyleneimino group;

R₁ is hydrogen, halogen, alkyl or branched alkyl groups, alkoxy groups, arylalkoxy groups, nitro, cyano, amino, alkanoylamino, carboxy, alkoxycarbonyl groups, or dialkylamido sulfonyl groups;

R₂ and R₃ are branched or nonbranched alkyl groups of 3–7 carbon atoms, alkyl groups from 1 to 7 carbon atoms, alkenyl groups with 3–7 carbon atoms, cycloalkyl groups with 3–7 carbon atoms, a phenylalkyl group, phenyl, or adamantyl; or R₂ and R₃ can be part of a ring or substituted ring;

R₄ is hydrogen or an alkyl group with 1–3 carbon atoms;

X can be a nitrogen or CH group;

Y is an oxygen atom, an imino group, an alkylimino group, or a dialkylimino group, methylene, or a substituted methylene group;

Z is hydrogen, halogen, nitro, amino, cyano, formyl, hydroxymethyl or a hydroxymethylene group, carboxy, alkoxylcarbonyl, or alkyl groups; and R₅ is halogen, amino, cyano, hydroxy, alkoxy groups, or arylalkoxy groups; are useful agents for lowering blood sugar levels.

Also described in EP 023569AI are compounds of the general formula (J)

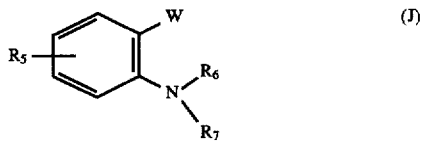

wherein:

R₅ is halogen, amino, cyano, hydroxy, arylalkoxy group containing 1–3 carbons, or alkoxy groups with 4–6 carbon atoms;

R₆ and R₇ in combination with a nitrogen atom make a heterocyclic ring or a substituted heterocyclic ring; and W is carboxy, aminocarboxyl, cyano, or an alkoxycarbonyl group which has 2–4 atoms;

which are purported to be useful agents for lowering blood sugar levels.

DE Patent 2928352 discloses that aminobenzoic acid amides of the general formula (K)

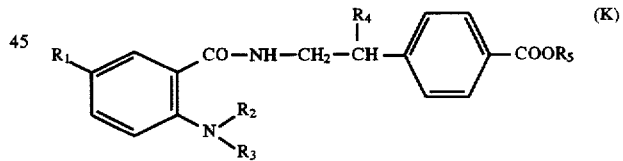

wherein:

R₁ is hydrogen, halogen, nitro, amino, alkanoylamino, alkoxy, cyano, carboxyl, alkoxycarbonyl, or dialkylaminosulfonyl groups in which the carbon part can contain 1–3 carbon atoms;

R₂ and R₃ can be branched or nonbranched alkyl groups with 1–7 carbon atoms, or cycloalkyl groups with 3–7 carbon atoms; or R₂ and R₃ can be part of a 3–7 membered substituted or unsubstituted ring;

R₄ is hydrogen or an alkyl group with 1–4 carbons;

R₅ is a hydrogen, or an alkyl group with 1–4 carbons; and pharmaceutically acceptable salts;

are useful as blood sugar lowering agents.

DE Patent 3332633 discloses that substituted carbon acid derivatives of the general formula (L)

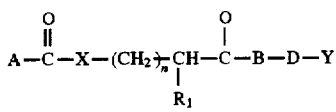

wherein, inter alia, X can be a substituted amino group, possess antidiabetic activity.

The following compounds have not been shown to have antihyperglycemic activity:

2-(2-((Phenylamino)acetyl)amino)benzoic acids have been used as synthetic intermediates for the preparation of indolo-(3,2-b)quinoline-11-ones (quindolones) and indolo-(3,2-b)quinolines (quindolines). The parent 2-(2-((phenylamino)acetyl)amino)benzoic acid was used to prepare 11-chloroquindoline ((1) Yamato, M.; Takeuchi, Y.; Chang, M-r.; Hashigaki, K.; Tsuruo, T.; Tashiro, T.; Tsukagoshi, S. Chem. Pharm. Bull. 1990, 38, 3048–3052; (2) Gorlitzer, K.; Weber, J. Arch. Pharm. (Weinheim) 1981, 314, 852–861). 3-Methoxy-2-(2-((phenylamino)acetyl)amino)benzoic acid has been used to prepare 4-methoxy-11-choroquindoline and 4-hydroxy-11-choroquindoline ((1) Yamato, M.; Takeuchi, Y.; Chang, M-r.; Hashigaki, K. Chem. Pharm. Bull. 1992, 40, 528–530; (2) JP 5-306284); 2-(2-((N-(4-methoxyphenyl)-N-(benzyl)amino)acetyl) amino)benzoic acid and 2-(2-(((4-methoxyphenyl) amino)acetyl)amino)benzoic acid have been reported in the successful and unsuccessful synthesis, respectively, of 7-methoxy-11-chloroquindoline ((1) Yamato, M.; Takeuchi, Y.; Chang, M-r.; Hashigaki, K. Chem. Pharm. Bull. 1992, 40, 528–530; (2) JP 5-306284); 2-(2-(((4-methylphenyl)amino)acetyl) amino)benzoic acid, 2-(2-(((4-chlorophenyl)amino) acetyl)amino)benzoic acid, and 2-(2-(((4-fluorophenyl) amino)acetyl)amino)benzoic acid have been used in the synthesis of 7-methyl-11-chloroquindoline, 7-chloro-11-chloroquindoline, and 7-fluoro-11-chloroquindoline, respectively ((1) Chang, M-r.; Takeuchi, Y.; Hashigaki, K.; Yamato, M. Heterocycles 1992, 33, 147–152; (2) Gorlitzer, K.; Stockmann, R.; Walter, R. D. Pharmazie 1994, 49, 231–235); 2-(2-((3-((p-toluenesulfonyl)amino)phenyl)amino)acetyl) amino)benzoic acid was used to prepare 8-amino-11-bromoquindoline (Takeuchi, Y.; Chang, M-r.; Hashigaki, K.; Tashiro, T.; Tsuruo, T.; Tsukagoshi, S.; Yamato, M. Chem. Pharm. Bull. 1992, 40, 1481–1485); 2-(2-((phenoxy)acetyl)amino)benzoic acid (Baker, B. R.; Hurlbut, J. A. J. Med. Chem. 1968, 11, 1054) has been used in the synthesis of 11-chloro-benzofuro(3,2-b)quinoline ((1) Yamato, M. U.S. Pat. No. 4,826,850; (2) Sunder, S.; Peet, N. P. J. Heterocyclic Chem. 1978, 15, 1379 (3) Yamato, M.; Takeuchi, Y.; Hashigaki, K.; Ikeda, Y.; Chang, M.-r.; Takeuchi, K.; Matsushima, M.; Tsuruo, T.; Tashiro, T.; Tsukagoshi, S.; Yamashita, Y.; Nakano, H. J. Med. Chem. 1989, 32, 1295–1300), and has been used by Gorlitzer as an intermediate in the synthesis of 11-oxo-5,11-dihydrobenzofuro(3,2-b) quinoline (Gorlitzer, K.; Weber, J. Arch. Pharm (Weinheim) 1980, 314, 76–84);

2-(2-((phenoxy)acetyl)amino)4-chlorobenzoic acid, 2-((2-((4-methoxy)phenoxy)acetyl)amino)benzoic acid, 2-((2-((4-methoxy)phenoxy)acetyl)amino)4-chlorobenzoic acid, 2-((2-((2-methoxy)phenoxy) acetyl)amino)benzoic acid, 2-((2-((2-methoxy) phenoxy)acetyl)amino)4-chlorobenzoic acid, 2-((2-(4-chlorophenoxy)acetyl)amino)benzoic acid, 2-((2-(4-chlorophenoxy)acetyl)amino)4-chlorobenzoic acid, 2-((2-((2,4,5-trichloro)phenoxy)acetyl)amino)benzoic acid, 2-((2-((2,4,5-trichloro)phenoxy)acetyl)amino)4-chlorobenzoic acid, 2-((2-((3,4-dichloro)phenoxy) acetyl)amino)benzoic acid, 2-((2-((3,4-dichloro) phenoxy)acetyl)amino)4-chlorobenzoic acid, 2-((2-((3, 4-methylenedioxy)phenoxy)acetyl)amino)benzoic acid and 2-((2-((4-cyano)phenoxy)acetyl)amino)benzoic acid have been synthesized by Sunder and Peet (Sunder, S.; Peet, N. P. J. Heterocyclic Chem. 1978, 15, 1379–1382); and 2-(2-((phenylthio)acetyl)amino) benzoic acid has been used to prepare 11-chlorobenzothieno(3,2-b)quinoline ((1) Yamato, M. U.S. Pat. No. 4,826,850; (2) Gorlitzer, K.; Weber, J. Arch. Pharm (Weinheim) 1980, 314, 76–84 (3) Yamato, M.; Takeuchi, Y.; Hashigaki, K.; Ikeda, Y.; Chang, M.-r.; Takeuchi, K.; Matsushima, M.; Tsuruo, T.; Tashiro, T.; Tsukagoshi, S.; Yamashita, Y.; Nakano, H. J. Med. Chem. 1989, 32, 1295), and has been used by Gorlitzer as an intermediate to prepare 11-oxo-5,11-dihydrobenzothieno(3,2-b)quinoline (Gorlitzer, K.; Weber, J. Arch. Pharm (Weinheim) 1980, 314, 76–84). None of the above compounds to our knowledge have been evaluated for use as anti-hyperglycemic agents.

U.S. Pat. No. 4,810,716 mentions compounds of generic structure:

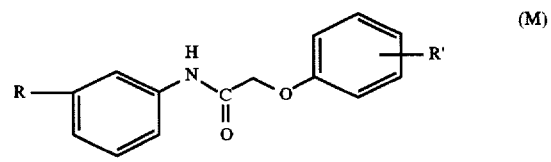

with activity as lipoxygenase inhibitors.

U.S. Pat. No. 4,182,776 mentions compounds of generic structure:

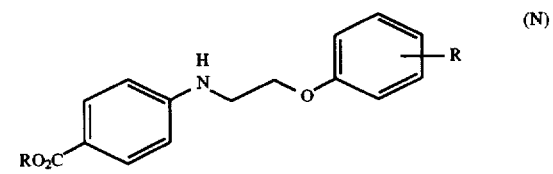

with activity as hypolipidemic agents for lowering levels of cholesterol, triglycerides, and phospholipids in serum.

U.S. Pat. No. 5,153,226 mentions compounds of generic structure:

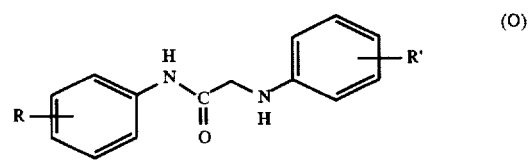

with activity as ACAT inhibitors for treating hypocholesterolemia.

U.S. Pat. No. 4,238,506 mentions compounds of generic structure:

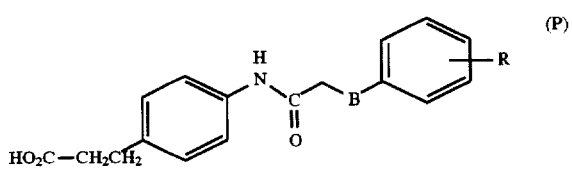

wherein B is O or S. It is noted that this patent teaches a different set of compounds from the presently taught novel compounds. The compounds are alleged to have hypoglycaemic and/or hypolipidaemic activity. U.S. Pat. Nos. 4,810,716, 4,182,776, 5,153,226, and 4,238,506 do not describe, much less enable the novel claimed compounds or the use of any of the presently described novel compounds for hypoglycemia.

Routes directed to the synthesis of various aniline derivatives are known. 1,2-Bis((2-carboxyphenyl)amino)ethane has been synthesized ((a) Formanovskii, A. A. *Zh. Org. Khim.* 1986, 22, 1103; (b) Sandhu, G. K.; Verma, S. P.; Moore, L. S.; Parish, R. V. *J. Organomet. Chem.* 1986, 315, 309, and bis(phenylamino)ethanes have been synthesized (Wanzlick, H. W.; Lochel, W. *Chem. Ber.* 1953, 1463–1466). To our knowledge, no report exists concerning the preparation of an unsymmetrical 1-((2-carboxyphenyl)amino)-2-(phenylamino)ethane.

The novel compounds and method of using them of the present invention fill a persistent need for effective antihyperglycemic and/or anti-diabetic agents.

Citation or identification of any reference in Section 2 of this application shall not be construed as an admission that such reference is available prior art to the invention.

3. SUMMARY OF THE INVENTION

The present invention provides novel aniline derivatives, as well as pharmaceutically acceptable salts thereof, having antihyperglycemic activity, particularly in diabetic subjects; pharmaceutical compositions comprising the novel aniline derivatives of the present invention; as well as methods for their use. Thus, the invention provides compounds of formula I:

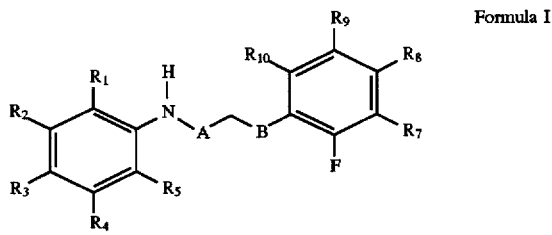

Formula I and pharmaceutically acceptable salts thereof, wherein:

$R_1$, $R_2$, $R_3$, $R_4$, and $R_5$ are independently selected from the group consisting of hydrogen, halogen, $OR_{11}$, $C(X)_3$, a $C_1-C_6$ alkyl group, $(CH_2)_nCH_2OH$, $(CH_2)_nCOOR_{12}$, and $(CH_2)_n$-5-tetrazolyl, where one but not more than one of $R_1$, $R_2$, $R_3$, $R_4$, and $R_5$ is selected from the group consisting of $(CH_2)_nCOOR_{12}$ and $(CH_2)_n$-5-tetrazolyl;

$R_{11}$ and $R_{12}$ are independently selected from the group consisting of hydrogen and a $C_1-C_6$ alkyl group;

X is halogen;

n is 0 or 1;

$R_7$, $R_8$, $R_9$, and $R_{10}$ are independently selected from the group consisting of hydrogen, halogen, $OR_{13}$, $SR_{14}$, $C(Y)_3$, a $C_1-C_6$ alkyl group, and phenyl;

$R_{13}$ and $R_{14}$ are independently selected from the group consisting of hydrogen, a $C_1-C_6$ alkyl group, and phenyl;

Y is halogen;

A is selected from the group consisting of C=O and $CH_2$; and

B is selected from the group consisting of NH, oxygen, and sulfur, which are useful as antihyperglycemic agents.

Preferred compounds of formula I useful as antihyperglycemic agents are:

2-(2-(((2-fluorophenyl)amino)acetyl)amino)benzoic acid (Compound AB);

2-(2-((2-fluorophenyl)amino)acetyl)amino)-5-fluorobenzoic acid (Compound AU);

2-(2-(((2-fluorophenyl)amino)acetyl)amino)-6-fluorobenzoic acid (Compound AW);

2-(2-((2-fluorophenyl)amino)acetyl)amino)-4-chlorobenzoic acid (Compound AZ);

2-(2-(((2-fluorophenyl)amino)acetyl)amino)5-bromobenzoic acid (Compound BG);

2-(2-((2-fluorophenyl)amino)acetyl)amino)-5-chlorobenzoic acid (Compound BB);

2-(2-(((2-fluorophenyl)amino)acetyl)amino)-5-methoxybenzoic acid (Compound BE);

4-(2-(((2-fluorophenyl)amino)acetyl)amino)benzoic acid (Compound AP);

methyl 2-(2-(((2-fluorophenyl)amino)acetyl)amino) benzoate (Compound BL);

2-(2-(((2-fluorophenyl)thio)acetyl)amino)benzoic acid (Compound AO);

4-((2-((2-Fluorophenyl)amino)acetyl)amino)-1-butoxybenzene (Compound CN);

4-((2-((2-Fluorophenyl)amino)acetyl)amino)phenol (Compound CP); and 2-((2-(Fluorophenyl)amino)acetyl)aminobenzene (Compound CR).

The present invention further provides compositions comprising the novel aniline derivatives of formula I for use as antihyperglycemic agents and methods for their use.

The present invention also provides compounds of the general formula II

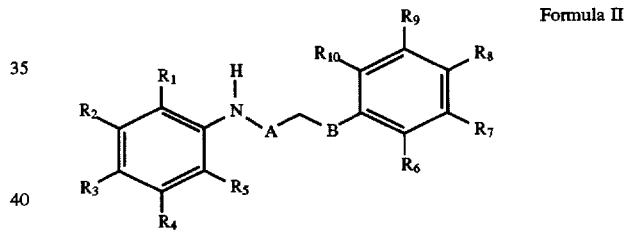

Formula II and pharmaceutically acceptable salts thereof, wherein:

$R_1$, $R_2$, $R_3$, $R_4$, and $R_5$ are independently selected from the group consisting of hydrogen, halogen, $OR_{11}$, $C(X)_3$, a $C_1-C_6$ alkyl group, $(CH_2)_nCH_2OH$, $(CH_2)_nCOOR_{12}$, and $(CH_2)_n$-5-tetrazolyl, where one but not more than one of $R_1$, $R_2$, $R_3$, $R_4$, or $R_5$ is selected from the group consisting of $(CH_2)_nCOOR_{12}$ and $(CH_2)_n$-5-tetrazolyl;

$R_{11}$ and $R_{12}$ are independently selected from the group consisting of hydrogen and a $C_1-C_6$ alkyl group;

X is halogen;

n is 0 or 1;

$R_6$, $R_7$, $R_8$, $R_9$, and $R_{10}$ are independently selected from the group consisting of hydrogen, halogen, $OR_{13}$, $SR_{14}$, $C(Y)_3$, a $C_1-C_6$ alkyl group, and phenyl;

$R_{13}$ and $R_{14}$ are independently selected from the group consisting of hydrogen, a $C_1-C_6$ alkyl group, and phenyl;

Y is halogen;

A is $CH_2$; and

B is selected from the group consisting of NH, oxygen, and sulfur, which have surprisingly been discovered to be useful as antihyperglycemic agents.

A preferred compound of formula II useful as a antihyperglycemic agent is 1-(2-carboxyphenyl)amino)-2-((2-fluorophenyl)amino)ethane (Compound BN).

The present invention further provides compositions comprising the aniline derivates of formula II for use as antihyperglycemic agents and methods for their use.

The present invention further provides novel methods for using compounds of the general formula III:

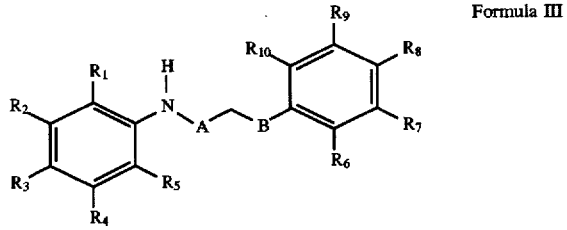

Formula III and pharmaceutically acceptable salts thereof, wherein:

$R_1$, $R_2$, $R_3$, $R_4$, and $R_5$ are independently selected from the group consisting of hydrogen, halogen, $OR_{11}$, $C(X)_3$, a $C_1$–$C_6$ alkyl group, $(CH_2)_nCH_2OH$, $(CH_2)_nCOOR_{12}$, and $(CH_2)_n$-5-tetrazolyl, where one but not more than one of $R_1$, $R_2$, $R_3$, $R_4$, or $R_5$ is selected from the group consisting of $(CH_2)_nCOOR_{12}$ and $(CH_2)_n$-5-tetrazolyl;

$R_{11}$ and $R_{12}$ are independently selected from the group consisting of hydrogen and a $C_1$–$C_6$ alkyl group;

X is halogen;

n is 0 or 1;

$R_6$, $R_7$, $R_8$, $R_9$, and $R_{10}$ are independently selected from the group consisting of hydrogen, halogen, $OR_{13}$, $SR_{14}$, $C(Y)_3$, a $C_1$–$C_6$ alkyl group, and phenyl;

$R_{13}$ and $R_{14}$ are independently selected from the group consisting of hydrogen, a $C_1$–$C_6$ alkyl group, and phenyl;

Y is halogen;

A is C=O; and

B is selected from the group consisting of NH, oxygen, and sulfur, useful as antihyperglycemic agents.

Preferred compounds of formula III useful as antihyperglycemic agents are:

2-(2-((phenylamino)acetyl)amino)-5-chlorobenzoic acid (Compound BA);

2-(2-(((3-fluorophenyl)amino)acetyl)amino)benzoic acid (Compound AC);

2-(2-(((4-(phenyl)phenyl)amino)acetyl)amino)benzoic acid (Compound AE);

2-(2-(((4-(trifluoromethyl)phenyl)amino)acetyl)amino) benzoic acid (Compound AG);

2-(2-(((2,3-dimethylphenyl)amino)acetyl)amino)benzoic acid (Compound AH);

2-(2-(((2,3-dichlorophenyl)amino)acetyl)amino)benzoic acid (Compound AI);

2-(2-((phenylamino)acetyl)amino)benzoic acid (Compound AK);

2-(2-(((2-(trifluoromethyl)phenyl)amino)acetyl)amino) benzoic acid (Compound AL); and 2-(2-(((4-(trifluoromethyl)phenyl)thio)acetyl)amino) benzoic acid (Compound AN);

2-(2-(((4-methoxyphenyl)amino)acetyl)amino)benzoic acid (Compound AF);

Methyl 2-(((2-(4-(trifluoromethyl)phenyl)amino)acetyl) amino)benzoate (Compound CB);

Methyl 4-(((2-(4-(Trifluoromethyl)phenyl)amino)acetyl) amino)benzoate (Compound CJ);

4-(((2-(4-(Trifluoromethyl)phenyl)amino)acetyl)amino) benzoic Acid (Compound CL)

4-(((2-(2-(Trifluoromethyl)phenyl)amino)acetyl)amino) benzoic Acid (Compound CM)

2-(2-((Phenylamino)acetyl)amino)-5-methoxybenzoic Acid (Compound BD);

2-(2-(((4-Fluorophenyl)amino)acetyl)amino)benzoic Acid (Compound AD);

2-(2-((Phenylamino)acetyl)amino)-5-bromobenzoic Acid (Compound BF);

2-(2-((Phenylamino)acetyl)amino)-6-fluorobenzoic Acid (Compound AV);

2-(2-(((2-Methoxyphenyl)amino)acetyl)amino)benzoic Acid (Compound AJ);

2-((2-(Phenylthio)acetyl)amino)benzoic Acid (Compound BJ);

2-(2-(((4-Fluorophenyl)amino)acetyl)amino)-5-flurobenzoic Acid (Compound AR); and 4,5-difluoro-2-((2-(phenylamino)acetyl)amino)benzoic acid as antihyperglycemic or hypoglycemic agents.

A further preferred compound of the invention is 1,2-Bis ((2-Carboxyphenyl)amino)ethane (Compound BM), and pharmaceutically acceptable salts thereof.

The present invention further provides compositions comprising the aniline derivatives of formula III for use as antihyperglycemic agents and methods for using the same.

The present invention may be understood more fully by reference to the following figures, detailed description and illustrative examples which are intended to exemplify non-limiting embodiments of the invention.

4. DESCRIPTION OF THE FIGURES

FIG. 1 is a flow chart illustrating generally preparation of the aniline derivatives 4 whereby an optionally substituted aniline 1 is first acylated with a haloacetyl halide and then condensed with nucleophile 3. $R_1$–$R_5$, $R_6$–$R_{10}$, and B are defined above in Section 3; W is bromine or chlorine.

FIG. 2 is a flow chart illustrating an alternative preparation of the aniline derivatives 4 whereby aniline, phenol, or thiophenol 3 is first alkylated, and then condensed with an optionally substituted aniline 1. $R_1$–$R_5$, $R_6$–$R_{10}$, and B are defined above in Section 3; X is OH or OBn.

5. DETAILED DESCRIPTION OF THE INVENTION

5.1 SYNTHESIS OF THE ANILINE DERIVATIVES

The aniline derivatives of the present invention can be prepared by methods known to those skilled in the art or by the synthetic methods outlined below.

Figure 1:
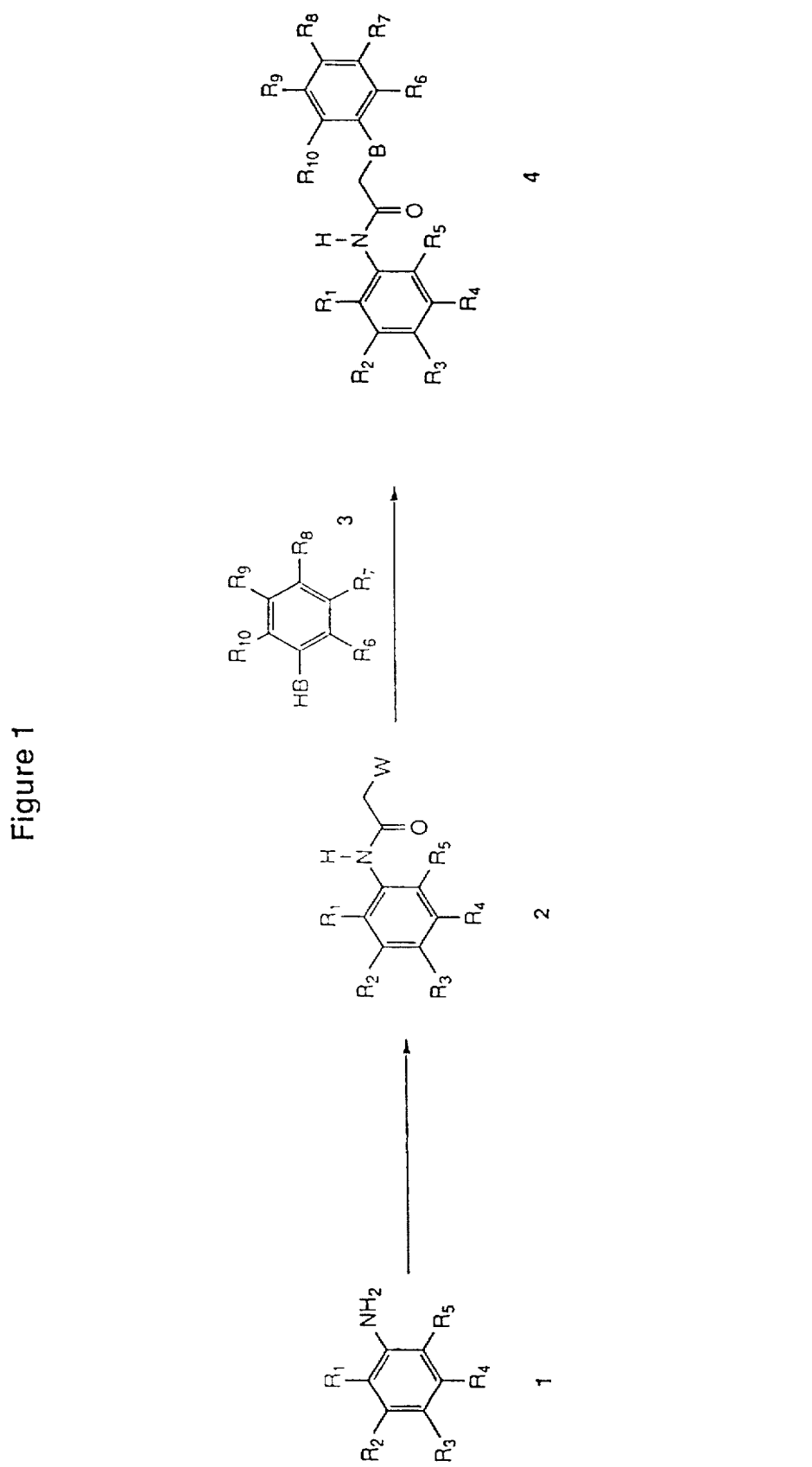

As shown in FIG. 1, aniline derivatives 4 can be prepared from optionally substituted anilines 1. The general procedure outlined in FIG. 1 has been modified from previously described procedures known to synthesize acylaniline derivatives ((1) Yamato, M.; Takeuchi, Y.; Chang, M-r.; Hashigaki, K. Chem. Pharm. Bull. 1992, 40, 528; (2) Yamato, M.; Takeuchi, Y.; Chang, M-r.; Hashigaki, K.; Tsuruo, T.; Tashiro, T.; Tsukagoshi, S. Chem. Pharm. Bull. 1990, 38, 3048; (3) Takeuchi, Y.; Chang, M-r.; Hashigaki, K.; Yamato, M. *Chem. Pharm. Bull.* 1991, 39, 1629; (4) Chang, M-r.; Takeuchi, Y.; Hashigaki, K.; Yamato, M. *Heterocycles* 1992, 33, 147; (5) Takeuchi, Y.; Chang, M-r.; Hashigaki, K.; Tashiro, T.; Tsuruo, T.; Tsukagoshi, S.; Yamato, M. *Chem. Pharm. Bull.* 1992, 40, 1481; (6) Görlitzer, K.; Stockmann, R.; Walter, W. D. *Pharmazie*, 1994, 49, 231). The optionally substituted anilines 1 are acylated with chloroacetyl chloride or bromoacetyl bromide in a polar solvent such as DMF, dioxane, or DMF/dioxane mixtures to provide haloacylanilines 2 ((1) Ossman, A. E.; El-Zahabi, M. M.; El-Hakim, A. E.; Osman, A. N. *Egypt. J. Chem.* 1988, 31, 381; (2) U.S. Pat. No. 3,374,264 to Uskokovic et al.). Amination of the haloacylanilines 2 with optionally substituted 3 provides the aniline derivatives 4.

Figure 2:
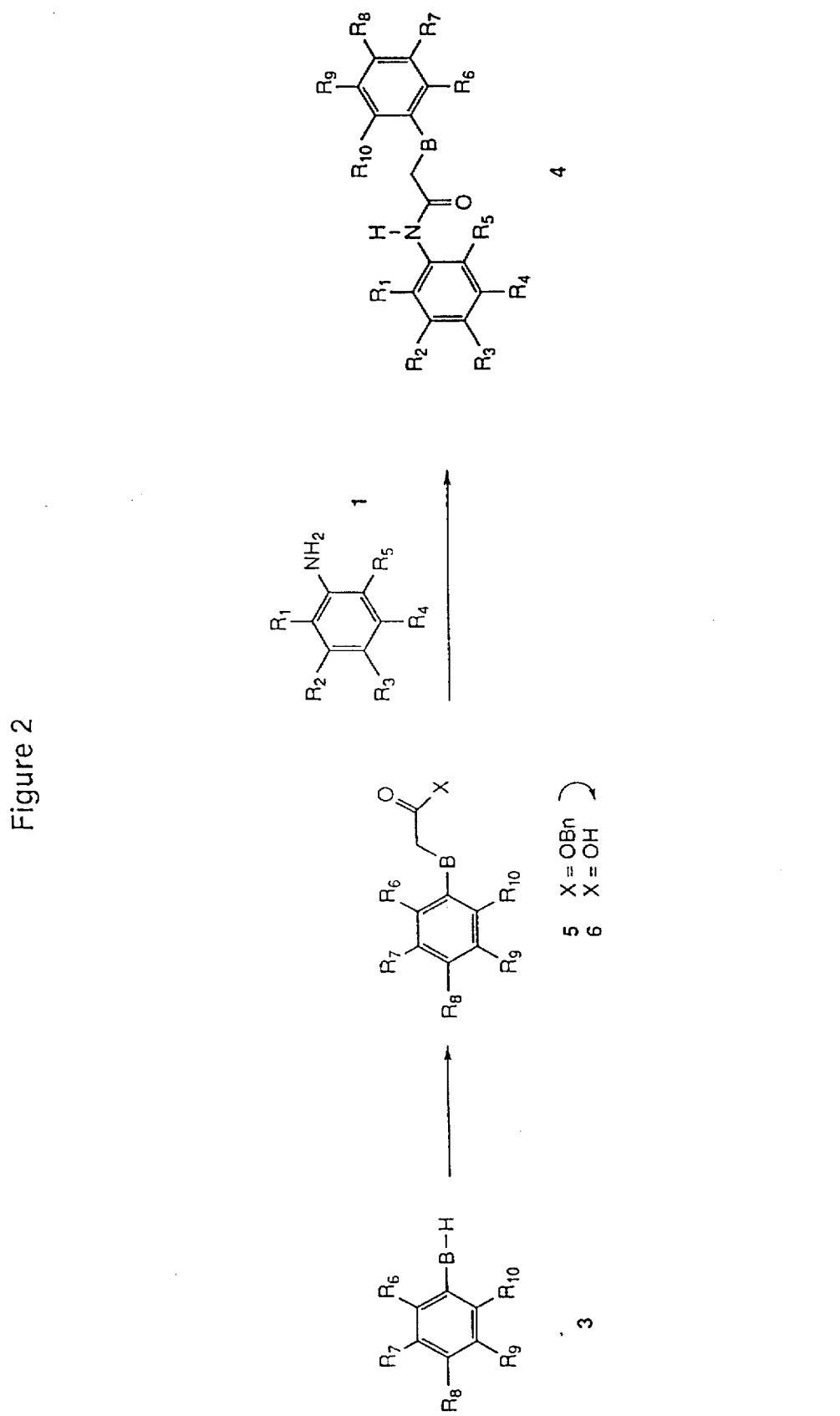

FIG. 2 shows an alternative preparation of aniline derivatives 4 using modified literature methods ((1) Yamato, M.; Hashigaki, K. EP 0376166; (2) Yamato, M. U.S. Pat. No. 4,826,850; (3) Sunder, S.; Peet, N. P. *J. Heterocyclic Chem.* 1978, 15, 1379; (4) Gorlitzer, K.; Weber, J. *Arch. Pharm (Weinheim)* 1980, 314, 76). Optionally substituted 3 is alkylated with chloroacetic acid or bromoacetic acid, providing acetic acids 6. Subsequent activation of 6 via its acid halide using thionyl chloride, thionyl bromide, or other common methods known to those skilled in the art, or via its mixed anhydride (Grote, C. W.; Kim, D. J.; Rapoport, H. *J. Org. Chem.* 1995, 60, 6987), and then reaction with an optionally substituted aniline 1 provides the aniline derivatives 4.

Alternatively, optionally substituted 3 (when B is NH or O) is alkylated with benzyl bromoacetate or benzyl chloroacetate in the presence of a base such potassium carbonate, sodium carbonate, sodium acetate, potassium acetate, or other common bases known to those skilled in the art, to provide acetate 5, which is then subjected to hydrogenolysis to provide acetic acid 6 (Zahler, R.; Koster, W. H.; Slusarchyk, W. A. EP 138 407).

Figure 3:
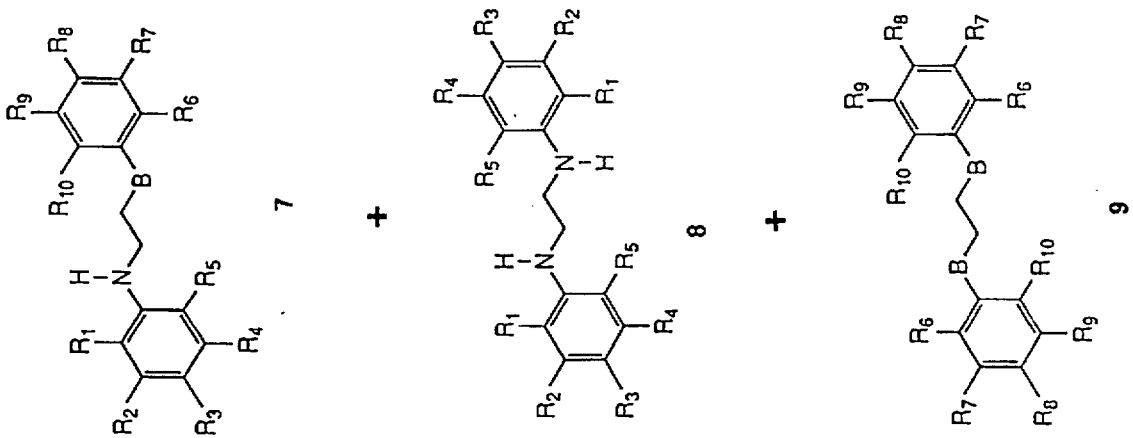
FIG. 3 is a flow chart describing a general preparation of aniline derivatives 7, 8, and 9. $R_1$–$R_5$, $R_6$–$R_{10}$, and B are defined above in Section 3; W is bromine or iodine.
Figure 3:
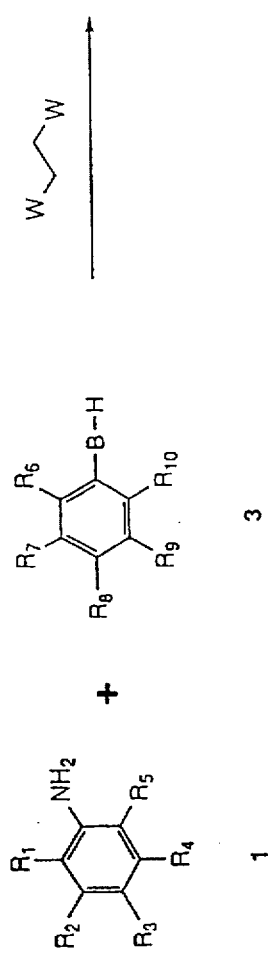

FIG. 3 illustrates a general preparation of anilines 7, 8, and 9 using modified literature conditions optimized to provide the previously unreported unsymmetrical anilines 7. The references listed below provide for the formation of symmetrical anilines 8 and 9 ((1) Formanovskii, A. A. *Zh. Org. Khim.* 1986, 22, 1103; (2) Sandhu, G. K.; Verma, S. P.; Moore, L. S.; Parish, R. V. *J. Organomet. Chem.* 1986, 315, 309; (3) Wanzlick, H. -W.; Löchel, W. *Chem. Ber.* 1953, 86, 1463; (4) Jaunin, R. *Helv. Chim. Acta* 1956, 39, 111; (5) Black, D. St.C.; Hartshorn, A. J.; Horner, M.; Hünig, S. *Aust. J. Chem.* 1977, 30, 2493). Reaction of optionally substituted 1 and optionally substituted 3 with a dihaloethane in the presence of a base such as potassium hydroxide or sodium hydroxide provides aniline 7 along with anilines 8 and 9, which are separable by recrystallization or preferably, by chromatography.

Figure 4:
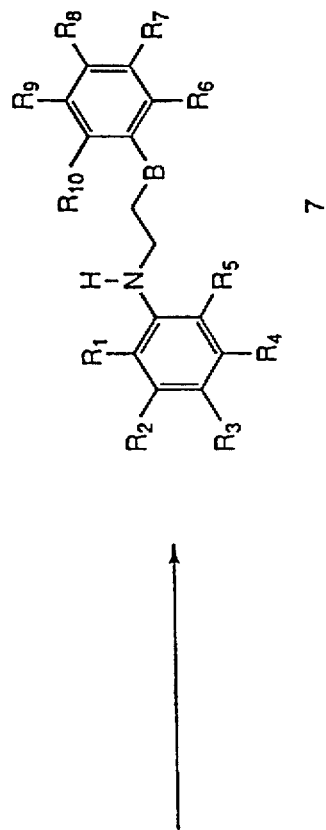
FIG. 4 is a flow chart illustrating another general preparation of the aniline derivative 7. $R_1$–$R_5$, $R_6$–$R_{10}$, and B are defined above in Section 3.
Figure 4:
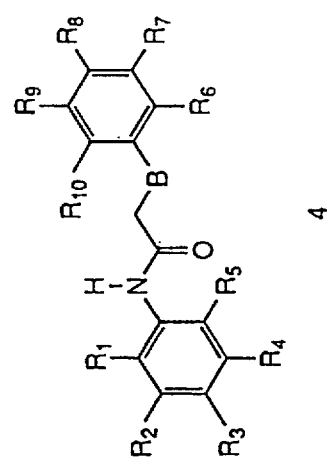

FIG. 4 illustrates a general preparation of the previously unreported anilines 7 by reduction of anilines 4 using a borane reagent such as $BH_3$.THF, (see general procedure reported by Rapoport et al. for amide reductions (i.e. Grote, C. W.; Kim, D. J.; Rapoport, H. *J. Org. Chem.* 1995, 60, 6987), $BH_3$.DMS, Red-Al (see amide reduction procedure reported in Hipskind, P. A.; Howbert, J. J.; Cho, S.; Cronin, J. S. Fort, S. L.; Ginah, F. O.; Hansen, G. J.; Huff, B. E.; Lobb, K. L.; Martinelli, M. J.; Murray, A. R.; Nixon, J. A.; Staszak, M. A.; Copp, J. D. *J. Org. Chem.* 1995, 60, 7033), or other reagents commonly employed in the art for amide reductions.

The optionally substituted anilines 1 and anilines, phenols, or thiophenols 3 are commercially available, or can be prepared by methods known to those skilled in the art. Aniline derivatives 4 and 7 can be further elaborated as appropriate according to methods commonly employed in the art.

5.2 METHODS AND COMPOSITIONS FOR USE OF ANILINE DERIVATIVES

The aniline derivatives of the present invention are useful in veterinary and human medicine for lowering the blood glucose level in a mammal. For example, due to the potent activity of the aniline derivatives of the present invention, the aniline derivatives are advantageously useful in veterinary and human medicine for the therapeutic treatment of insulin-dependent or non-insulin-dependent diabetes mellitus, either primary (idiopathic) or secondary to the use of diabetogenic drugs (e.g., diuretics, corticosteroids, etc.) Additionally, the described aniline derivatives can be advantageously used as antihyperglycemic agents to reduce the blood glucose levels in situations of acute stress such as experienced by animals or patients with hyperthermia, trauma, sepsis, and burns and undergoing general anesthesia. Hyperglycemia sometimes associated with severe head injury, cerebral thrombosis, encephalitis and heat stroke can also be therapeutically treated with these aniline derivatives. Additionally, the aniline derivatives are useful as antihyperglycemic agents for rare congenital metabolic glycogen storage disease associated with hyperglycemia.

Although the present inventors do not wish to be limited to any particular mechanism of action to explain the antihyperglycemic activity of the aniline derivatives of the present invention, it is envisaged that they may advantageously be useful for the treatment of both insulin-dependent (IDDM) or type I diabetes (formerly termed juvenile-onset or ketosis-prone diabetes) and non-insulin-dependent (NIDDM) or type II diabetes (formerly termed adult-onset diabetes).

When administered to a mammal for veterinary use or to a human for clinical use, the aniline derivatives can be used alone, or as a pharmaceutical composition comprising a physiologically acceptable carrier such as water, an aqueous solution, normal saline, or other physiologically acceptable excipient. In general, the dosage of such pharmaceutical composition ranges from about 10–2000 mg/kg/day, preferably about 10–250 mg/kg/day.

Pharmaceutical compositions comprising the aniline derivatives of the present invention can be administered by a number of routes, including, but not limited to: orally, injection including, but not limited to intravenously, intraperitoneally, subcutaneously, intramuscularly, etc; topically, nasally; and parenterally. The preferred route of administration is oral. Additionally, the aniline derivatives can be administered in conjunction with another antihyperglycemic agent including such as insulin; a biguanide such as metformin or buformin; a sulfonylurea such as acetohexamide, chlorpropamide, tolazamide, tolbutamide, glyburide, glypizide or glyclazide; a thiazolidinedione such as troglitazone or ciglitazone; an α-glycosidase inhibitor such as acarbose or miglatol; an $α_2$-adrenergic antagonist such as midaglizole, or a $β_3$-adrenergic receptor agonist such as CL-316,243, LY 104119, Ro 40-2148, etc.

Pharmaceutical compositions of the present invention suitable for oral administration may be administered as discrete units such as capsules, cachets or tablets each containing a predetermined amount of the aniline derivative (s); as a powder or granules; as a solution or a suspension in an aqueous liquid or a non-aqueous liquid; or as an oil-inwater liquid emulsion or a water-in-oil liquid emulsion and as a bolus, etc.

A tablet may be made by compression or molding, optionally with one or more accessory ingredients. Compressed tablets may be prepared by compressing in a suitable machine the aniline derivative in a free-flowing form such as a powder or granules, optionally mixed with a binder, lubricant, inert diluent, preservative, surface-active or dispersing agent known to those skilled in the art. Molded tablets may be made by molding in a suitable machine a mixture of the powdered compound moistened with an inert liquid diluent. The tablets may optionally be coated or scored and may be formulated so as to provide slow or controlled release of the aniline derivative(s) therein.

Formulations suitable for topical administration include lozenges comprising the ingredients in a flavored basis, usually sucrose and acacia or tragacanth; pastilles comprising the aniline derivative in an inert basis such as gelatin and glycerin, or sucrose and acacia; and mouthwashes comprising the aniline derivative to be administered in a suitable liquid carrier.

Pharmaceutical compositions suitable for topical administration to the skin may be administered as ointments, creams, gels, and pastes comprising the aniline derivative(s) to be administered in a pharmaceutically acceptable carrier. A preferred topical delivery system is a transdermal patch containing the aniline derivative to be administered.

Pharmaceutical compositions suitable for nasal administration wherein the carrier is a solid, include a coarse powder having a particle size, for example, in the range 20 to 500 microns which is administered in the manner in which snuff is taken, i.e. by rapid inhalation through the nasal passage from a container of the powder held close up to the nose. Suitable formulations for nasal administration wherein the carrier is a liquid, as for example a nasal spray or as nasal drops, include aqueous or oily solutions of the aniline derivative(s).

Pharmaceutical compositions suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multidose containers, for example, sealed ampules and vials, and may be stored in a freeze-dried (lyophilized) condition requiring only the addition of a sterile liquid carrier, for example water for injections, immediately prior to use. Extemporous injection solutions and suspensions may be prepared from sterile powders, granules, and tablets of the kind described above.

Preferred unit dosage formulations are those containing a daily dose or unit, daily sub-dose, as recited above, or an appropriate fraction thereof, of the administered aniline derivative(s).

It should be understood that in addition to the additives particularly mentioned above the compositions of this invention may include other agents conventional in the art having regard to the type of composition in question, for example, those suitable for oral administration may include flavoring agents.

The aniline derivatives of the present invention can be administered in an effective amount either as neutral compounds or as anionic or cationic pharmaceutically acceptable salts using counter ions such as acetate, chloride, bromide, iodide, tartrate, fumarate, succinate, ascorbate, gluconate, malate, citrate, sodium, potassium, ammonium, trialkylammonium, etc.

In addition, the aniline derivatives or pharmaceutically acceptable salts thereof can be used for research purposes, for example, to investigate the mechanism of activity of antihyperglycemic agents.

As used herein, an "antihyperglycemically effective" amount is an amount of an aniline derivative of the present invention capable of lowering the blood glucose level in a mammal having hyperglycemia, to a level of blood glucose within the normal range for the mammal, following administration thereto.

Preferably, the aniline derivatives of the present invention are used in mammals to lower abnormally high glucose levels to normal levels of blood glucose.

The following series of Examples are presented by way of illustration and not by way of limitation on the scope of the invention.

6. EXAMPLES: SYNTHESIS OF THE ANILINE DERIVATIVES

6.1 MATERIALS AND METHODS

Tetrahydrofuran (THF) was distilled using potassium/ benzophenone; benzene, toluene, and methylene chloride were distilled using calcium hydride. Anhydrous dimethylformamide (DMF) and anhydrous dioxane were obtained from Aldrich. Bromoacetyl bromide was distilled prior to use. All other reagents were used as received. All moisture and air sensitive reactions were conducted under a nitrogen atmosphere, using dry solvents. Following extractive workup, organic solutions were dried over anhydrous $Na_2SO_4$ or $MgSO_4$, and evaporation of solvents was done on a rotary evaporator at room temperature (rt). Low pressure liquid chomatography (LPLC) was performed on E. Merck 230–400 mesh silica gel using nitrogen pressure. $^1H$ and $^{13}C$ NMR were recorded on a 400 MHz spectrometer. NMR shifts are expressed in ppm downfield from internal tetramethylsilane. NMR coupling constants are reported in Hertz. Mass spectrometry was performed by the Physical Chemistry Department at Shaman Pharmaceutical. Elemental analyses were performed by the Analytical Services Department at University of California, Berkeley. Melting points were determined using a Buchi model 535 melting point apparatus and are uncorrected.

6.2 ANILINE DERIVATIVES SYNTHESIZED

Example 1

2-((2-Bromoacetyl)amino)benzoic Acid (Compound AA)

A solution of anthranilic acid (50 g, 364.6 mmol) in a mixture of anhydrous DMF (125 mL) and dioxane (125 mL) in a 1 L morton flask equipped with a mechanical stirrer and a constant addition funnel was cooled with an ice-bath to 0° C. Distilled bromoacetyl bromide (73.6 g, 31.77 mL, 364.6 mmol) was added dropwise keeping the internal temperature between 0°–1.5° C. over a 2.5 h period. After the addition was completed, the ice-bath was removed and stirring was continued for 5 h at ft. The reaction mixture was cooled in an ice-bath and water (300 mL) was slowly added. A white precipitate formed, which was filtered, washed sequentially with 5% HBr solution (500 mL) and water (500 mL), and then dried in a vacuum desiccator. Further drying in a vacuum oven at 60° C. afforded 82.61 g (87.8%) of the title compound as a white powder: mp 164.6°–167.6° C. (lit. 165.5°–172° C. (Hoffman LaRoche U.S. Pat. No.

3,244,698)); ¹H NMR (DMSO-d₆) δ13.7 (bs, 1H), 11.60 (s, 1H), 8.44 (d, J=8.0, 1H), 8.00 (dd, J=8.0, J=1.6, 1H), 7.62 (dt, J=8.0, J=1.6, 1H), 7.21 (t, J=8.0, 1H); 4.26 (s, 2H); ¹³C NMR (DMSO-d₆) δ169.20, 165.05, 139.95, 134.08, 131.13, 123.46, 120.02, 117.09, 30.67; MS (EI, m/z) 256.9 (M⁺), 258.9 (M⁺2⁺). HRMS (EI) calcd for C₉H₈NO₃Br 256.9686, found 256.9695.

Example 2
2-(2-(((2-Fluorophenyl)amino)acetyl)amino)benzoic Acid (Compound AB)

A solution of 2-((2-bromoacetyl)amino)benzoic acid from Example 1 (8.00 g, 31.0 mmol) and ortho-fluoroaniline (7.48 mL, 77.5 mmol) in DMF (80 mL) was heated to 75° C. for 8 h. The mixture was cooled, poured over H₂O (1 L) and 5% KOH (300 mL), and then washed with CH₂Cl₂ (3×300 mL). The aqueous layer was acidified to pH 2 with 2N HCl, chilled, and then filtered. The filter cake was rinsed with water (60 mL) and dried under high vacuum at 45° C. to yield 7.62 g (85%) of the title compound as an off-white solid: mp 196° C.; ¹H NMR (DMSO-d₆) δ13.54 (bs, 1H), 12.01 (s, 1H), 8.72 (d, J=8.4, 1H), 7.93 (dd, J=8, J=1.4, 1H), 7.59 (td, J=7.2, J=1.6, 1H), 7.13 (t, J=7.6, 1H), 7.05 (dd, J=11.6, J=8.0, 1H), 6.94 (t, J=7.6, 1H), 6.58 (m, 2H), 6.37 (bs, 1H), 3.90 (d, J=5.6, 2H); ¹³C NMR (DMSO-d₆) δ170.30, 169.19, 151.02 (J=238.1), 140.56, 136.00 (J=11.3), 134.20, 131.12, 124.77 (J=3.1), 122.71, 119.35, 116.80 (J=6.8), 114.52 (J=18.2), 111.81 (J=3.1), 48.23; MS (EI, m/z) 288.1 (M⁺).

HRMS (EI) calcd for C₁₅H₁₃N₂O₃F 288.0910, found 288.0907. Anal. Calcd for C₁₅H₁₃N₂O₃F.0.18 H₂O: C, 61.80; H, 4.62; N, 9.61. Found: C, 61.77; H, 4.54; N, 9.75.

Example 3
2-(2-(((3-Fluorophenyl)amino)acetyl)amino)benzoic Acid (Compound AC)

A solution of 2-((2-bromoacetyl)amino)benzoic acid from Example 1 (8.00 g, 31.0 mmol) and meta-fluoroaniline (7.45 mL, 77.5 mmol) in DMF (80 mL) was heated to 80° C. for 8 h. The mixture was cooled, poured over H₂O (1 L) and 5% KOH (300 mL), and then washed with CH₂Cl₂ (3×300 mL). The aqueous layer was acidified to pH 2 with 2N HCl, chilled, and then filtered. The filter cake was rinsed with cold water (100 mL) and dried under high vacuum at 45° C. to yield 7.00 g (78%) of the title compound as a grey solid: mp 209° C.; ¹H NMR (DMSO-d₆) δ13.5 (bs, 1H), 11.94 (s, 1H), 8.70 (d, J=8.4, 1H), 7.94 (dd, J=7.8, J=1.4, 1H), 7.60 (td, J=8.0, J=1.4, 1H), 7.15–7.07 (m, 2H), 6.83 (bs, 1H), 6.43–6.35 (m, 3H), 3.88 (s, 2H); ¹³C NMR (DMSO-d₆) δ170.29, 169.12, 163.25 (J=240.3), 150.17 (J=10.6), 140.52, 134.18, 131.13, 130.43 (J=10.6), 122.73, 119.40, 115.98, 108.42, 103.09 (J=21.2), 98.97 (J=25), 48.48; MS (EI, m/z) 388 (M⁺). HRMS (EI) calcd for C₁₅H₁₃N₂O₃F 288.0910, found 288.0915.

Example 4
2-(2-(((4-Fluorophenyl)amino)acetyl)amino)benzoic Acid (Compound AD)

A solution of 2-((2-bromoacetyl)amino)benzoic acid from Example 1 (8.00 g, 31.0 mmol) and para-fluoroaniline (7.34 mL, 77.5 mmol) in DMF (80 mL) was heated to 75° C. for 8 h. The mixture was cooled, poured over H₂O (1 L) and 5% KOH (300 mL), and then washed with CH₂Cl₂ (3×300 mL). The aqueous layer was acidified to pH 2 with 2N HCl, chilled, and then filtered. The filter cake was rinsed with water (60 mL) and dried under high vacuum at 45° C. to yield 7.98 g (89%) of the title compound as an off-white solid: mp 209° C.; ¹H NMR (DMSO-d₆) δ13.45 (bs, 1H), 12.00 (s, 1H), 8.72 (d, J=8, 1H), 7.94 (dd, J=8, J=1.2, 1H), 7.59 (td, J=7.2, J=1.6, 1H), 7.13 (td, J=7.2, J=0.8, 1H), 6.95 (m, 2H), 6.58 (m, 2H), 6.47 (s, 1H), 3.82 (s, 2H); ¹³C NMR (DMSO-d₆) δ170.73, 169.04, 154.95 (J=232.0), 144.78, 140.54, 134.15, 131.13, 122.69, 119.43, 116.00, 115.38 (J=21.9), 113.22 (J=7.6), 49.31. HRMS (EI) calcd for C₁₅H₁₃N₂O₃F 288.0910, found 288.0906.

Example 5
2-(2-(((4-(Phenyl)phenyl)amino)acetyl)amino)benzoic Acid (Compound AE)

A solution of 2-((2-bromoacetyl)amino)benzoic acid from Example 1 (8.00 g, 31.0 mmol) and para-aminobiphenyl (13.12 g, 77.5 mmol) in DMF (80 mL) was heated to 80° C. for 8 h. The mixture was cooled, poured over H₂O (1 L) and 5% KOH (300 mL), and then washed with CH₂Cl₂ (3×300 mL). The aqueous layer was acidified to pH 2 with 2N HCl, chilled, and then filtered. The filter cake was rinsed with cold water (100 mL) and dried under high vacuum at 45° C. The air sensitive material was triturated with ethyl acetate (100 mL), filtered, and rinsed with ethyl acetate (2×25 mL) to yield, after drying, 8.18 g (76%) of the title compound as a tan solid: mp 228° C.; ¹H NMR (DMSO-d₆) δ13.4 (bs, 1H), 12.05 (s, 1H), 8.75 (d, J=8.4, 1H), 7.95 (dd, J=7.4, J=1.2, 1H), 7.60 (td, J=7.2, J=1.2, 1H), 7.54 (d, J=7.6, 2H), 7.45 (d, J=8.8, 2H), 7.37 (t, J=7.6, 2H), 7.22 (t, J=7.6, 1H), 7.13 (t, J=7.6, 1H), 6.69 (d, J=8.4, 2H), 6.7 (bs, 1H), 3.90 (s, 2H); ¹³C NMR (DMSO-d₆) δ170.74, 169.12, 147.71, 140.60, 140.36, 124.20, 131.14, 128.87, 128.74, 127.28, 125.96, 125.55, 2122.69, 119.40, 115.97, 112.85, 48.87; MS (EI, m/z) 328 (M—H₂O). HRMS (EI) calcd for C₂₁H₁₈N₂O₃ 346.1317, found 346.1293

Example 6
2-(2-(((4-Methoxyphenyl)amino)acetyl)amino)benzoic Acid (Compound AF)

A solution of 2-((2-bromoacetyl)amino)benzoic acid from Example 1 (8.00 g, 31.0 mmol) and para-methoxyaniline (9.55 g, 77.5 mmol) in DMF (80 mL) was heated to 80° C. for 8 h. The mixture was cooled, poured over H₂O (1 L) and 5% KOH (300 mL), and then washed with CH₂Cl₂ (3×300 mL). The aqueous layer was acidified to pH 2 with 2N HCl, chilled, and then filtered. The filter cake was rinsed with cold water (100 mL) and dried under high vacuum at 45° C. to yield 7.62 g (85%) of the title compound as a white solid: mp 190° C.; ¹H NMR (DMSO-d₆) δ13.5 (bs, 1H), 12.04 (s, 1H), 8.73 (dd, J=8.4, J=1.0, 1H), 7.93 (dd, J=7.8, J=1.8, 1H), 7.59 (td, J=8.0, J=1.8, 1H), 7.13 (td, J=7.6, J=1.2, 1H), 6.73 (dt, J=8.8, J=2.2, 2H), 6.54 (dt, J=9.2, J=2.4, 2H), 6.2 (bs, 1H), 3.77 (s, 2H), 3.62 (s, 3H); ¹³C NMR (DMSO-d₆) δ171.18, 168.95, 151.53, 142.2, 140.58, 134.12, 131.12, 122.62, 119.42, 116.03, 114.57, 113.42, 55.20, 49.76; MS (EI, m/z) 300 (M⁺). HRMS (EI) calcd for C₁₆H₁₆N₂O₄ 300.1110, found 300.1104.

Example 7
2-(2-(((4-(Trifluoromethyl)phenyl)amino)acetyl)amino) benzoic Acid (Compound AG)

A -solution of 2-((2-bromoacetyl)amino)benzoic acid from Example 1 (3.0 g, 0.012 mol), p-(trifluoromethyl) aniline (3.7 g, 200 mol %), and DMAP (5 mol %) in anhydrous DMF (40 mL) was heated with stirring at 98°–105° C. for 12 h, cooled, and then poured into ice-water (400 mL). The pH of the mixture was adjusted to 9 with 5% KOH (40 mL), and then the milky homogonous solution was extracted with CH₂Cl₂ (3×70 mL). The combined CH₂Cl₂ extracts were set aside and the aqueous layer was acidified with 5% HBr to pH 3. The crystalline compound which formed was filtered and then dried in a vacuum oven for 10 h at 40°–45° C., affording 2.9 g (74%) of the title compound: mp 210°–211.6° C.; $^1$H NMR (DMSO-$d_6$) δ12.60 (bs, 1H, OH), 8.70 (d, 1H, J=8.4), 7.94 (dd, 1H, J=1.6, J=6.4), 7.59 (dt, J=1.6, J=7.6), 7.42 (d, 1H, J=8.8), 7.16–7.12 (m, 2H), 6.72 (d, 4H, J=8.4), 3.95 (s, 2H); $^{13}$C NMR (DMSO-$d_6$) δ169.89, 169.21, 151.19, 140.50, 134.21, 131.15, 126.34, 126.30, 126.27, 122.79, 119.42, 119.37, 115.96, 111.96, 48.08; MS (EI, m/z)338 (M$^+$). HRMS (EI) calcd for $C_{16}H_{13}N_2O_3F_3$ 338.0878, found 338.0876. Anal. Calcd for $C_{16}H_{13}N_2O_3F_3 \cdot 0.43$ $H_2O$: C, 55.54; H, 4.03; N, 8.09. Found: C, 55.53; H, 3.82; N, 8.00.

Example 8

2-(2-(((2,3-Dimethylphenyl)amino)acetyl)amino)benzoic Acid (Compound AH)

A solution of 2-((2-bromoacetyl)amino)benzoic acid from Example 1 (3.00 g, 11.6 mmol) and 2,3-dimethylaniline (3.55 mL, 29.1 mmol) in DMF (30 mL) was heated to 80° C. for 7 h. The mixture was cooled, poured over water (400 mL) and 5% KOH (125 mL), and then washed with $CH_2Cl_2$ (3×125 mL). The aqueous layer was acidified to pH 2 with 2N HCl, chilled, and then filtered. The filter cake was rinsed with cold water (25 mL) and dried. Trituration with ethyl acetate afforded 2.58 g (75%) of the title compound as an off-white solid: mp 209° C. (dec); $^1$H NMR (DMSO-$d_6$) δ13.4 (bs, 1H), 11.95 (s, 1H), 8.74 (d, J=8.4, 1H), 7.93 (dd, J=7.8, J=1.6, 1H), 7.58 (td, J=8.0, J=1.6, 1H), 7.12 (td, J=7.6, J=0.8, 1H), 6.86 (t, J=8.0, 1H), 6.49 (d, J=7.6, 1H), 6.22 (d, J=8.0, 1H), 5.83 (bs, 1H), 3.86 (s, 2H), 2.21 (s, 3H), 2.15 (s, 3H); $^{13}$C NMR (DMSO-$d_6$) δ170.98, 168.91, 145.56, 140.53, 135.61, 134.05, 131.10, 125.74, 122.51, 120.78, 119.32 (two carbons), 115.89, 107.19, 49.22, 20.27, 12.66; MS (EI, m/z) 298 (M$^+$) HRMS (EI) calcd for $C_{17}H_{18}N_2O_3$ 298.1317, found 298.1326.

Example 9

2-(2-(((2,3-Dichlorophenyl)amino)acetyl)amino)benzoic Acid (Compound AI)

A solution of 2-((2-bromoacetyl)amino)benzoic acid from Example 1 (3.00 g, 11.6 mmol) and 2,3-dichloroaniline (4.71 g, 29.1 mmol) in DMF (30 mL) was heated to 80° C. for 7 h. The mixture was cooled, poured over water (400 mL) and 5% KOH (125 mL), and then washed with $CH_2Cl_2$ (3×125 mL). The aqueous layer was acidified to pH 2 with 2N HCl, chilled, and then filtered. The filter cake was rinsed with cold water (25 mL) and dried. Trituration with ethyl acetate afforded 2.59 g (66%) of the title compound as an off-white solid: mp 223° C. (dec); $^1$H NMR (DMSO-$d_6$) δ13.55 (bs, 1H), 11.86 (s, 1H), 8.70 (d, J=8.4, 1H), 7.94 (dd, J=8.4, J=1.6, 1H), 7.60 (td, J=8.0, J=1.2, 1H), 7.16–7.10 (m, 2H), 6.86 (d, J=7.6, 1H), 6.60 (m, 1H), 6.53 (d, J=8.0, 1H), 4.01 (d, J=6.0, 2H); $^{13}$C NMR (DMSO-$d_6$) δ169.58, 169.22, 145.42, 140.46, 134.20, 131.67, 131.15, 128.47, 122.81, 119.44, 117.90, 116.21, 115.94, 109.59, 48.56; MS (EI, m/z) 338 (M$^+$). HRMS (EI) calcd for $C_{15}H_{12}N_2O_3Cl_2$ 338.0225, found 338.0200.

Example 10

2-(2-(((2-Methoxyphenyl)amino)acetyl)amino)benzoic Acid (Compound AJ)

A solution of 2-((2-bromoacetyl)amino)benzoic acid from Example 1 (3.00 g, 11.6 mmol) and 2-methoxyaniline (3.28 mL, 29.1 mmol) in DMF (30 mL) was heated to 80° C. for 7 h. The mixture was cooled, poured over water (400 mL) and 5% KOH (125 mL), and then washed with $CH_2Cl_2$ (3×125 mL). The aqueous layer was acidified to pH 2 with 2N HCl, chilled, and then filtered. The filter cake was rinsed with cold water (25 mL) and dried. Trituration with ethyl acetate afforded 2.53 g (72%) of the title compound as a grey solid: mp 197° C. (dec); $^1$H NMR (DMSO-$d_6$) δ13.63 (bs, 1H), 11.90 (s, 1H), 8.71 (d, J=8.4, 1H), 7.93 (dd, J=8.0, J=1.6, 1H), 7.59 (td, J=8.0, J=1.6, 1H), 7.13 (td, J=7.6, 1H), 6.85 (dd, J=8.0, J=1.2, 1H), 6.74 (td, J=7.6, J=1.2, 1H), 6.61 (td, J=8.0, J=1.2, 1H), 6.37 (dd, J=8.0, J=1.6, 1H), 5.83 (bs, 1H), 3.86 (s, 2H), 3.83 (s, 3H); $^{13}$C NMR (DMSO-$d_6$) δ170.79, 168.97, 146.80, 140.52, 137.69, 134.09, 131.08, 122.65, 121.06, 119.51, 116.96, 116.06, 110.24, 109.52, 55.56, 49.12. HRMS (EI) calcd for $C_{16}H_{16}N_2O_4$ 300.1110, found 300.1136.

Example 11

2-(2-((Phenylamino)acetyl)amino)benzoic Acid (Compound AK)

A solution of 2-((2-bromoacetyl)amino)benzoic acid from Example 1 (5.0 g, 19.37 mmol), aniline (4.51 g, 4.41 mL, 48.4 mmol) and anhyd DMF (50 mL) was heated in an oil bath at 85° C. for 4.5 h. The reaction mixture was cooled and poured into ice-water (500 mL). A solution of 5% KOH (100 mL) was added to dissolve the milky white suspension, and then the homogenous solution was extracted with $CH_2Cl_2$ (200 mL, 2×100 mL). The combined $CH_2Cl_2$ extract was set aside and the aqueous layer was acidified to pH=3 (pH meter) with 5% HBr. The precipitate which formed was washed with 5% HBr solution, water, and then dried in a vacuum oven at 50° C. for 2 days, yielding 4.74 g (90.6%) of a white powder: mp 192.4°–192.8° C. (sealed tube); $^1$H NMR (DMSO-$d_6$) δ13.41 (bs, 1H), 12.01 (s, 1H), 8.72 (d, J=8.4, 1H), 7.93 (dd, J=7.6, J=1.6, 1H), 7.59 (dt, J=8.8, J=1.6, 1H), 7.15–7.05 (m, 3H), 6.63–6.45 (m, 4H); 3.83 (s, 2H); $^{13}$C NMR (DMSO-$d_6$) δ170.85, 169.01, 148.11, 140.56, 134.13, 131.10, 128.94, 122.63, 119.38, 117.10, 115.96, 112.40, 48.93; MS (EI, m/z) 270.1 (M$^+$). HRMS (EI) calcd for $C_{15}H_{14}N_2O_3$ 270.1004, found 270.1009.

Example 12

2-(2-(((2-(Trifluoromethyl)phenyl)amino)acetyl)amino) benzoic Acid (Compound AL)

A solution of 2-((2-bromoacetyl)amino)benzoic acid from Example 1 (1.74 g, 6.7 mmol) and 2-aminobenzotrifluoride (2.17 g, 1.7 mL, 200 mol %) in anhydrous DMF (20 mL) was heated at 100° C. for 40 h, and then cooled to rt. The mixture was poured into ice-water, 5% KOH was added to adjust the pH of the mixture to 9, and then the solution was extracted with $CH_2Cl_2$ (3×50 mL). The combined $CH_2Cl_2$ extracts were set aside and the aqueous layer was acidified with 5% HBr to pH=3. The light crystalline compound which precipitated was filtered, washed with water several times, and then dried in a vacuum oven for 40 h, yielding 1.0 g (44%) of the title compound: mp 224°–226° C. (dec.); $^1$H NMR (DMSO-$d_6$) δ13.48 (bs, 1H, OH), 11.78 (s, 1H, NH), 8.69 (d, 1H, J=8.4, NH), 7.94 (dd, 1H, J=1.6, J=8), 7.58 (t, 1H, J=8.8), 7.46 (d, 1H, J=7.2), 7.40 (t, 1H, J=8), 7.16 (t, 1H, J=7.6), 6.74 (t, 1H, J=7.6), 6.62 (d, 1H, J=8.4), 6.30 (t, 1H, J=5.2), 4.03 (d, 2H, J=5.6); $^{13}$C NMR (DMSO-$d_6$) δ169.79, 169.04, 144.97, 140.43, 134.17, 133.67, 131.15, 126.37, 126.32, 122.85, 120.87, 119.65, 116.32, 116.08, 112.01, 48.58; MS (EI, m/z) 338 (M$^+$). HRMS (EI) calcd for $C_{16}H_{13}N_2O_3F_3$ 338.0878, found 338.0892.

Example 13

2-(2-(((2-Fluorophenyl)oxy)acetyl)amino)benzoic Acid (Compound AM)

A solution of o-fluorophenol (3.74 g, 200 mol %) in 70 mL of anhydrous THF was cooled to 10°–15° C. and treated with NaH (1.5 g, 200 mol % of a 50% dispersion in the mineral oil). The reaction mixture was stirred at 15° C. for 1 h, and then 2-((2-bromoacetyl)amino)benzoic acid from Example 1 (4.0 g, 0.016 mol) was added in one portion. After 15 min, the ice-bath was removed and the reaction mixture was stirred for 40 h at rt. TLC analysis showed the disappearance of the starting acid. Water (100 mL) was added, and then the reaction mixture was extracted with ether (3×70 mL). The separated water layer was acidified to pH 5 with 5% HCl and extracted with EtOAc (3×100 mL). The EtOAc layer was dried, filtered, concentrated, dried in vacuo for 1 h, and then triturated several times with cold ether. After air-drying overnight and then drying in a vacuum oven for 15 h at 40° C., 1.5 g (33%) of the title compound was obtained: mp 176°–178° C.; $^1$H NMR (DMSO-d$_6$) δ13.73 (bs, 1H, COOH), 12.04 (s, 1H, NH), 8.68 (dd, 1H, J=1.2, J=8.4, NH), 8.01 (dd, 1H, J=1.6, J=8), 7.65–7.61 (m, 1H), 7.29–7.11 (m, 5H), 7.04–6.98 (m, 1H), 4.84 (s, 2H); $^{13}$C NMR (DMSO-d$_6$) δ169.35, 166.90, 151.71 (d, J=244.80), 145.18 (d, J=10.66), 140.10, 134.26, 131.20, 124.78 (d, J=4.82), 123.17, 122.30, 122.23, 116.40, 116.23, 115.42, 68.16; MS (EI, m/z) 289 (M$^+$). HRMS (EI) calcd for C$_{15}$H$_{12}$NO$_4$F 289.0750, found 289.0773. Anal. Calcd for C$_{15}$H$_{12}$NO$_4$F: C, 62.28; H, 4.18; N, 4.84. Found: C, 61.90; H, 4.01; N, 4.80.

Example 14
2-(2-(((4-(Trifluoromethyl)phenyl)thio)acetyl)amino) benzoic Acid (Compound AN)

A solution of 4-(trifluoromethyl)thiophenol (1.0 g, 200 mol %) in 10 mL of anhydrous THF at 10° C. was treated with NaH (0.43 g, 200 mol % of 50% dispersion in oil). After 30 min at 15° C., 2-((2-bromoacetyl)amino)benzoic acid from Example 1 (0.72 g, 3.0 mmol) was added in one portion. The reaction mixture was stirred for 30 h at rt before TLC analysis showed the disappearance of the starting acid. Water (50 mL) was added, and then the mixture was extracted with ether (3×60 mL) to remove the excess thiophenol. The separated water layer was acidified to pH 5 and was extracted with EtOAc (3×70 mL). The combined EtOAc layer was dried, filtered, concentrated, and then the light-yellow crystalline compound which was obtained was triturated several times with ether. After drying overnight in vacuo, 0.52 g (53%) of the title compound was obtained as yellow crystals: mp 191°–191.6° C.; $^1$H NMR (DMSO-d$_6$) δ13.67 (bs, 1H, COOH), 11.75 (s, 1H, NH), 8.48 (d, 1H, NH, J=8), 7.95 (dd, 1H, J=1.6, J=8), 7.65 (d, 1H, J=8.4), 7.61–7.53 (m, 5H), 7.18–7.14 (m, 1H), 4.17 (s, 2H); $^{13}$C NMR (DMSO-d$_6$) δ169.14 (C=O), 166.81 (C=O), 141.53, 140.13, 134.04, 131.09, 127.03, 125.85, 125.81, 125.77, 125.73, 123.16, 119.99, 116.82, 36.68; MS (EI, m/z) 355 (M$^+$). HRMS (EI) calcd for C$_{16}$H$_{12}$NO$_3$F$_3$S 355.0490, found 355.0487. Anal. Calcd for C$_{16}$H$_{12}$NO$_3$F$_3$S: C, 54.00; H, 3.40; N, 3.94. Found: C, 53.83; H, 3.33; N, 3.98.

Example 15
2-(2-(((2-Fluorophenyl)thio)acetyl)amino)benzoic Acid (Compound AO)

A solution of 2-fluorothiophenol (3.97 g, 200 mol %) in anhydrous THF (50 mL) was cooled to 10°–15° C. and then NaH (1.4 g, 200 mol % of 50% dispersion in oil ) was added slowly. The reaction mixture was stirred at 15° C. for 40 min, and then 2-((2-bromoacetyl)amino)benzoic acid from Example 1 (4.0 g, 0.016 mol) was added in one portion. The reaction mixture was stirred for 24 h at rt before TLC showed the disappearance of the starting acid. The reaction mixture was diluted with water (70 mL) and then extracted with ether (3×60 mL) to remove the excess thiophenol. The water layer was acidified to pH 4-5 with 5% HCl, and then the light crystalline product which precipitated was filtered, washed several times with ether, and then dried in vacuo to give 1.0 g (22%) of the title compound as white crystals: mp 161°–162° C. The mother liquid was concentrated and the crystalline residue was washed several times with a small amount of ether, providing and additional 0.6 g (13%) of the title compound as white crystals: $^1$H NMR (DMSO-d$_6$) δ13.80 (bs, 1H, COOH), 11.73 (s, 1H, NH), 8.46 (d, 1H, J=8.00), 7.95 (d, 1H, J=8), 7.57 (s, 1H), 7.42 (s, 1H), 7.25 (s, 1H), 7.22 (s, 1H), 7.16 (s, 1H), 7.15 (s, 1H), 4.01(d, 2H, J=2.8); $^{13}$C NMR (DMSO-d$_6$) δ169.20, 166.98, 159.78 (d, J=242.49), 140.25, 134.07, 131.10, 129.99, 128.55 (d, J=7.6), 125.21(d, J=3.02), 123.08, 121.93 (d, J=16.80), 119.86, 116.67, 115.62 (d, J=21.42), 37.01; MS (EI, m/z) 305.1 (M$^+$). HRMS (EI) calcd for C$_{15}$H$_{12}$NO$_3$FS 305.0522, found 305.0732.

Example 16
4-((2-Bromoacetyl)amino)benzoic Acid

A solution of 4-aminobenzoic acid (5.0 g, 0.036 mol) in anhydrous DMF (30 mL) and anhydrous dioxane (30 mL) was cooled to 0° C. in a 250 mL 3-necked flask which was fitted with a constant additional funnel. Bromoacetyl bromide (7.36 g, 3.2 mL, 100 mol %) was added dropwise, keeping the internal temperature between 0° C. and 2° C. After the addition was completed (~30 min), the reaction mixture was stirred overnight at rt. Water (100 mL) was added, and then the light crystalline compound which precipitated was filtered, washed with 5% HBr, washed several times with water (200 mL), and then dried in a vacuum oven for 20 h at 40°–45° C., affording 9.3 g (99%) of the title compound: mp 245°–246.7° C.; $^1$H NMR (DMSO-d$_6$) δ10.6 (s, 1H, NH), 7.91 (d, 2H, J=8.8), 7.69 (d, 2H, J=8.4), 4.10 (s, 2H); $^{13}$C NMR (DMSO-d$_6$) δ168.88, 165.38, 142.62, 130.53, 125.78, 118.62, 30.30; MS (EI, m/z) 257 (M$^+$), 258.9 (M$^+$2$^+$). HRMS (EI) calcd for C$_9$H$_8$NO$_3$Br 256.9686, found 256.9677. Anal. Calcd. for C$_9$H$_8$NO$_3$Br: C, 41.88; H, 3.12; N, 5.43. Found: C, 41.97; H, 3.19; N, 5.42.

Example 17
4-(2-(((2-Fluorophenyl)amino)acetyl)amino)benzoic Acid (Compound AP)

A solution of 4-((2-bromoacetyl)amino)benzoic acid from Example 16 (1 g, 3.9 mmol) and o-fluoroaniline (0.86 g, 0.75 mL, 200 mol %) in anhydrous DMF (15 mL) was heated at 80°–85° C. for 7 h. The reaction mixture was poured into ice water, made basic to pH 9 with 5% KOH, and then extracted with CH$_2$Cl$_2$ (3×50 mL). The CH$_2$Cl$_2$ layers was set aside, and then the water layer was acidified with 5% HCl to pH 5. The light crystalline compound which precipitated was filtered, washed several times with water, air dried for 2 days, and then dried in a vacuum oven overnight at 40°–45° C., giving 0.8 g (72%) of the title compound: mp 225°–227° C.; $^1$H NMR (DMSO-d$_6$) δ12.74 (s, 1H, COOH), 10.31 (s, 1H, NH), 7.89 (d, 2H, J=8.4), 7.72 (d, 2H, J=8.8), 7.07–6.94 (m, 2H), 6.65–6.56 (m, 2H), 5.78 (s, 1H, NH), 3.98 (s, 2H); $^{13}$C NMR (DMSO-d$_6$) δ169.46, 166.87, 150.89 (d, J=237.86), 142.82, 136.34 (d, J=11.47), 130.39, 125.20, 124.74 (d, J=3.00), 118.48, 116.33, 116.26, 114.50, 114.32, 112.14 (d, J=3.72), 46.71; MS (EI, m/z) 288.1 (M$^+$). HRMS (EI) calcd for C$_{15}$H$_{13}$N$_2$O$_3$F 288.0910, found 288.0907. Anal. Calcd. for C$_{15}$H$_{13}$N$_2$O$_3$F.0.5 H$_2$O: C, 60.60; H, 4.74; N, 9.42. Found: C, 60.55; H, 4.27; N, 9.54.

Example 18
2-((2-Bromoacetyl)amino)-5-fluorobenzoic Acid

To a cold (0° C.) solution of 2-amino-5-fluorobenzoic acid (15.0 g, 96.6 mmol) in a mixture of dry DMF (35 mL) and dioxane (35 mL) was added, dropwise, bromoacetylbromide (8.43 mL, 96.6 mmol) at 0° C. over a 40 min period, and then the reaction mixture was allowed to come to room temperature overnight. The reaction mixture was cooled to 0° C., water (300 mL) was added slowly, and then the precipitate which formed was collected and washed with 5% HBr (50 mL) and water. After drying, 25.43 g (95.1%) of the title compound was obtained as a white solid: mp 191.2°–191.8° C.; $^1$H NMR (acetone-$d_6$) δ11.60 (s, 1H), 8.71 (dd, J=5.2, J=9.2, 1H), 7.80 (dd, J=3.2, J=9.6, 1H), 7.48–7.43 (m, 1H), 4.18 (s, 2H); $^{13}$C NMR (acetone-$d_6$) δ168.80, 165.71, 158.37 (d, J=241.9), 138.56, 122.78 (d, J=7.8), 122.70, 122.06 (d, J=21.9), 117.98 (d, J=24.0), 30.45; MS (EI, m/z) 277 (M$^+$). HRMS (EI) calcd for $C_9H_7NO_3FBr$ 274.9593, found 274.9594.

Example 19

2-(2-((Phenylamino)acetyl)amino)-5-fluorobenzoic Acid (Compound AQ)

A solution of 2-((2-bromoacetyl)amino)-5-fluorobenzoic acid from Example 18 (22.36 g, 91 mmol) and aniline (21 mL, 230 mmol) in dry DMF (150 mL) was heated at 85° C. for 5 h. TLC showed that unreacted starting material was left. Additional aniline (5 mL, 52 mmol) was added, and the solution was then heated at 120° C. for 30 h. After cooling, the reaction mixture was poured into ice-water (800 mL), and then aqueous 5% KOH (100 mL) was added to adjust the pH to 10-11. The excess aniline was removed by extraction with $CH_2Cl_2$ (3×400 mL), and then the separated aqueous layer was acidified with aqueous 20% HBr. The precipitate which formed was collected, washed with water, and then dried; yielding 19.64 g (74.6%) of the title compound as white crystals, mp 194°–195° C.; $^1$H NMR (acetone-$d_6$) δ11.87 (s, 1H), 8.88 (dd, J=5.2, J=9.6, 1H), 7.71 (dd, J=3.2, J=9.2, 1H), 7.45–7.39 (m, 1H), 7.14–7.10 (m, 2H), 6.68–6.64 (m, 3H), 3.92 (s, 2H); $^{13}$C NMR (acetone-$d_6$) δ171.30, 168.14, 163.22, 157.97 (d, J=241.3), 148.97, 138.66, 129.82, 122.60 (d, J=7.1), 121.90 (d, J=21.9), 118.63, 117.78 (d, J=24.0), 113.67, 50.07; MS (EI, m/z) 288.1 (M$^+$). HRMS (EI) calcd for $C_{15}H_{13}N_2O_3F$ 288.0910, found 288.0914.

Example 20

2-(2-(((4-Fluorophenyl)amino)acetyl)amino)-5-fluorobenzoic Acid (Compound AR)

A solution of 2-((2-bromoacetyl)amino)-5-fluorobenzoic acid from Example 18 (4.0 g, 14.4 mmol) and p-fluoroaniline (4.1 mL, 43.1 mmol) in dry DMF (25 mL) was heated at 110° C. for 30 h. After cooling, the reaction mixture was poured into ice-water(300 mL) and aqueous 5% KOH (50 mL) was added to adjust the pH to 10-11. The excess of p-fluoroaniline was removed by extraction with chloroform (4×250 mL) and the separated aqueous layer was acidified with 20% HBr. The reaction mixture was extracted with EtOAc (3×300 mL), and the combined ethyl acetate layer was washed with water, dried, concentrated, and then treated with hexane. The precipitate was collected, washed with hexane, and then dried, giving 3.1 g (70.5%) of the title compound as a white solid: mp 196.5°–198° C.; $^1$H NMR (acetone-$d_6$) δ11.87 (s, 1H), 8.88 (dd, J=5.2, J=9.2, 1H), 7.72 (dd, J=3.2, J=9.6, 1H), 7.45–7.39 (m, 1H), 6.95–6.89 (m, 2H), 6.70–6.65 (m, 2H), 3.90 (s, 2H); $^{13}$C NMR (acetone-$d_6$) δ171.06, 168.18, 158.05 (d, J=241.1), 156.88 (d, J=233.4), 145.58, 138.64, 122.68 (d, J=7.6), 122.00, 121.78, 117.81 (d, J=24.4), 116.15 (d, J=22.1), 114.66 (d, J=7.64), 50.53; MS (EI, m/z) 306 (M$^+$).

Example 21

2-(2-(((4-Methylphenyl)amino)acetyl)amino)-5-fluorobenzoic Acid (Compound AS)

A solution of 2-((2-bromoacetyl)amino)-5-fluorobenzoic acid from Example 18 (4.0 g, 14.4 mmol) and p-methylaniline (4.8 g, 42.4 mmol) in dry DMF (25 mL) was heated at 110° C. for 20 h. After cooling, the reaction mixture was poured into ice-water(300 mL) and then aqueous 5% KOH (50 mL) was added to adjust the pH to 10-11. The excess p-methylaniline was removed by extraction with $CH_2Cl_2$ (4×250 mL), and then the separated aqueous layer was acidified with 20% HBr, and extracted with EtOAc (3×250 mL). The combined extract was washed with water, dried, concentrated, and then treated with hexane. The precipitate was collected, washed with hexane, and then dried, yielding 3.15 g (72.2%) of the title compound as a white solid: mp 181°–182° C.; $^1$H NMR (acetone-$d_6$) δ8.89 (dd, J=5.2, J=9.2, 1H), 7.71 (dd, J=3.2, J=9.2, 1H), 7.44–7.38 (m, 1H), 6.96–6.92 (m, 2H), 6.60–6.56 (m, 2H), 3.88 (s, 2H), 2.16 (s, 3H); $^{13}$C NMR (acetone-$d_6$) δ171.49, 168.09, 158.00 (d, J=241.9), 146.73, 138.67, 130.31, 127.49, 122.63 (d, J=6.84), 121.95, 121.73, 117.77 (d, J=24.4), 113.85, 50.46, 20.40; MS (EI, m/z) 302 (M$^+$). HRMS (EI) calcd for $C_{16}H_{15}N_2O_3F$ 302.1065, found 302.1053. Anal. Calcd for $C_{16}H_{15}N_2O_3F$: C, 63.57; H, 5.00; N, 9.27. Found: C, 63.26; H, 4.94; N, 8.94.

Example 22

2-(2-(((4-Chlorophenyl)amino)acetyl)amino)-5-fluorobenzoic Acid (Compound AT)

A solution of 2-((2-bromoacetyl)amino)-5-fluorobenzoic acid from Example 18 (4.0 g, 14.4 mmol) and p-chloroaniline (5.51 g, 43.2 mmol) in dry DMF (25 mL) was heated at 110° C. for 24 h. After cooling, the reaction mixture was poured into ice-water(300 mL) and aqueous 5% KOH (50 mL) was added to adjust pH to 10-11. The excess of p-chloroaniline was removed by extraction with $CH_2Cl_2$ (3×250 mL) and the separated aqueous layer was acidified with 20% HBr. The reaction mixture was extracted with EtOAc (3×250 mL), and then the combined extract was washed with water, dried, concentrated, and then treated with hexane. The precipitate was collected, washed with hexane, and then dried, yielding 3.35 g (72.8%) of the title compound as a white solid: mp 199°–200° C.; $^1$H NMR (acetone-$d_6$) δ11.82 (s, 1H), 8.86 (dd, J=5.2, J=9.6, 1H), 7.72 (dd, J=3.0, J=9.2, 1H), 7.44–7.39 (m, 1H), 7.15-7-11 (m, 2H), 6.71–6.67 (m, 2H), 3.94 (s, 2H); $^{13}$C NMR (acetone-$d_6$) δ170.79, 168.33, 158.05 (d, J=241.1), 147.89, 138.79, 129.64, 122.74, 122.66, 122.61, 121.92 (d, J=22.0), 122.03, 121.81, 117.82 (d, J=24.4), 115.04, 49.95; MS (EI, m/z) 322 (M$^+$). HRMS (EI) calcd for $C_{15}H_{12}N_2O_3FCl$ 322.0521, found 322.0524. Anal. Calcd for $C_{15}H_{12}N_2O_3FCl$: C, 55.82; H, 3.75; N, 8.68. Found: 55.74; H, 3.72; N, 8.47.

Example 23

2-(2-(((2-Fluorophenyl)amino)acetyl)amino)-5-fluorobenzoic Acid (Compound AU)

To a solution of 2-((2-bromoacetyl)amino)-5-fluorobenzoic acid from Example 18 (0.8 g, 2.90 mmol) in 20 mL of DMF was added o-fluoroaniline (0.64 g, 0.6 mL, 200 mol %), and then the mixture was heated to 99°–103° C. for 20 h. After cooling, the mixture was poured into (150 mL), and aqueous 5% KOH was added to adjust the pH to 9. The homogenous solution was extracted with $CH_2Cl_2$ (3×70 mL), the combined $CH_2Cl_2$ extracts were set aside, and then the aqueous layer was acidified to pH=3 with 5% HBr. The oily crystalline compound which precipitated was filtered, air-dried, and then dissolved in a small amount of EtOAc. Hexane was added slowly to crystallize the product. Filtration and drying under high vacuum for 7 h afforded 0.27 g (30%) of the title compound as a white crystalline solid: mp 195°–196.6° C.; $^1$H NMR (DMSO-d$_6$) δ13.89 (bs, 1H, OH), 11.87 (s, 1H, NH), 8.74 (dd, 1H, NH, J=4.8, J=9.2), 7.65 (dd, 1H, J=2.8, J=9.2), 7.52–7.48 (m, 1H), 7.07 (d, 1H, J=8), 7.05 (d, 1H, J=8), 6.95 (t, 1H, J=7.6), 6.64–6.55 (m, 2H), 6.36 (s, 1H), 3.90 (d, 2H, J=4.8); $^{13}$C NMR (DMSO-d$_6$) δ170.17 (C=O), 168.07 (C=O, J=2.3), 156.62 (d, J=241.16), 151.03 (d, J=238), 137.08 (d, J=2.3), 136.00 (d, J=11.47), 124.80 (d, J=9.2), 121.46 (d, J=6.94), 121.20 (d, J=22), 117.70 (d, J=6.9), 117.00 (d, J=9.86), 116.80 (d, J=6.84), 114.53 (d, J=17.51), 111.85 (d, J=3.12), 48.13; MS (EI, m/z) 306.1 (M$^+$). HRMS (EI) calcd for C$_{15}$H$_{12}$N$_2$O$_3$F$_2$ 306.0816, found 306.0820. Anal. Calcd for C$_{15}$H$_{12}$N$_2$O$_3$F$_2$·0.39 H$_2$O C, 57.51; H, 4.11; N, 8.94. Found: C, 57.47; H, 3.69; N, 8.91. Anal. Calcd for C$_{15}$H$_{12}$N$_2$O$_3$F$_2$·0.29 H$_2$O C, 57.84; H, 4.07; N, 8.99. Found: C, 57.84; H, 3.79; N, 8.79.

Example 24
2-((2-Bromoacetyl)amino)-6-fluorobenzoic Acid

To a solution of 2-amino-6-fluorobenzoic acid (8.0 g, 0.052 mol) in anhydrous DMF (30 mL) and anhydrous dioxane (30 mL) at 0° C. in a 250 mL 3-necked flask fitted with a constant additional funnel was added, dropwise, bromoacetyl bromide (10.4 g, 100 mol%) while keeping the internal temperature between 0° C. and 2° C. After the addition was completed (~30 min), the reaction mixture was stirred at rt overnight. Water (100 mL) was added, and the light crystalline compound which precipitated was filtered, washed sequentially with 5% HBr and water, and then dried in a vacuum oven at 40°–45° C., affording 9.5 g (67%) of the title compound: mp 168.9°–170.3° C.; $^1$H NMR (DMSO-d$_6$) δ13.80 (bs, 1H, OH), 10.60 (s, 1H, NH), 7.69 (d, 1H, J=8.4), 7.54 (dt, 1H, J=8.4, J=10.4), 7.13–7.08 (m, 1H), 4.16 (s, 2H); $^{13}$C NMR (DMSO-d$_6$) δ165.22 (d, J=32.4, C=O), 160.18 (d, J=251), 137.83, 132.69 (d, J=10.0), 118.58, 118.20, 112.18 (d, J=22.9), 30.04; MS (EI, m/z) 275 (M$^+$). HRMS (EI) calcd for C$_9$H$_7$NO$_3$FBr 274.9593, found 274.9595. Anal. Calcd for C$_9$H$_7$NO$_3$FBr: C, 39.16; H, 2.56; N, 5.08. Found: C, 38.96; H, 2.48; N, 5.07.

Example 25
2-(2-((Phenylamino)acetyl)amino)-6-fluorobenzoic Acid (Compound AV)

A solution of 2-((2-bromoacetyl)amino)-6-fluorobenzoic acid from Example 24 (5.0 g, 0.018 mol) and aniline (3.4 mL, 200 mol %) in anhydrous DMF (40 mL) was heated with stirring at 95°–100° C. for 12 h, cooled, and then poured into ice-water (400 mL). The pH of the reaction mixture was adjusted to 9 with 5% KOH (60 mL), and then the reaction mixture was extracted with CH$_2$Cl$_2$ (3×70 mL). The combined CH$_2$Cl$_2$ extracts were set aside and the aqueous layer was acidified with 5% HBr to pH 3. The oil, which was formed, was extracted into EtOAc (3×100 mL), and the combined EtOAc layer was washed with brine, dried, filtered, and then concentrated. Recrystallization from ether gave 2.0 g (38%) of the title compound: mp 135°–138° C. $^1$H NMR (CDCl$_3$) δ11.53 (s, 1H, NH), 8.53 (d, 1H, J=8), 7.53 (d, 1H, J=6), 7.17 (t, 1H, J=7.6), 6.90 (t, 1H, J=9.6), 6.77 (t, 1H, J=6.8), 6.65 (d, 2H, J=7.6), 6.00 (bs, 2H), 3.96 (s, 2H); $^{13}$C NMR (CDCl$_3$) δ170.00 (d, J=177.48), 163.86, 161.28, 146.73, 141.09, 135.20 (d, J=13.6), 129.63, 129.42, 119.29, 116.77, 116.74, 113.32, 111.70, 111.47, 49.77; MS (EI, m/z) 288 (M$^+$). HRMS (EI) calcd for C$_{15}$H$_{13}$N$_2$O$_3$F 288.0910, found 288.0924.

Example 26
2-(2-(((2-Fluorophenyl)amino)acetyl)amino)-6-fluorobenzoic Acid (Compound AW)

A solution of 2-((2-bromoacetyl)amino)-6-fluorobenzoic acid from Example 24 (1.1 g, 4.0 mmol) and o-fluoroaniline (0.88 g, 0.8 mL, 200 mol %) in anhydrous DMF (20 mL) was heated 100°–105° C. for 20–22 h, cooled, and then poured into ice-water (150 mL). The pH of the mixture was adjusted to 9 with 5% KOH (~15 mL), and then the homogenous solution was extracted with CH$_2$Cl$_2$ (3×70 mL). The combined CH$_2$Cl$_2$ extracts were set aside and the aqueous layer was acidified with 5% HBr to pH 3. The crystalline compound which precipitated was filtered and then dried in a vacuum oven at 40°–45° C. for 10 h, giving 0.82 g (67%) of the title compound: mp 193°–195° C.; $^1$H NMR (DMSO-d$_6$) δ13.86 (bs, 1H, OH), 11.11 (s, 1H, NH), 8.24 (d, 1H, NH, J=8.4), 7.56 (dt, 1H, J=6.4, J=8.4), 7.09–6.94 (m, 3H), 6.66–6.57 (m, 2H), 6.24 (s,1H), 3.88 (d, 2H, J=4.4); $^{13}$C NMR (DMSO-d$_6$) δ170.09 (C=O), 166.37 (C=O), 160.91 (d, J=254), 151.04 (d, J=238.1), 139.59 (d, J=3.83), 136.00 (d, J=12.17), 133.65 (d, J=10.66), 124.80 (d, J=3.12), 116.99 (d, J=6.8), 116.42, 114.62 (d, J=18.22), 112.17, 112.15, 111.18 (d, J=22.82), 48.08; MS (EI, m/z) 306.1. HRMS (EI) calcd for C$_{15}$H$_{12}$N$_2$O$_3$F$_2$ 306.0816, found 306.0804.

Example 27
2-((2-Bromoacetyl)amino)-3-chlorobenzoic Acid

A solution of 2-amino-3-chlorobenzoic acid (7.0 g, 0.041 mol) in anhydrous DMF (20 mL) and anhydrous dioxane (20 mL) was cooled to 0° C. in a 250 mL 3-necked flask which was fitted with a magnetic stirring bar and a constant additional funnel. Bromoacetyl bromide was added dropwise over a 27 min period while keeping the internal temperature between 0° C. and 2° C. After the addition was complete, the ice-bath was removed and stirring was continued for 4 h. The reaction mixture was cooled using an ice-bath, water (100 mL) was added, and then the yellow precipitate which formed was filtered. The filtered solid was washed with water and then dried in a vacuum oven for 2 days, yielding 7.7 g (65%) of the title compound as a light yellow crystals: mp 173°–175° C.; $^1$H NMR (CD$_3$OD) δ7.88 (dd, 1H, J=1.6, J=6), 7.68 (dd, 1H, J=1.2, J=6.8), 7.39 (t, 1H, J=8), 6.6 (bs, 1H, NH), 4.06 (s, 2H); $^{13}$C NMR (CD$_3$OD) δ176.57, 168.38, 134.84, 134.40, 131.95, 130.53, 129.15, 129.05, 28.66; MS (EI, m/z) 293 (M$^+$).

Example 28
2-(2-((Phenylamino)acetyl)amino)-3-chlorobenzoic Acid (Compound AX)

A solution of 2-((2-bromoacetyl)amino)-3-chlorobenzoic acid from Example 27 (7.5 g, 0.026 mol), and aniline (5.8 mL, 250 mol %) in anhydrous DMF (60 mL) was heated to 95°–100° C. for 20 h, cooled, and then stirred for 4 h at rt. The reaction mixture was poured into ice-water (400 mL) and the precipitated product was solubilized by adding aqueous 5% KOH (60 mL). The milky homogenous solution was extracted with CH$_2$Cl$_2$ (3×70 mL). The combined CH$_2$Cl$_2$ extracts were set aside and the aqueous layer was acidified with aqueous 5% HBr to pH 3. The oil which was formed was extracted into EtOAc (3×100 mL), and then the combined extract was washed with brine, dried, filtered, and then concentrated. Recrystallization from ether gave 3.0 g (38%) of the title compound as a white crystals: mp 184°–185° C.; $^1$H NMR (CD$_3$OD) δ7.85 (dd, 1H, J=1.6, J=6), 7.66 (dd, 1H, J=1.6, J=6.4), 7.33 (t, 1H, J=8), 7.16 (t, 2H, J=7.2), 6.72 (dd, 3H, J=2, J=5.6), 3.91 (s, 2H); $^{13}$C NMR (CD$_3$OD) δ203.86, 196.95, 173.19, 173.17, 168.69, 149.44, 134.30, 130.41, 130.09, 128.42, 119.31, 114.44; MS (EI, m/z) 304 (M⁺). HRMS (EI) calcd for $C_{15}H_{13}N_2O_3Cl$ 304.0615, found 304.0613.

Example 29
2-((2-Bromoacetyl)amino)-4-chlorobenzoic Acid

A solution of 2-amino-4-chlorobenzoic acid (10 g, 0.06 mol) in anhydrous DMF (30 mL) and anhydrous dioxane (30 mL) was cooled to 0° C. in a 300 mL 3-necked flask fitted with a magnetic stirring bar and a constant additional funnel. Bromoacetyl bromide was added dropwise over a 2 h period while maintaining the internal temperature between 0°–2° C. After the addition was completed, the ice-water bath was removed, and then the reaction mixture was stirred 20 h. The reaction mixture was cooled in an ice-bath, water (300 mL) was slowly added, and then the white crystalline product which formed was filtered. Recrystallization from EtOAc/hexane gave 9.2 g (54%) of the title compound as a white solid: mp 156.4°–158° C.; ¹H NMR (DMSO-d₆) δ13.99 (s, 1H, NH), 11.72 (s, 1H, COOH), 8.54 (d, 1H, J=2.0), 8.00 (d, 1H, J=8.8), 7.27 (dd, 1H, J=2.4, J=6.4), 4.28 (s, 2H); ¹³C NMR (DMSO-d₆) δ168.60, 165.54, 141.12, 138.51, 133.88, 123.36, 119.23, 115.58, 30.54; MS (EI, m/z) 293 (M⁺).

Example 30
2-(2-((Phenylamino)acetyl)amino)-4-chlorobenzoic Acid (Compound AY)

A solution of 2-((2-bromoacetyl)amino)-4-chlorobenzoic acid from Example 29 (6.5 g, 0.02 mol) and aniline (5.2 mL, 250 mol %) in anhydrous DMF (50 mL) was heated to 100°–105° C. for 4 h and then stirred at rt for 20 h. The reaction mixture was poured into ice-water (400 mL) and the precipitated product was solubilized by adding aqueous 5% KOH (60 mL). The milky homogenous solution was extracted with CH₂Cl₂ (3×100 mL). The combined CH₂Cl₂ extracts were set aside and the aqueous layer was acidified with aqueous 5% HBr to pH=3. The oil which formed was extracted into EtOAc (3×100 mL), and then the combined extract was washed with brine, dried, filtered, and then concentrated. Trituration with ether gave 4.5 g (66%) of the crude title compound as light-beige crystals: mp 177.8°–180° C. The above compound (4.5 g) was stirred with EtOAc (~100 mL) and the insoluble portion was filtered off. The filtrate was concentrated to a light-beige solid which was refluxed with benzene (80 mL) for 40 min. The mixture was filtered while hot and the solid obtained was dried for 4 h under high vacuum, yielding 2.75 g (40%) of the title compound as light crystals: mp 229°–230° C. (became "wet" at 227° C.); ¹H NMR (DMSO-d₆) δ13.6 (bs, 1H), 12.11 (s, 1H), 8.82 (d, J=1.6, 1H), 7.93 (d, J=8.8, 1H), 720 (dd, J=6.0, J=2.6, 1H), 7.10 (t, J=7.6, 2H) 6.63–6.58 (m, 4H), 3.85 (s, 2H); ¹³C NMR (DMSO-d₆) δ171.48, 168.31, 148.01, 141.53, 138.58, 132.86, 128.97, 128.30, 122.61, 118.72, 118.67, 117.16, 114.68, 112.45, 48.89; MS (EI, m/z) 304 (M⁺).

Example 31
2-(2-(((2-Fluorophenyl)amino)acetyl)amino)-4-chlorobenzoic Acid (Compound AZ)

A solution of 2-((2-bromoacetyl)amino)-4-chlorobenzoic acid from Example 29 (0.5 g, 1.7 mmol) and o-fluoroaniline (0.38 g, 350 mL, 200 mol %) in anhydrous DMF (15 mL) was heated to 100° C. for 25 h. After cooling to rt, the reaction mixture was poured into ice-water, and then the precipitated solid was solubilized by adding 5% KOH to adjust the pH to 9. The solution was extracted with CH₂Cl₂ (3×70 mL), the combined CH₂Cl₂ extracts were set aside, and then the aqueous layer was acidified with 5% HBr to pH=3. The oily crystalline compound which formed was filtered, washed with ether, and then dried under high vacuum, providing 0.32 g (58%) of the title compound: mp 173°–175° C. (becoming "wet" at 169° C.); ¹H NMR (DMSO-d₆) δ13.80 (bs, 1H, OH), 12.10 (s, 1H, NH), 8.82 (d, 1H, NH, J=2), 7.93 (d, 1H, J=8.8), 7.22 (dd, 1H, J=2, J=8.8), 7.08–7.03 (m, 1H), 6.94 (t, 1H, J=7.6), 6.64–6.56 (m, 2H), 6.38 (s, 1H), 3.92 (d, 2H, J=6); ¹³C NMR (DMSO-d₆) δ170.90 (C=O), 168.52 (C=O), 162.29, 151.04 (d, J=238.8), 140.10 (d, J=291.38), 135.90 (d, J=11.47), 132.87, 124.80 (d, J=3), 122.68, 118.68, 116.97 (d, J=6.84), 114.62 (d, J=2.3), 114.46, 111.87 (d, J=3.7), 48.20; MS (EI, m/z) 322 (M⁺). HRMS (EI) calcd for $C_{15}H_{12}N_2O_3ClF$ 322.0521, found 322.0510.

Example 32
2-((2-Bromoacetyl)amino)-5-chlorobenzoic Acid

A solution of 2-amino-5-chlorobenzoic acid (10 g, 0.06 mol) in the mixture of anhydrous DMF (30 mL) and dioxane (30 mL) was cooled to 0° C. in a 250 mL 3-necked flask which was fitted with a magnetic stirrer, thermometer and an additional funnel. Bromoacetyl bromide (11.8 g, 5 mL, 100 mol %) was added dropwise over a 20 min period, keeping the internal temperature between 0° C. to 1° C. After the addition was completed, the ice-bath was removed, and then stirring was continued overnight at rt. The reaction mixture was cooled in an ice-bath and stirred for 30 min, water (80 mL) was added, and then the light yellow precipitate which formed was filtered, washed with water, and then dried in a vacuum oven (20 h, 40°–45° C.) affording 11.4 g (67%) of the title compound: mp 210°–212° C. (dec.), ¹H NMR (CD₃OD) δ8.58 (d, 1H, J=9.2), 8.03 (d, 1H, J=2.8), 7.55 (dd, 1H, J=2.4, J=6.4), 4.11 (s, 2H); ¹³C NMR (CD₃OD) δ196.94, 169.69, 140.49, 134.86, 131.94, 129.49, 122.87, 119.47, 30.04; MS (EI, m/z) 293 (M⁺).

Example 33
2-(2-((Phenylamino)acetyl)amino)-5-chlorobenzoic acid (Compound BA)

A solution of 2-((2-bromoacetyl)amino)-5-chlorobenzoic acid from Example 32 (10 g, 0.03 mol) and aniline (8.0 g, 7.8 mL, 250 mol %) in DMF (60 mL) was heated at 100°–110° C. for 4 h. The reaction mixture was poured into ice-water (200 mL), the solid product which formed was solubilized by adding 5% KOH (40 mL), and then the mixture was extracted with CH₂Cl₂ (3×100 mL). The combined CH₂Cl₂ extracts were set aside, and then the aqueous layer was acidified with 5% HBr to pH=3 and extracted with EtOAc (3×200 mL). The combined EtOAc layer was dried (Na₂SO₄), filtered, and then concentrated to give, after drying under vacuum, 7.8 g (75%) of the title compound as a white solid: mp 210°–212° C.; ¹H NMR (DMSO-d₆) δ13.99 (s, 1H, NH), 11.96 (s, 1H, COOH), 8.75 (d, 1H, J=8), 7.87 (d, 1H, J=2.8), 7.68 (d, 1H, J=2.4), 7.65 (d, 1H, J=2.8), 7.10 (t, 2H, J=7.6), 6.61 (m, 4H), 3.84 (s, 2H), ¹³C NMR (DMSO-d₆) δ171.08, 167.81, 148.05, 139.36, 133.81, 130.25, 128.97, 126.20, 121.25, 117.77, 117.14, 112.45, 48.90; MS (EI, m/z) 304 (M⁺). HRMS (EI) calcd for $C_{15}H_{13}N_2O_3Cl$ 304.0615, found 304.0617.

Example 34
2-(2-(((2-Fluorophenyl)amino)acetyl)amino)-5-chlorobenzoic Acid (Compound BB)

A solution of 2-((2-bromoacetyl)amino)-5-chlorobenzoic acid from Example 32 (1.2 g, 4.1 mmol) and o-fluoroaniline (0.9 g, 0.8 mL, 200 mol %) in anhydrous DMF (20 mL) was heated at 100°–105° C. for 18 h. After cooling to rt, the reaction mixture was poured into ice-water (100 mL). Aqueous 5% KOH (15 mL) was added to adjust the pH of the mixture to 9, and then the homogenous solution was extracted with $CH_2Cl_2$ (3×50 mL). The combined $CH_2Cl_2$ extracts were set aside and the aqueous layer was acidified with 5% HBr to pH=3. The light crystalline compound which formed was filtered and then dried in a vacuum oven for 17 h at 40°–45° C., affording 0.7 g (53%) of the title compound: mp 223°–225° C.; $^1$H NMR (DMSO-$d_6$) δ13.99 (bs, 1H, OH), 11.96 (s, 1H, NH), 8.74 (d, 1H, NH, J=8.8), 7.87 (d, 1H, J=2.4), 7.68 (dd, 1H, J=2.4, J=8.8), 7.05 (dq, 1H, J=1.2, J=6.8), 6.94 (t, 1H, J=7.6), 6.64–6.55 (m, 2H), 6.37 (s, 1H), 3.90 (d, 2H, J=5.6 Hz); $^{13}$C NMR (DMSO-$d_6$) δ170.50 (s, C=O), 167.99 (s, C=O), 151.05 (d, J=238.55), 139.34, 135.99, 135.87, 132.06 (d, J=361.80), 126.28, 124.80 (d, J=2.82), 121.22, 117.72, 116.95 (d, J=7.14), 114.55 (d, J=18.41), 111.88 (d, J=2.8), 48.20; MS (EI, m/z) 322.1 (M$^+$). HRMS (EI) calcd for $C_{15}H_{12}N_2O_3ClF$ 322.0521 found 322.0510

Example 35
2-((2-Bromoacetyl)amino)-6-chlorobenzoic Acid

A solution of 2-amino-6-chlorobenzoic acid (10.0 g, 0.06 mol) in anhydrous DMF (30 mL) and anhydrous dioxane (30 mL) was cooled to 0° C. in 300 mL 3-necked flask fitted with a magnetic stirring bar and constant additional funnel. Bromoacetyl bromide was added dropwise over a 20–25 min period, while maintaining the internal temperature between 0° C. to 1° C. After the addition was completed, the ice-bath was removed and stirring was continued for 20 h. The reaction mixture was cooled in an ice-bath, water (150 mL) was added, and then the yellow crystalline product which formed was filtered and washed sequentially with 5% HBr solution (50 mL) and water (50 mL). After drying in a vacuum oven (20 h, 40°–45° C.), 5.0 g (30%) of the title compound was obtained: mp 133°–135° C. (dec.); $^1$H NMR (CD$_3$OD) δ7.70 (d, 1H, J=8), 7.43 (t, 1H, J=8.4), 7.35 (d, 1H, J=8), 4.05 (s, 2H); $^{13}$C NMR (CD$_3$OD) δ168.19, 167.84, 137.24, 133.31, 132.85, 132.08, 128.78, 128.21, 124.20, 29.21; MS (EI, m/z) 293 (M$^+$)

Example 36
2-(2-((phenylamino)acetyl)amino)-6-chlorobenzoic Acid (Compound BC)

A solution of 2-((2-bromoacetyl)amino)-6-chlorobenzoic acid from Example 35 (7.0 g, 0.024 mol) and aniline (5.6 g, 6 mL, 250 mol %) in DMF (40 mL) was heated at 100° C. for 5 h. The reaction mixture was cooled to rt, poured onto ice, and then the crystalline product which formed was solubilized by adding 5% KOH (70 mL, pH=9). The milky homogenous solution was extracted with $CH_2Cl_2$ (3×100 mL), the combined $CH_2Cl_2$ extracts were set aside, and then the aqueous layer was acidified to pH=3 with 5% HBr and extracted with EtOAc (4×100 mL). The combined EtOAc layer was dried and then concentrated. Recrystallization from EtOAc/hexane gave 6 g (82%) of the title compound as white crystals: 176°–178.2° C.; $^1$H NMR (DMSO-$d_6$) δ9.93 (s, 1H, COOH), 7.97 (d, 1H, J=8), 7.42 (t, 1H, J=8), 7.30 (d, 1H, J=7.6), 7.12 (t, 2H, J=7.2), 6.65 (t, 3H, J=7.2), 3.82 (s, 2H); $^{13}$C NMR (DMSO-$d_6$) δ170.19, 166.30, 148.15, 136.56, 131.12, 130.53, 128.98, 125.51, 121.39, 119.12, 117.23, 112.71, 48.13; MS (EI, m/z) 304 (M$^+$).

Example 37
2-((2-Bromoacetyl)amino)-5-methoxybenzoic Acid

To a solution of 2-amino-5-methoxybenzoic acid (5.0 g, 0.03 mol) in anhydrous DMF (30 mL) and dioxane (30 mL) was added, dropwise, bromoacetyl bromide (6.0 g, 2.6 mL, 100 mol %) while keeping the internal temperature between 0° and 2° C. After the addition was completed (~30 min), the reaction mixture was stirred overnight at rt. The reaction mixture was diluted with water (100 mL), and then the precipitated product was filtered, washed sequentially with 5% HBr (300 mL) and water (300 mL), and then dried in a vacuum oven at 40°–45° C., affording 5.6 g (65%) of the title compound as a light grey solid: mp 171.5°–172.7° C.; $^1$H NMR (DMSO-$d_6$) δ11.26 (s, 1H, NH), 8.30 (d, 1H, J=9.2), 7.44 (d, 1H, J=3.2), 7.22 (dd, 1H, J=3.2, J=9.2), 4.22 (s, 2H), 3.78 (s, 3H); $^{13}$C NMR (DMSO-$d_6$) δ168.69, 164.52, 154.75, 133.03, 122.13, 119.83, 119.04, 114.87, 55.40, 30.59; MS (EI, m/z)287 (M$^+$). HRMS (EI) calcd for $C_{10}H_{10}NO_4Br$ 286.9793, found 286.9793.

Example 38
2-(2-((phenylamino)acetyl)amino)-5-methoxybenzoic Acid (Compound BD)

A solution of 2-((2-bromoacetyl)amino)-5-methoxybenzoic acid from Example 37 (2.80 g, 9.8 mmol) and aniline (2.22 mL, 250 mol %) in anhydrous DMF (30 mL) was heated at 80°–85° C. for 5 h, and then stirred at rt for 20 h. The reaction mixture was poured into ice-water (400 mL), 5% KOH solution (60 mL) was added, and then the milky homogenous solution was extracted with $CH_2Cl_2$ (200 mL, 2×100 mL). The combined $CH_2Cl_2$ extracts were set aside and the aqueous layer was acidified with 5% HBr to pH=3. The precipitate which formed was filtered, washed sequentially with 5% HBr solution (30 mL) and water (30 mL), and then dissolved in EtOAc. The EtOAc extract was washed with brine, dried, filtered, and then concentrated to afford, after drying under high vacuum overnight, 2.0 g (68%) of the title compound: mp 217°–218° C.; $^1$H NMR (CD$_3$OD) δ8.6 (d, 1H, J=5.6), 8.25 (s, 1H), 7.60 (m, 3H), 6.78 (m, 3H), 3.87 (s, 2H), 3.80 (s, 3H). $^{13}$C NMR (CD$_3$OD) δ205.89, 187.53, 185.11, 178.48, 173.05, 169.28, 142.03, 134.91, 130.06, 122.99, 120.82, 119.07, 116.41, 113.99, 55.98, 50.45; MS (EI, m/z) 300 (M$^+$). HRMS (EI) calcd for $C_{16}H_{16}N_2O_4$ 300.1110, found 300.1089.

Example 39
2-(2-(((2-Fluorophenyl)amino)acetyl)amino)-5-methoxybenzoic Acid (Compound BE)

A solution of 2-((2-bromoacetyl)amino)-5-methoxybenzoic acid from Example 37 (3.0 g, 0.01 mol) and o-fluoroaniline (3.16 g, 2.7 mL, 200 mol %) in anhydrous DMF (30 mL) was heated at 100° C. for 20 h. After cooling to rt, the reaction mixture was poured into ice-water (250 mL), 5% KOH (20 mL) was added to adjust the pH to 9, and then the homogenous solution was extracted with $CH_2Cl_2$ (3×70 mL). The combined $CH_2Cl_2$ extracts were set aside and the aqueous layer was acidified to pH=3 with 5% HBr. The yellow crystalline compound which formed was filtered and then dried in a vacuum oven overnight at 40°–45° C., affording 2.6 g (79%) of the title compound: mp 226°–227.1° C.; $^1$H NMR (DMSO-$d_6$) δ13.60 (bs, 1H, OH), 11.73 (s, 1H, NH), 8.63 (d, 1H, NH, J=9.6), 7.40 (d, 1H, J=3.2), 7.20 (dd, 1H, J=3.2, J=9.2), 7.06 (dd, 1H, J=1.2, J=8), 7.02 (dd, 1H, J=1.2, J=8), 6.96–6.92 (m, 1H), 6.63–6.55 (m, 1H), 6.34 (s, 1H), 3.88 (d, 2H, J=5.2), 3.76 (t, 3H, J=3.6); $^{13}$C NMR (DMSO-$d_6$) δ169.57 (C=O), 168.81 (C=O), 153.13 (J=187.6), 149.83, 136.00 (J=11.50), 134.06, 124.76 (J=3.12), 120.64 (J=99.51), 117.22, 116.75 (J=6), 114.75, 114.58, 114.40, 111.83 (J=3.7), 55.35, 48.11; MS (EI, m/z)318 (M$^+$) HRMS (EI) calcd for $C_{16}H_{15}N_2O_4F$ 318.1016, found 318.1008.

Example 40

2-((2-Bromoacetyl)amino)-5-bromobenzoic Acid

To a solution of 2-amino-5-bromobenzoic acid (11.2 g, 0.052 mol) in anhydrous DMF (40 mL) and anhydrous dioxane (40 mL) was added, dropwise, bromoacetyl bromide while keeping the internal temperature between 0° C. and 5° C. After the addition was completed (~25 min), the ice-bath was removed and the mixture was stirred for 20 h at rt. The reaction mixture was cooled in an ice-bath, water was added (100 mL), and then the mixture was poured into ice water. The precipitate which formed was filtered, washed with water, and then dried in a vacuum oven for 20 h at 40°–45° C., affording 9.9 g (57%) of the title compound: mp 203°–204° C.; $^1$H NMR (CDCl$_3$) δ11.67 (s, 1H, NH), 8.64 (d, 1H, J=8.8), 8.55 (d, 1H, J=2.4), 7.71 (dd, 1H, J=2, J=6.8), 3.72 (s, 2H ); $^{13}$C NMR (CDCl$_3$): 200.55, 138.06, 134.22, 134.20, 122.06, 107.46, 67.08; MS (EI, m/z) 337 (M$^+$). HRMS (EI) calcd for C$_9$H$_7$NO$_3$Br$_2$ 334.8792, found 334.8791.

Example 41

2-(2-((Phenylamino)acetyl)amino)-5-bromobenzoic Acid (Compound BF)

A solution of 2-((2-bromoacetyl)amino)-5-bromobenzoic acid from Example 40, aniline (2.4 g, 200 mol %), and DMAP (0.08 g, 5 mol %) in anhydrous DMF (30 mL) was heated at 98° C. for 5 h. After cooling, the reaction mixture was poured into ice-water. 5% KOH was added to adjust the pH to 9, and then the mixture was extracted with CH$_2$Cl$_2$ (3×100 mL). The CH$_2$Cl$_2$ layer was set aside and the water layer was acidified with 10% HBr to pH 3. This mixture was extracted with EtOAc (3×100 mL), and then the combined EtOAc layer was sequentially washed with brine and water, dried, filtered, and then concentrated. Benzene (100 mL) was added, the mixture was refluxed for 30 min and cooled to rt, and then hexane was added. The crystallized product was filtered and dried under vacuum to afford 3.3 g (74%) of a compound having a mp of 176°–178.4° C. This compound was triturated with Et$_2$O and then dried under vacuum, giving 2.89 g (65%) of the title compound as a white crystalline solid: mp 192°–194° C.; $^1$H NMR (DMSO-d$_6$) δ13.8 (bs, 1H, OH), 11.96 (s, 1H, NH), 8.69 (d, 1H, J=8.8, NH), 8.01 (d, 1H, J=2.4), 7.78 (dd, 1H, J=2.4, J=6.8), 7.10 (dd, 2H, J=7.6, J=0.8), 6.63–6.57 (m, 4H), 2.73 (s, 2H); $^{13}$C NMR (DMSO-d$_6$) δ171.09, 167.70, 162.29, 148.04, 139.73, 136.70, 133.14, 128.96, 128.30, 121.53, 118.06, 117.14, 113.98, 112.45, 48.91; MS (EI, m/z)348 (M$^+$), 350 (M+2$^+$). HRMS (EI) calcd for C$_{15}$H$_{13}$N$_2$O$_3$Br 348.0109 found 348.0101. Anal. Calcd. for C$_{15}$H$_{13}$N$_2$O$_3$Br : C, 51.59; H, 3.75; N, 8.02. Found: C, 51.27; H, 3.62; N, 8.28.

Example 42

2-(2-(((2-Fluorophenyl)amino)acetyl)amino)-5-bromobenzoic Acid (Compound BG)

A solution of 2-((2-bromoacetyl)amino)-5-bromobenzoic acid from Example 40 (2.3 g, 6.8 mmol) and o-fluoroaniline (1.5 g, 1.3 mL, 200 mol %) in anhydrous DMF (20 mL) was heated at 100° C. for 30 h. After cooling, the reaction mixture was poured into ice-water (250 mL), and then 5% KOH (15–17 mL) was added to adjust the pH to 9 and solubilize the mixture. The solution was extracted with CH$_2$Cl$_2$ (3×70 mL), the combined CH$_2$Cl$_2$ extracts were set aside, and then the aqueous layer was acidified with 5% HBr to pH 3. The crystalline compound which formed was filtered, air-dried overnight, and then dried under high vacuum for 10 h, affording 1.7 g (68%) of the title compound: mp 224.6°–226.2° C.; $^1$H NMR (DMSO-d$_6$) δ13.94 (bs, 1H, OH), 11.95 (s, 1H, NH), 8.68 (d, 1H, NH, J=8.8), 8.00 (d, 1H, J=2), 7.78 (dd, 1H, J=2.4, J=9.2), 7.06 (d, 1H, J=8), 7.03 (d, 1H, J=8), 6.94 (t, 1H, J=7.6), 6.63–6.56 (m, 1H), 6.37 (s, 1H), 3.90 (d, 1H, J=4.4); $^{13}$C NMR (DMSO-d$_6$) δ170.50 (C=O),167.88 (C=O), 151.03 (d, J=238.05), 139.70, 136.72, 135.97, 134.56 (d, J=271.55), 124.76 (d, J=3.02), 121.47, 117.98, 116.90 (d, J=6.84), 114.50 (d, J=18.31), 114.04, 111.87 (d, J=3.02), 48.22; MS (EI, m/z) 366 (M$^+$), 368 (M+2$^+$).

Example 43

2-((2-Bromoacetyl)amino)-5-hydroxybenzoic Acid

To a solution of 2-amino-5-hydroxybenzoic acid (6.1 g, 0.04 mol) in anhydrous DMF (20 mL) and anhydrous dioxane (20 mL) was added, dropwise, bromoacetyl bromide (8.0 g, 3.5 mL, 100 mol %) while keeping the internal temperature between 0° C. and 5° C. After the addition was completed (~20 min), the ice-bath was removed and the mixture was stirred for 20 h at rt. The reaction mixture was cooled in an ice-bath, water was added (100 mL), and then the mixture was poured into ice-water. The light precipitate which formed was filtered and then dried in a vacuum oven for 20 h at 40°–45° C., giving 7.8 g (72%) of the title compound: mp 213°–215.3° C.; $^1$H NMR (DMSO-d$_6$) δ13.56 (bs, 1H, OH), 11.19 (s, 1H, NH), 9.68 (s, 1H, OH), 8.19 (d, 1H, J=8.8), 7.36 (d, 1H, J=3.2), 7.01 (dd, 1H, J=3.2, J=9.2), 4.19 (s, 2H); $^{13}$C NMR (DMSO-d$_6$) δ168.88, 164.32, 153.08, 131.69, 122.21, 120.79, 119.00, 116.60, 30.66; MS (EI, m/z) 273 (M$^+$), 275 (M+2$^+$). HRMS (EI) calcd for C$_9$H$_8$NO$_4$Br 272.9637, found 272.9634.

Example 44

2-(2-(((2-Fluorophenyl)amino)acetyl)amino)-5-hydroxybenzoic Acid (Compound BH)

To a solution of 2-((2-bromoacetyl)amino)-5-hydroxybenzoic acid from Example 43 (3.1 g, 0.011 mol) and o-fluoroaniline (2.5 g, 2.17 mL, 100 mol %) in anhydrous DMF (30 mL) was heated to 100° C. for 20 h, cooled to rt, and then poured into ice-water (200 mL). The light crystalline compound which precipitated was solubilized by adding 5% KOH to adjust the pH to 9, and then the solution was extracted with CH$_2$Cl$_2$ (3×70 mL). The combined CH$_2$Cl$_2$ extracts were set aside and the aqueous layer was acidified with 5% HBr to pH 3. The crystalline compound which formed was filtered, washed with water, and then dried in a vacuum oven for 17 h at 40°–45° C., affording 1.8 g (53%) of the title compound: mp 213°–215.5° C.; $^1$H NMR (DMSO-d$_6$) δ13.42 (bs, 1H, OH), 11.65 (s, 1H, NH), 9.54 (s, 1H, OH), 8.53 (d, 1H, NH, J=4.8), 7.95 (s, 1H), 7.32 (dd, 1H, J=1.2, J=2.4), 7.07–6.93 (m, 2H), 6.63–6.54 (m, 2H ), 6.36 (s, 1H), 3.85 (d, 2H, J=5.6); $^{13}$C NMR (DMSO-d$_6$) δ169.10 (d, COOH, J=29.68), 162.29 (s, C=O), 152.32, 152.19, 149.81, 136.10 (d, J=11.28), 132.72, 124.74 (d, J=3.3), 121.08, 117.23, 116.74, 116.62 (d, J=24.05), 114.40 (d, J=17.71), 111.81 (d, J=2.8), 48.09; MS (EI, m/z), 304.1 (M$^+$). HRMS (EI) calcd for C$_{15}$H$_{13}$N$_2$O$_4$F 304.0859, found 304.0844.

Example 45

2-(2-(Phenoxyacetyl)amino)benzoic Acid (Compound BI)

To a solution of anthranilic acid (5 g, 0.036 mol) in NaOH (3 g, 30 mL) was added, dropwise, phenoxyacetyl chloride (6.2 g, 5.2 mL) at 0° C. The reaction mixture was stirred at 0° C. for 30 min, the mixture was acidified with dilute HCl, and then the resulting mixture was filtered. The filtered solid was taken up in EtOAc, the mixture was filtered, and then the filtrate was dried over Na$_2$SO$_4$. Following filtration, concentration, and then drying of the product for 4 h under vacuum, 8.0 g (81%) of the title compound was obtained:

mp 201°–203° C. A small amount (100 mg) of the title compound was recrystallized from EtOH, giving 75 mg of the title compound: mp 202°–203° C.; $^1$H NMR (DMSO-d$_6$) δ13.70 (s, 1H, COOH), 12.20 (s, 1H, NH), 8.71 (d, 1H, J=8.4), 8.02 (dd, 1H, J=7.6), 7.65–7.60 (m, 1H), 7.35–6.89 (m, 6H), 4.73 (s, 2H); $^{13}$C NMR (DMSO-d$_6$) δ169.44, 167.23, 157.11, 140.22, 134.34, 131.32, 129.65, 123.06, 121.65, 120.96, 119.45, 116.14, 114.81, 114.38, 67.22; MS (EI, m/z) 271 (M$^+$). HRMS (EI) calcd for C$_{15}$H$_{13}$NO$_4$ 271.0845, found 271.0840. Anal. Calcd. for C$_{15}$H$_{13}$NO$_4$: C, 66.41; H, 4.83; N, 5.16. Found: C, 66.20; H, 4.71; N, 4.91.

Example 46
Phenylmercaptoacetyl Chloride

To thiophenoxyacetic acid (8 g, 0.05 mol) was added SOCl$_2$ (8 mL) and the reaction mixture was heated to reflux for 1 h. TLC showed disappearance of the starting material. The excess SOCl$_2$ was removed in vacuo (hood!) and the product distilled to give 8.6 g (98%) of the title compound: bp 85°–86° C., 4–5 Torr (lit. 117°–119° C., 6 Torr (Mooradian, A.; Cavallito, C. J.; Bergman, A. J.; Lawson, E. J.; Suter, C. M. *J. Am. Chem. Soc.* 1949, 3372)); $^1$H NMR (CDCl$_3$) δ7.48–7.34 (m, 5H), 4.06 (m, 2H); $^{13}$C NMR (CDCl$_3$) δ169.75, 132.83, 131.44, 129.35, 128.22, 48.48; MS (EI, m/z) 186 (M$^+$).

Example 47
2-((2-(Phenylthio)acetyl)amino)benzoic Acid (Compound BJ)

To a solution of 6.3 g of anthranilic acid in aqueous NaOH (4 g of NaOH in 40 mL of water) which was cooled using an ice-bath was added 8.6 g (0.046 mol) of phenylmercaptoacetylchloride from Example 46. The reaction mixture was stirred for 1 h. The reaction mixture was neutralized with 5% HCl, water (50 mL) was added, and then the mixture was extracted with EtOAc (3×100 mL). The EtOAc solution was dried, filtered, and then concentrated to give after drying under high vacuum, 7.0 g (53%) of the title compound, mp 166°–167° C. (lit. 164°–166° C. (Gorlitzer, K.; Weber, J. *Arch. Pharm. (Weinheim)* 1980, 314, 76)); $^1$H NMR (DMSO-d$_6$) δ11.82 (s, 1H, COOH), 8.51 (s, 1H, J=8.4),7.96 (dd, 1H, J=1.2, J=8), 7.58 (t, 1H, J=8), 7.38 (d,1H, J=7.2), 7.13 (m, 5H), 4.01 (s, 2H); $^{13}$C NMR (DMSO-d$_6$) δ169.17, 167.42, 140.31, 135.00, 134.07, 133.72, 131.12, 129.18, 128.07, 126.33, 123.01, 119.77, 116.58, 116.31, 114.54; MS (EI, m/z) 287 (M$^+$). HRMS (EI) calcd for C$_{15}$H$_{13}$N$_2$O$_3$S 287.0616, found 287.0617.

Example 48
Benzyl 2-((2-Fluorophenyl)amino)acetate

The procedure of Zahler et al. was followed with minor modification (Zahler, R.; Koster, W. H.; Slusarchyk, W. A. EP 0138407). To a solution of benzyl bromoacetate (18.0 g, 12.5 mL, 79.6 mmol) and o-fluoroaniline (8.8 g, 7.7 mL, 100 mol %), in anhydrous DMF (60 mL) was added anhydrous K$_2$CO$_3$ (11 g, 100 mol %), and the mixture was stirred at rt overnight. The reaction mixture was diluted with water (120 mL) and extracted with EtOAc (3×200 mL). The combined organic layer was washed with water, dried, and then concentrated. Purification by LPLC (5% EtOAc- hexane) provided 18.0 g (88%) of the title compound as a colorless oil: $^1$H NMR (CDCl$_3$) δ7.39–7.35 (m, 5H), 7.03–6.97 (m, 2H), 6.72–6.67 (m, 1H), 6.59 (dt, J=8.4, J=1.2, 1H), 5.23 (s, 2H), 4.01 (s, 2H); $^{13}$C (CDCl$_3$) δ170.59, 151.66 (d, J=240), 135.24, 128.64 (2 carbons), 128.52, 128.39 (2 carbons), 124.55 (d, J=3.5), 117.79 (d, J=7.1), 114.71 (d, J=17.7), 112.28 (d, J=3.5), 67.11, 45.54; MS (EI, m/z)259 (M$^+$).

Example 49
2-((2-Fluorophenyl)amino)acetic Acid (Compound BK)

To a suspension of 10% Pd/C (200 mg) in reagent grade methanol (25 mL) which was degassed was added a solution of benzyl 2-((2-fluorophenyl)amino)acetate from Example 48 (2.0 g, 7.71 mmol) in methanol (10+5 mL). The solution was degassed, a balloon of hydrogen gas was added, and then the reaction mixture was stirred for 8 h at rt. The reaction mixture was filtered though celite and then concentrated to yield 1.27 g (97%) of the title compound as a white solid: mp 125.7°–126.6° C. (lit. 122°–123° C. (Walls, L. P. South African patent application 664864; Walls, L. P. GB 1,153,884); $^1$H NMR (CDCl$_3$) δ7.06–6.99 (m, 2H), 6.77–6.70 (m, 1H), 6.33 (dt, J=8.8, J=1.2, 1H), 4.04 (s, 2H); $^{13}$C NMR (CDCl$_3$) δ175.79, 151.71 (d, J=239); 135.01, 124.65 (d, J=3.5), 118.38 (d, J=6.4), 114.85 (d, J=18.4), 112.45, 45.30; MS (EI, m/z) 169 (M+). HRMS (EI) calcd for C$_8$H$_8$NO$_2$F 169.0539, found 169.0538.

Example 50
Methyl 2-((2-Bromoacetyl)amino)benzoate

A solution of methyl anthranilate (5 g, 0.033 mol) in anhydrous DMF (25 mL) and anhydrous dioxane (25 mL) was cooled to 0° C. in a 250 mL 3-necked flask, fitted with a magnetic stirrer and a constant addition funnel. Bromoacetyl bromide (6.7 g, 2.9 mL, 100 mol %) was added dropwise, keeping the internal temperature between 0° C. and 2° C. After the addition was complete (20–25 min), the reaction mixture was stirred at rt overnight. The reaction mixture was diluted with water (100 mL) and the white crystalline compound which precipitated was filtered, washed sequentially with 5% HBr (100 mL) and water (200 mL), and then dried in a vacuum oven at 40°–45° C. overnight. The product was triturated with ether and then dried in vacuo for 5 h, yielding 7.9 g (88%) of the title compound as a white solid: mp 81°–82° C.; $^1$H NMR (DMSO-d$_6$) δ11.07 (s, 1H, NH), 8.23 (dd, 1H, J=1.2, J=8.4), 7.94 (dd, 1H, J=1.6, J=8), 7.66–7.62 (m, 1H), 7.27–7.23 (m,1H), 4.23 (s, 2H), 3.87 (s, 3H); $^{13}$C NMR (DMSO-d$_6$) δ171.64, 167.28, 138.81, 134.03, 130.67, 124.02, 122.90, 121.22, 52.51, 30.37; MS (EI, m/z) 271 (M$^+$), 273 (M+2$^+$). HRMS (EI) calcd for C$_{10}$H$_{10}$NO$_3$Br 270.9844, found 270.9838. Anal. Calcd for C$_{10}$H$_{10}$NO$_3$Br: C, 44.14; H, 3.70; N, 5.15. Found: C, 44.18; H, 3.67; N, 4.94.

Example 51
Methyl 2-(2-(((2-Fluorophenyl)amino)acetyl)amino) benzoate (Compound BL)

A solution of methyl 2-((2-bromoacetyl)amino)benzoate from Example 50 (2.1 g, 7.72 mmol) and o-fluoroaniline (1.71 g, 1.5 mL, 200 mol %) in anhydrous DMF (20 mL) was heated at 85°–90° C. for 15 h, cooled to 40° C., and then poured into ice-water (100 mL). The pH of the mixture was adjusted to 9 with 5% KOH, the mixture was extracted with CH$_2$Cl$_2$ (3×70 mL), and then the organic layer was set aside. The separated water layer was acidified with 5% HCl to pH 5, extracted with EtOAc (3×60 mL), and then the combined EtOAc layer was dried, filtered, and then concentrated. The product was triturated several times with ether to afford, after drying in vacuo, 0.9 g (39%) of the title compound: mp 92°–94° C.; $^1$H NMR (DMSO-d$_6$) δ11.37 (s, 1H, NH), 8.58 (d, 1H J=8.4), 7.90 (dd, 1H, J=1.2, J=8), 7.61 (d, 1H, J=7.2), 7.19–7.06 (m, 2H), 6.96 (t, 1H, J=7.6), 6.65–6.57 (m, 2H), 6.36 (t, 1H, J=5.2), 3.91 (d, 2H, J=6), 3.72 (s, 3H); $^{13}$C NMR (DMSO-d$_6$) δ170.10, 167.05, 151.14 (d, J=238.57), 139.53, 136.01 (d, J=11.97), 134.25, 130.71 (d, J=8.45), 124.81 (d, J=2.92), 121.63 (d, J=295.90), 117.11 (d, J=6.44), 116.29, 114.63, 114.46, 112.16 (d, J=3.52), 52.27, 48.32; MS (EI, m/z) 302 (M⁺). HRMS (EI) calcd for $C_{16}H_{15}N_2O_3F$: C, 302.1067, found 302.1072. Anal. Calcd for $C_{16}H_{15}N_2O_3F$: C, 63.57; H, 5.00; N, 9.27. Found: C, 63.41; H, 5.03; N, 9.47.

Example 52
Methyl 2-(2-(((2-Fluorophenyl)amino)acetyl)amino) benzoate (Compound BL)

A solution of methyl 2-((2-bromoacetyl)amino)benzoate from Example 50 (1.0 g, 3.68 mmol) and o-fluoroaniline (0.82 g, 0.7 mL, 200 mol %) in anhydrous DMF (15 mL) was heated at 85°–90° C. for 15 h, cooled to 40° C., and then poured into ice-water (100 mL). The reaction mixture was extracted with EtOAc (3×70 mL), and the combined EtOAc layer was dried and then concentrated. Purification by LPLC (EtOAc-hexane 1:1) afforded a light yellow product which was triturated several times with hexane. After drying in vacuo for 10 h, 0.65 g (59%) of the title compound was obtained as white crystals: mp 92°–94° C.; $^1$H NMR (DMSO-$d_6$) δ11.37 (s, 1H, NH), 8.58 (d, 1H, J=8.4), 7.90 (dd, 1H, J=1.2, J=8), 7.61 (d, 1H, J=7.2), 7.19–7.06 (m, 2H), 6.96 (t, 1H, J=7.6), 6.65–6.57 (m, 2H), 6.36 (t, 1H, J=5.2), 3.91 (d, 2H, J=6), 3.72 (s, 3H); $^{13}$C NMR (DMSO-$d_6$) δ170.10, 167.05, 151.14 (d, J=238.57), 139.53, 136.01 (d, J=11.97), 134.25, 130.71 (d, J=8.45), 124.81 (d, J=2.92), 121.63 (d, J=295.90), 117.11 (d, J=6.44), 116.29, 114.63, 114.46, 112.16 (d, J=3.52), 52.27, 48.32; MS (EI, m/z) 302 (M⁺). HRMS (EI) calcd for $C_{16}H_{15}N_2O_3F$ 302.1067, found 302.1072.

Example 53
1,2-Bis((2-Carboxyphenyl)amino)ethane (Compound BM)

The procedures of Formanovskii (Formanovskii, A. A. *Zh. Org. Khim.* 1986, 22, 1103 and Sandhu and Verma (Sandhu, G. K.; Verma, S. P.; Moore, L. S.; Parish, R. V. *J. Organomet. Chem.* 1986, 315, 309) were followed with some modification. To a stirred suspension of anthranilic acid (4.0 g, 0.029 mol) in water (30 mL) was added KOH (1.64 g, 100 mol %). The solution was heated to reflux, and then 1,2-dibromoethane (5.5 g, 100 mol %) and o-fluoroaniline (3.2 g, 100 mol %) were added. The mixture was refluxed for 5 h and then cooled. Crystals formed from the reaction mixture which were separated, air dried, washed with EtOAc, and then dried in a vacuum oven of 10 h at 40°–45° C., yielding 1.7 g (20%) of the title compound: mp 247.9°–248.1° C. (lit. 235° C. (Formanovskii, A. A. *Zh. Org. Khim.* 1986, 22, 1103)); $^1$H NMR (CDCl₃) δ12.55 (bs, 2H), 8.0 (bs, 2H), 7.93 (dd, 2H, J=8.0, J=1.6), 7.40–7.34 (m, 2H), 6.84 (d, 2H, J=8.4), 6.57 (t, 2H, J=7.6), 3.47 (s, 4H); $^{13}$C NMR (CDCl₃) δ169.87, 150.79, 134.51, 131.71, 114.38, 111.27, 110.14, 41.28; MS (EI, m/z) 300 (M⁺). HRMS (EI) calcd for $C_{16}H_{16}N_2O_4$ 300.1100, found 300.1106.

Example 54
1-((2-Carboxyphenyl)amino)-2-((2-fluorophenyl)amino) ethane (Compound BN)

A solution of anthranilic acid (1.0 g, 7.3 mmol) in 1,2-dibromoethane (3 mL, 300 mol %) was heated to 100° C., and then o-fluoroaniline (2 mL, 200 mol %) was added. The reaction mixture was stirred at 100° C. for 10 h, then stirred at rt for 24 h. The reaction mixture was diluted with water and then extracted with EtOAc (3×100 mL). The EtOAc layer was washed with water, dried over MgSO₄, filtered, and then concentrated. Purification by LPLC (EtOAc-hexane 1:5, then EtOAc-hexane 1:1) gave 0.17 g (9%) of the title compound which contained an impurity. The title compound was dissolved in small amount of hot EtOAc, hexane was added dropwise, and then the solution was allowed to stand at 0° C. until crystallization commenced, and then it was allowed to stand at rt for 15 h. Filtration and then drying in a vacuum oven several hours at 40°–45° C. gave 70 mg (3.5%) of the title compound: $^1$H NMR (CDCl₃) δ8.00 (d, 1H, J=8, NH), 7.42 (t, 2H, J=6.8), 7.05–6.97 (m, 2H), 6.80–6.65 (m, 4H), 3.55 (d, 2H, J=4.8), 3.51 (d, 2H, J=4); $^{13}$C NMR (CDCl₃) δ173.37, 151.72 (d, J=238), 151.38, 135.63, 132.83, 124.60 (d, J=3.8), 117.27 (d, J=6.8), 115.30, 114.73, 114.54, 112.32, 111.33, 109.25, 42.75, 42.12; MS (EI, m/z) 274 (M⁺). HRMS (EI) calcd for $C_{15}H_{15}N_2O_2F$ 274.1118, found 274.1111.

Example 55
1-((2-Carboxyphenyl)amino)-2-((2-fluorophenyl)amino) ethane (Compound BN)

To a solution of BH₃·THF (1.00M, 10.0 mL 300 mol %) at 5° C. was added a solution of 2-(2-(((2-fluorophenyl) amino)acetylamino)benzoic acid from Example 2 (1.0 g, 3.47 mmol) in anhydrous THF (10 mL). After stirring for 5 min at 10° C., the reaction mixture was refluxed for 2.5 h and then cooled to rt. The reaction mixture was quenched with 25% (w/v) NaOH (4 mL) and then the solution was refluxed for 4 h. After cooling to rt, the reaction mixture was stirred for 20 h, water (50 mL) was added, and then the mixture was extracted with ether (3×100 mL). The water layer was acidified with 1N HCl to pH=3-4 and then the light crystalline product which crystallized was filtered and washed several times with cold water. After drying in a vacuum oven at 50° C. for 5 h, 0.23 g (24%) of the title compound was obtained which contained ca 5% of an impurity by $^1$H NMR: mp 127°–128° C. Further purification by LPLC (EtOAc-hexane 1:2), afforded, after drying in vacuo, 176 mg (19%) of the title compound: mp 135.7°–136.2° C.; $^1$H NMR (CDCl₃) δ8.00 (d, 1H, J=8, NH), 7.42 (t, 2H, J=6.8), 7.05–6.97 (m, 2H), 6.80–6.65 (m, 4H), 3.55 (d, 2H, J=4.8), 3.51 (d, 2H, J=4); $^{13}$C NMR (CDCl₃) δ173.37, 151.72 (d, J=238), 151.38, 135.63, 132.83, 124.60 (d, J=3.8), 117.27 (d, J=6.8), 115.30, 114.73, 114.54, 112.32, 111.33, 109.25, 42.75, 42.12; MS (EI, m/z) 274 (M⁺).

Example 56
4-(2-(Bromoacetyl)amino)phenylacetic Acid

To a solution of 4-aminophenylacetic acid (8.0 g, 0.053 mol) in anhydrous dioxane (30 mL) and anhydrous DMF (30 mL) was added, dropwise, bromoacetyl bromide (10.68 g, 4.6 mL) while keeping the internal temperature between 0° C. and 2° C. After the addition was completed (~30 min), the reaction mixture was stirred overnight at rt. The reaction mixture was diluted with water (100 mL), and then the precipitated solid was filtered, washed sequentially with 5% HBr (200 mL) and water (3×200 mL), air dried for several days, and then dried in a vacuum oven at 40°–45° C. for 10 h, giving 7.2 g (50%) of the title compound: mp 173°–175° C. (dec., became "wet" at 169° C.); $^1$H NMR (DMSO-$d_6$) δ12.35 (bs, 1H, COOH), 10.36 (s, 1H, NH), 7.51 (d, 2H, J=8.4), 7.20 (d, 2H, J=8.4), 4.03 (s, 2H), 3.52 (s, 2H); $^{13}$C NMR (DMSO-$d_6$) δ172.73; 164.67; 137.13; 130.47; 129.79; 119.13; 30.42; MS (EI, m/z) 271 (M⁺), 273 (M+2⁺). HRMS (EI) calcd for $C_{10}H_{10}NO_3Br$ 270.9844, found 270.9842.

Example 57
4-(2-(((2-Fluorophenyl)amino)acetyl)amino)phenylacetic Acid (Compound BO)

A solution of 4-(2-(bromoacetyl)amino)phenylacetic acid from Example 56 (4.3 g, 0.016 mol) and o-fluoroaniline (3.51 g, 3 mL, 200 mol %) in anhydrous DMF (30 mL) was heated at 100° C. for 20 h. After cooling to rt, the reaction mixture was poured into ice water. 5% KOH was added to

37 adjust the pH to 9, and then the solution was extracted with CH$_2$Cl$_2$ (3×100 mL). The CH$_2$Cl$_2$ layer was set aside, the aqueous layer was acidified with 5% HCl to pH=5, and then the light crystalline compound which formed was filtered, washed with water (3×70 mL), air dried for several days, and then dried in a vacuum oven for 15 h at 40°–45° C., giving 2.5 g (52.4%) of the title compound: mp 132°–134.5° C. (became "wet" at 128° C.); $^1$H NMR (DMSO-d$_6$) δ12.28 (bs, 1H, COOH), 10.01 (s, 1H, NH), 7.53 (d, 2H, J=8.4), 7.18 (d, 2H, J=11.6), 7.05 (dd, 1H, J=8, J=11.6), 6.61 (dd, 1H, J=8.8, J=8.4), 5.56 (s, 1H, NH), 3.92 (s, 2H), 3.50 (s, 2H); $^{13}$C NMR (DMSO-d$_6$) δ172.77, 168.74, 150.92 (d, J=237.86), 137.34, 136.41 (d, J=11.97), 129.93, 129.64, 124.76 (d, J=2.82), 119.18, 116.27 (d, J=7.04), 114.48, 114.30, 112.15 (d, J=3.62), 46.65, 40.08; MS (EI, m/z) 302 (M$^+$). HRMS (EI) calcd for C$_{16}$H$_{15}$N$_2$O$_3$F 302.1067, found 302.1060.

Example 58

4-((2-Bromoacetyl)amino)benzyl Cyanide

To a solution of 4-aminobenzyl cyanide (4 g, 0.03 mol) in anhydrous DMF (20 mL) and anhydrous dioxane (20 mL) in a 3-necked flask, fitted with magnetic stirrer and a constant additional funnel, was added, dropwise, bromoacetyl bromide (6.12 g, 2.7 mL, 100 mol %) while keeping the internal temperature between 0° C. and 2° C. After the addition was completed (~25 min), the reaction mixture was stirred overnight at rt. The reaction mixture was diluted with water (100 mL) and then the yellow crystalline compound which precipitated was filtered, washed sequentially with 5% HBr (100 mL) and water (200 mL), and then dried in a vacuum oven at 40°–45° C., affording 5.0 g (66%) of the title compound: mp 129°–131° C.; $^1$H NMR (DMSO-d$_6$) δ10.46 (s, 1H, NH), 7.60 (d, 2H, J=8.4), 7.31 (d, 2H, J=8.8), 4.04 (s, 2H), 3.98 (s, 2H): $^{13}$C NMR (DMSO-d$_6$) δ164.82; 137.99; 128.60; 126.42; 119.61; 30.30; 21.82; MS (EI, m/z) 252 (M$^+$). HRMS (EI) calcd for C$_{10}$H$_9$N$_2$OBr 251.9898, found 251.9882.

Example 59

4-(2-(((2-Fluorophenyl)amino)acetyl)amino)benzyl Cyanide (Compound BP)

A solution of 4-((2-bromoacetyl)amino)benzyl cyanide from Example 58 (2.0 g, 7.9 mmol) and o-fluoroaniline (1.75 g, 1.53 mL, 200 mol %) in anhydrous DMF (25 mL) was heated at 90° C. for 17 h. After cooling, the reaction mixture was poured into ice water, 5% KOH was added to bring the solution to pH 9, and then the solution was extracted with CH$_2$Cl$_3$ (3×100 mL). The CH$_2$Cl$_2$ layer was washed sequentially with water (2×100 mL) and brine (100 mL), dried, and then concentrated. Trituration of the product with hexane, and then with ether, gave, after drying in a vacuum oven at 40°–45° C. for 15 h, 1.7 g (76%) of the title compound as yellow crystals: mp 113°–115.7° C. (became "wet" at 103° C.); $^1$H NMR (CDCl$_3$) δ8.59 (d, 1H, NH), 7.59–7.56 (m, 2H), 7.30 (dd, 1H, J=2.8, J=11.2), 7.20–7.02 (m, 2H), 6.84–6.79 (m, 1H), 6.72–6.67 (m, 1H), 3.97 (s, 2H), 3.72 (s, 2H); $^{13}$C NMR (CDCl$_3$) δ168.50, 151.75 (d, J=239.98), 137.07, 128.60 (d, J=5.63 Hz), 125.88, 125.05 (d, J=3.2), 120.50 (d, J=13.48), 119.75, 119.68, 117.75, 115.07, 114.88, 113.14, 113.11, 49.48, 23.10; MS (EI, m/z) 283.1 (M$^+$). HRMS (EI) calcd for C$_{16}$H$_{14}$N$_3$OF 283.1121, found 283.1118.

Example 60

4-(2-(((2-Fluorophenyl)amino)acetyl)amino)benzyl Tetrazole (Compound BQ)

To a solution of 4-(2-(((2-fluorophenyl)amino)acetyl) amino)benzyl cyanide from Example 59 (0.4 g, 1.4 mmol)

38 in anhydrous DMF (10 mL) was added NaN$_3$ (0.12 g, 130 mol %), NH$_4$Cl (0.1 g, 130 mol %), and a catalytic amount of LiCl (30 mg). This mixture was heated and stirred at 127° C. for 30 h, and then stirred for several days at rt. The reaction mixture was heated to 80° C., filtered while hot, and then the nonorganic residue was washed with small amount of DMF. The DMF solution was concentrated, giving darkorange oily product, which was stirred with H$_2$O (50 mL). The pH of this mixture was adjusted to 4–5 with 5% HCl, the mixture was extracted with EtOAc (3×50 mL), and then the combined EtOAc layer was dried, filtered, and then concentrated. Purification by LPLC (EtOAc, then MeOH-EtOAc 1:9) gave 0.1 g (22%) of the desired product. Recrystallization from a small amount of CHCl$_3$ (0.5 mL) gave 0.06 g (13%) of the title compound: mp 146°–147.8° C. (became "wet" at 143° C.); $^1$H NMR (DMSO-d$_6$) δ10.04 (s, 1H, NH), 7.55 (t, 1H, J=4), 7.19 (t, 1H, J=4.4), 7.07–6.94 (m, 2H), 6.62–6.57 (m, 2H), 5.73 (s, 1H, NH), 4.22 (s, 2H), 3.91 (d, 2H, J=6); $^{13}$C NMR (DMSO-d$_6$) δ168.83, 155.40, 150.90 (d,J=237.16), 137.66, 136.39 (d, J=11.26), 130.74, 128.99, 124.74 (d, J=2.8), 119.51, 116.26 (d, J=6.3), 114.48, 114.30, 112.12 (d, J=3.5), 46.62, 28.34.

Example 61

3-(2-(((2-Fluorophenyl)amino)acetyl)amino)pyridine (Compound BR)

A solution of 2-((2-fluorophenyl)amino)acetic acid (0.8 g, 4.73 mmol) in anhydrous THF (20 mL) was cooled to –20° C. and then N-methyl morpholine (0.8 mL, 150 mol %) was added, followed by the dropwise addition of isobutyl chloroformate (0.7 g, 0.7 mL, 110 mol %). After stirring for 15 min at –20° C., 3-aminopyridine (0.9 g, 200 mol %) was added, and the reaction mixture was warmed to 0° C. and stirred for 9 h at this temperature. After solvent evaporation, the residue (dark cherry color) was dissolved in EtOAc (170 mL), and then washed sequentially with 1.0M citric acid (40 mL), 5% NaHCO$_3$ (2×30 mL), water (30 mL), and brine (30 mL). The EtOAc layer was dried, concentrated, and then purified by LPLC (EtOAc-hexane 1:1), giving 0.4 g (38%) of the title compound which contained a minor impurity (~10%): $^1$H NMR (DMSO-d$_6$) δ10.25 (s, 1H, NH), 8.75 (d, 1H, J=2.4), 8.26 (dd, 1H, J=1.2, J=4.4), 8.05–8.02 (m, 1H), 7.34 (dd, 1H, J=4.8, J=8.4), 7.05–6.97 (m, 4H ), 6.63–6.60 (m, 2H), 5.8 (s, 1H, NH), 3.35 (s, 2H); $^{13}$C NMR (DMSO-d$_6$) δ169.60, 150.90 (d, J=237.16), 144.30, 140.77 (d, J=31.28), 136.38 (d, J=11.47), 135.45, 126.27, 124.75 (d, J=3.11), 123.65 (d, J=7.64), 116.30 (d, J=6.84), 114.40 (d, J=18.30), 112.14 (d, J=3.82), 46.63; MS (EI, m/z)245 (M$^+$), 345 (impurity); MS (FAB, m/z) 246 (M$^+$), 346 (impurity). HRMS (EI) calcd for C$_{13}$H$_{12}$N$_3$OF 245.0964, found 245.0964.

Example 62

2-(2-(((4-Bromophenyl)amino)acetyl)amino)benzoic Acid (Compound BS)

A solution of 2-((2-bromoacetyl)amino)benzoic acid (8.0 g, 31 mmol) and 4-bromoaniline (13.3 g, 77 mmol) in anhydrous DMF (80 mL) was heated to 70° C. overnight with stirring under N$_2$. The solution was cooled, poured into 500 mL of ice-water, and then a 5% KOH solution was added until the pH of the solution was 10. The solution was extracted with CH$_2$Cl$_2$ (3×250 mL), the aqueous layer was acidified to pH=3 using 2N HCl, and then the precipitate which formed was filtered, washed with water and then dried in a vacuum oven overnight (55° C.) to yield 9.0 g (83.1%) of the title compound as a pale orange powder, mp 213°–214° C.: $^1$H NMR (DMSO-d$_6$) δ13.51 (bs, 1H), 11.95 (s, 1H), 8.70 (d, J=8.0, 1H), 7.93 (dd, J=8.0, J=1.6, 1H), 7.59

(dt, J=8.8, J=1.6, 1H), 7.23 (d, J=9.2, 2H), 7.13 (dt, J=8.0, J=1.2, 1H), 6.74 (J=5.6, 1H), 6.54 (d, J=8.8, 2H), 3.83 (J=5.2, 2H); $^{13}$C NMR (DMSO-d$_6$) δ170.33, 169.09, 147.39, 140.50, 134.18, 131.49, 131.12, 122.72, 119.38, 115.93, 114.35, 107.76, 48.61; MS (EI, m/z) 348 (M$^+$).

Example 63
2-(2-(((4-Nitrophenyl)amino)acetyl)amino)benzoic Acid (Compound BT)

A solution of 2-((2-bromoacetyl)amino)benzoic acid (8.0 g, 31 mmol), 4-nitroaniline (10.7 g, 77 mmol) and 4-dimethylaminopyridine (0.2 g, 1.6 mmol) in anhydrous DMF (80 mL) was heated to 70° C. overnight with stirring under N$_2$. The solution was cooled, poured into 500 mL of ice-water, and then a 5% KOH solution was added until the pH of the solution was 10. The solution was extracted with CH$_2$Cl$_2$ (3×200 mL), the aqueous layer was acidified to pH=3 using 2N HCl, and then the precipitate which formed was filtered, washed with water, and then dried in a vacuum dessicator overnight. Further drying in a vacuum oven (55° C.) gave 5.07 g (52%) of the title compound as a orange-brown powder, mp 236°–243° C: $^1$H NMR (DMSO-d$_6$) δ13.60 (bs, 1H), 11.80 (s, 1H), 8.65 (d, J=8.4, 1H), 8.03 (d, J=9.2, 2H), 7.95 (dd, J=7.6, J=1.6/1H), 7.91 (t, J=6.4, 1H), 7.60 (dt, J=8.8, J=1.6, 1H), 7.15 (dt, J=8.0, J=1.0, 1H), 6.73 (d, J=9.2, 2H), 4.09 (d, J=6.4, 2H); $^{13}$C NMR (DMSO-d$_6$) δ169.30, 168.88, 154.08, 140.37, 136.99, 134.25, 131.15, 126.06, 122.93, 119.51, 116.08, 111.58, 47.59; MS (FAB, m/z) 316.2 (M$^+$).

Example 64
2-(2-(((4-(Trifluoromethoxy)phenyl)amino)acetyl)amino)benzoic Acid (Compound BU)

A solution of 2-((2-bromoacetyl)amino)benzoic acid (2.57 g, 10 mmol) and 4-trifluoromethoxyaniline (2.7 mL, 3.54 g, 20 mmol) in anhydrous DMF (60 mL) was heated to 100° C. overnight with stirring under N$_2$. The solution was cooled, poured into 600 mL of ice-water, and then a 5% KOH solution was added until the pH of the solution was 10. The solution was extracted with CH$_2$Cl$_2$ (3×250 ml), the aqueous layer was acidified to pH=3 using 2N HCl, and then the precipitate which formed was filtered, washed with water, and then dried in a vacuum oven overnight (45° C.) to yield 2.13 g (60%) of the title compound as a pale brown powder, mp 181°–184° C.: $^1$H NMR (DMSO-d$_6$) δ13.51 (bs, 1H), 11.95 (s, 1H), 8.70 (d, J=8.4, 1H), 7.93 (dd, J=8.0, J=1.6, 1H), 7.59 (m, 1H), 7.13 (dt, J=8.0, J=1.6, 1H), 7.09 (d, J=8.8, 2H), 6.76 (t, J=5.6, 1H), 6.63 (d, J=8.8, 2H), 3.87 (d, J=5.6 2H); $^{13}$C NMR (DMSO-d$_6$) δ170.24, 169.02, 147.31, 140.43, 139.27, 134.07, 131.0.5, 122.65, 121.99, 119.38, 115.99, 112.88, 48.73; MS (EI, m/z) 354 (M$^+$).

Example 65
2-(2-(((4-Phenyl)phenoxy)acetyl)amino)benzoic Acid (Compound BV)

A solution of 4-phenylphenol (5.1 g, 30 mmol) was dissolved in anhydrous THF (100 mL) with stirring under N$_2$. The reaction mixture was cooled using an ice-bath, and then NaH (1.33 g, 60% dispersion in mineral oil) was added to the solution, causing some bubbling. The ice-bath was removed and then the reaction mixture was stirred for 30-min before 2-((2-bromoacetyl)amino)benzoic acid (4.0 g, 15 mmol) was added. The resulting solution was stirred for 48 h. Water (100 mL) was added, the solution was extracted with 2×70 mL of ether, and then the aqueous layer was acidified to pH=3 using 2N HCl. The white precipitate which formed was filtered, washed with water, and then dried in a vacuum dessicator overnight. This white solid was triturated with hexane to remove 4-phenylphenol, and then triturated with ether-chloroform (1:1) to remove the starting acid. The precipitate was filtered and then dried in a vacuum oven (45° C.) overnight to yield 2.22 g (41%) of the title compound as a white powder, mp 229°–231° C.: $^1$H NMR (DMSO-d$_6$) δ13.82 (bs, 1H), 12.22 (s, 1H), 8.72 (dd, J=8.6, J=1.2, 1H), 8.02 (dd, J=8.0, J=1.6, 1H), 7.67–7.61 (m, 5H), 7.43 (t, J=7.6, 2H), 7.31 (tt, J=7.6, J=2.0, 1H), 7.22–7.16 (m, 3H), 3.87 (s, 2H); $^{13}$C NMR (DMSO-d$_6$) δ169.38, 167.10, 156.71, 140.13, 139.55, 134.27, 133.69, 131.24, 128.80, 127.85, 126.85, 126.24, 123.03, 119.42, 116.14, 115.24, 67.39; MS (EI, m/z) 347 (M$^+$).

Example 66
2-(2-(((4-Trifluoromethyl)phenoxy)acetyl)amino)benzoic Acid (Compound BW)

A solution of 4-trifluoromethylphenol (3.16 g, 20 mmol) was dissolved in anhydrous THF (100 mL) with stirring under N$_2$. NaH (1.20 g, 60% dispersion in mineral oil) was then added to the solution, causing some bubbling, and then the resulting mixture was stirred for 30 min before 2-((2-bromoacetyl)amino)benzoic acid (3.16 g, 20 mmol) was added. The solution was stirred overnight, water (100 mL) was added, and then the solution was extracted with ether (3×70 mL). The aqueous layer was acidified to pH=3 using 2N HCl and then the white precipitate which formed was filtered, washed with water, and then dried in a vacuum dessicator overnight to yield 3.00 g (88%) of the title compound as a white powder, mp 230°–235° C.: $^1$H NMR (DMSO-d$_6$) δ13.82 (bs, 1H), 12.16 (s, 1H), 8.69 (dd, J=8.4, J=0.8, 1H), 8.02 (dd, J=7.6, J=1.6, 1H), 7.73 (d, J=8.8, 2H), 7.63 (m, 1H), 7.26 (d, J=8.8, 2H), 7.20 (m, 1H), 4.85 (s, 2H); $^{13}$C NMR (DMSO-d$_6$) δ169.46, 166.53, 159.85, 140.09, 134.32, 131.28, 127.13, 127.10, 123.13, 119-46, 116.18, 115.35, 67.36; MS (EI, m/z) 389 (M$^+$).

Example 67
3-Methoxy-2-((bromoacetyl)amino)benzoic Acid

A solution of 3-methoxy-2-aminobenzoic acid (5.0 g, 30 mmol) in a mixture of anhydrous DMF (30 mL) and anhydrous dioxane (30 mL) in a 250 mL-3-necked round-bottomed flask equipped with a constant addition funnel (60 mL) was cooled with an ice-bath to −5° C. Bromoacetyl bromide (6.66 g, 2.90 mL, 30 mmol) was added dropwise, keeping the internal temperature between −5° to 0° C. over a ½ h period. After the addition of bromoacetyl bromide was completed, the solution was warmed to room temperature and then stirred overnight. To the solution was slowly added 150 mL of ice-water, causing a pale white solid to precipitate. The precipitate was filtered, washed with water, and then dried in a vacuum oven overnight to afford 6.26 g (72%) of the title compound as a pale-white solid, mp 178°—180° C. (decomp): $^1$H NMR (DMSO-d$_6$) δ12.80 (bs, 1H), 9.80 (s, 1H), 7.30–7.25 (m, 3H), 4.05 (s, 2H), 3.81 (s, 3H); $^{13}$C NMR (DMSO-d$_6$) δ167.37, 164.54, 153.67, 129.76, 126.56, 124.39, 121.18, 114.66, 56.03, 29.63; MS (EI, m/z) 287 (M$^+$).

Example 68
4-Fluoro-2-((bromoacetyl)amino)benzoic Acid

A solution of 4-fluoro-2-aminobenzoic acid (5.0 g, 32.2 mmol) in a mixture of anhydrous DMF (30 mL) and anhydrous dioxane (30 mL) in a 250 mL 3-necked round-bottomed flask which was equipped with a constant addition funnel (60 mL) was cooled with an ice-bath to −5° C. Bromoacetyl bromide (6.44 g, 2.8 mL, 32.2 mmol) was added dropwise while keeping the internal temperature between −5° and 0° C. over a ½ h period. After the addition of the bromoacetyl bromide was completed, the solution was warmed to room temperature and stirred overnight. To this solution was slowly added 150 mL of ice-water, causing a solid to precipitate. The precipitate was filtered, washed with water, and then dried in a vacuum dessicator overnight to afford 8.13 g (91.4%) of the title compound as a white solid, mp 166°–168° C.: $^1$H NMR (DMSO-$d_6$) δ13.92 (bs, 1H), 11.83 (s, 1H), 8.32 (dd, J=12, J=2.4, 1H), 8.09 (dd, J=9.2, J=6.8, 1H), 7.06 (ddd, J=8.8, J=9.2, J=2.4, 1H), 4.29 (s, 2H); $^{13}$C NMR (DMSO-$d_6$) δ168.55, 165.60, 164.80 (d, J=248), 142.29 (d, J=12.9), 133.93 (d, J=10.6), 113.19, 110.42 (d, J=22), 106.43 (d, J=28), 30.54; MS (EI, m/z) 275 (M$^+$).

Example 69
3-Methoxy-2-(2-((phenylamino)acetyl)amino)benzoic Acid

A solution of 3-methoxy-2-((bromoacetyl)amino)benzoic acid (6.0 g, 21 mmol) and aniline (6 mL, 6.14 mL, 66 mmol) in anhydrous DMF (50 mL) was heated to 95°–100° C. overnight with stirring under $N_2$. The solution was cooled to room temperature, poured into 500 mL of ice-water, and then a 5% KOH solution was added until the pH of the solution was 10. The solution was extracted with $CH_2Cl_2$ (2×150 mL), the aqueous layer was acidified to pH 3 using 2N HCl, and then the precipitate which formed was filtered, washed with water, and then dried in a vacuum dessicator overnight to yield 4.72 g (74%) of the title compound as a pale-green solid, mp 197°–200° C. (decomp): $^1$H NMR (DMSO-$d_6$) δ9.32 (s, 1H), 7.30-7.21 (m, H), 7.10 (pseudo t, 2H), 6.64-6.58 (m, 3H), 6.2 (bs, 1H), 3.76 (s, 2H), 3.75 (s, 3H); $^{13}$C NMR (DMSO-$d_6$) δ169.06, 167.64, 153.39, 148.30, 129.14, 128.80, 125.97, 124.92, 121.21, 116.67, 114.60, 112.66, 56.01, 47.39; MS (EI, m/z) 300 (M$^+$).

Example 70
4-Fluoro-2-(2-((phenylamino)acetyl)amino)benzoic Acid (Compound BX)

A solution of 4-fluoro-2-((bromoacetyl)amino)benzoic acid (Compound BX) (7.50 g, 27 mmol) and aniline (6.33 g, 68 mmol) in anhydrous DMF (50 mL) was heated to 95°–100° C. overnight with stirring under $N_2$. The solution was cooled, poured into 500 mL of ice-water, and then a 5% KOH solution was added until the pH of the solution was 10. The solution was extracted with $CH_2Cl_2$ (2×150 mL), the aqueous layer was acidified to pH=3 using 2N HCl, and then the precipitate which formed was filtered, washed with water, and then dried in a vacuum dessicator overnight to yield 7.11 g (91%) of the title compound as a white solid, mp 227°–230° C.: $^1$H NMR (DMSO-$d_6$) δ13.5 (bs, 1H), 12.20 (s, 1H), 8.85 (dd, J=12.4, J=1-6), 8-01 (dd, J=8.8, J=6.8, 1H), 7.12-7.06 (m, 2H), 6.98 (ddd, J=8.8, J=8.0, J=2.8), 6.63-6.57 (m, 3H), 6.45 (bs, 1H), 3.85 (s, 2H); $^{13}$C NMR (DMSO-$d_6$) δ171.56, 168.28, 164.94 (d, J=247), 147.99, 142.55 (d, J=11.2), 133.87 (d, J=11.2), 128.95, 117.12, 112.42, 109.70 (d, J=21.8), 105.92 (d, J=28.2), 48.88; MS (EI, m/z) 288 (M$^+$).

Example 71
4-(((tert-Butyldimethyl)sily)oxy)aniline

A mixture of 4-aminophenol (10.0 g, 91.6 mmol), tert-butyldimethylsilyl chloride (13.81 g, 91.6 mmol), imidazole (12.47 g, 183.2 mmol) and anhydrous $CH_2Cl_2$ (200 mL) was stirred at room temperature overnight. TLC analysis showed appearance of a new spot and the disappearance of the starting phenol. The reaction mixture was concentrated and then the remaining oily product was loaded onto a silica gel column and purified by chromatography, eluting with 3:1 hexane-ethyl acetate, to afford 16.60 g (81%) of the title compound as a deep-brown oil: $^1$H NMR (DMSO-$d_6$), δ6.52 (d, J=8.8, 2H), 6.45 (d, J=8.8, 2H), 4.61 (s, 2H), 0.92 (s, 9H), 0.10 (s, 6H); $^{13}$C NMR (DMSO-$d_6$) δ145.45, 142.79, 119.94, 114.88, 25.62, 17.84, –4.57; MS (EI, m/z) 223 (M$^+$).

Example 72
4-(((tert-Butyldimethylsilyl)oxy)methyl)aniline

A mixture of 4-aminobenzyl alcohol (30.0 g, 81.2 mmol), tert-butyldimethylsilyl chloride (12.24 g, 81.2 mmol), imidazole (11.05 g, 162.4 mmol) and anhydrous $CH_2Cl_2$ (200 mL) was stirred at room temperature overnight. TLC analysis showed the appearance of a new spot and the disappearance of starting phenol. The solvent was removed in vacuo and then the remaining oily product was loaded onto a silica gel column and purified by chromatography, eluting with 3:1 hexane-ethyl acetate to afford 15.41 g (80%) of the title compound as a pale orange oil: $^1$H NMR (DMSO-$d_6$) δ6.95 (d, J=8.4, 2H), 6.53 (d, J=8.4, 2H), 4.96 (s, 2H), 4.50 (s, 2H), 0.88 (s, 9H), 0.04 (s, 6H); $^{13}$C NMR (DMSO-$d_6$) δ147.65, 128.04, 127.58, 113.57, 64.69, 25.82, 17.97, –5.18; MS (EI, m/z) 237 (M$^+$).

Example 73
Methyl 2-(-(Bromoacetyl)amino)benzoate

A solution of methyl anthranilate (10.0 g, 66 mmol) in a mixture of anhydrous DMF (30 mL) and anhydrous dioxane (30 mL) in a 250 mL 3-necked round-bottomed flask equipped with a constant addition funnel (60 mL) was cooled to –5° C. using an ice-bath. Bromoacetyl bromide (13.32 g, 5.8 mL, 66 mmol) was added dropwise, keeping the internal temperature between –5° to 0° C. over a ½ h period. After the addition of the bromide was completed, the solution was warmed to rt, stirred overnight and then the resulting solution was slowly poured into 500 mL of ice-water, causing a white solid to precipitate. The precipitate was filtered, washed with water, and then dried in a vacuum dessicator overnight to afford 16.4 g (91%) of the title compound as a white solid, mp 86°–87° C.: $^1$H NMR (DMSO-$d_6$) δ11.07 (s, 1H), 8.24 (dd, J=8.4, J=1.2, 1H), 7.94 (dd, J=8.0, J=1.6, 1H), 7.64 (dt, J=8.8, J=1.6, 1H), 7.24 (dt, J=8.4, J=1.2, 1H), 4.23 (s, 2H), 3.87 (s, 3H); $^{13}$C NMR (DMSO-$d_6$) δ167.26, 165.02, 138-82, 133.97, 130.62, 123.91, 121.13, 118-09, 52.46, 30.34; MS (EI, m/z) 271 (M$^+$).

Example 74
4-((Bromoacetyl)amino)benzonitrile

A solution of 4-aminobenzonitrile (5.0 g, 42.3 mmol) in a mixture of anhydrous DMF (30 mL) and anhydrous dioxane (30 mL) in a 250 mL 3-necked round-bottomed flask equipped with a constant addition funnel (60 mL) was cooled to 0° C. using an ice-bath. Bromoacetyl bromide (8.53 g, 3.7 mL, 42.3 mmol) was added dropwise, keeping the internal temperature between 0° and 5° C. over a ½ h period. After the addition of the bromoacetyl bromide was completed, the solution was warmed to rt, stirred overnight, and then the solution was slowly poured into 500 mL of ice-water, causing a pale brown solid to precipitate. The precipitate was filtered, washed with water, and then dried in a vacuum dessicator overnight to afford 7.78 g (77%) of the title compound as a pale brown solid, mp 166°–168° C.: $^1$H NMR (DMSO-$d_6$) δ10.81 (s, 1H), 7.81-7.74 (m, 4H), 4.08 (s, 2H); $^{13}$C NMR (DMSO-$d_6$) δ165.60, 142.75, 133.39, 119.28, 118.89, 105.60, 30.17; MS (EI, m/z) 238 (M$^+$).

Example 75
Methyl 4-((Bromoacetyl)amino)benzoate

A solution of methyl 4-aminobenzoate (5.0 g, 33 mmol) in a mixture of anhydrous DMF (30 mL) and anhydrous dioxane (30 mL) in a 250 mL 3-necked round-bottomed flask equipped with a constant addition funnel (60 mL) was cooled to 0° C. using an ice-bath. Bromoacetyl bromide (6.66 g, 2.9 mL, 33 mmol) was added dropwise, keeping the internal temperature between 0° to 5° C. over a ½ h period. After the addition the bromoacetyl bromide was completed, the solution was warmed to rt, stirred overnight, and then the solution was slowly poured into 500 mL of ice-water, causing a solid to precipitate. The precipitate was filtered, washed with water, and then dried in a vacuum dessicator overnight to afford 6.83 g (76%) of the title compound as a pale brown solid; mp 153°–155° C.: $^1$H NMR (DMSO-$d_6$) δ10.72 (s, 1H), 7.93 (d, J=8.8, 3H), 7.72 (d, J=8.8, 2H), 4.07 (s, 2H), 3.82 (s, 3H) $^{13}$C NMR (DMSO-$d_6$) δ165.69, 165.36, 124.91, 130.26, 124.49, 118.64, 51.92, 30.25; MS (EI, m/z) 271 (M$^+$).

Example 76
4-((Bromoacetyl)amino)benzoic Acid

A solution of 4-aminobenzoic acid (5.0 g, 36 mmol) in a mixture of anhydrous DMF (30 mL) and anhydrous dioxane (30 mL) in a 250 mL 3-necked round-bottomed flask equipped with a constant addition funnel (60 mL) was cooled to 0° C. using an ice-bath. Bromoacetyl bromide (7.27 g, 3.16 mL, 36 mmol) was then added dropwise, keeping the internal temperature between 0° and 5° C. over a ½ h period. After the addition of the bromoacetyl bromide was completed, the solution was warmed to rt, stirred overnight, and then the solution was slowly poured into 500 mL of ice-water, causing a solid to precipitate. The precipitate was filtered, washed with water, and then dried in a vacuum dessicator overnight to afford 7.46 g (81%) of the title compound as a white solid, mp 241°–243° C.: $^1$H NMR (DMSO-$d_6$) δ12.79 (bs, 1H), 10.68 (s, 1H), 7.91 (d, J=9.2, 2H), 7.69 (d, J=9.2, 2H), 4.06 (s, 2H); $^{13}$C NMR (DMSO-$d_6$) δ166.79, 165.28, 142.56, 130.47, 125.70, 118.53, 30.29; MS (EI, m/z) 259 (M$^+$).

Example 77
Ethyl 4-(Bromoacetyl)amino)benzoate

A solution of ethyl 4-aminobenzoate (3.0 g, 18 mmol) in a mixture of anhydrous DMF (30 mL) and anhydrous dioxane (30 mL) in a 250 mL 3-necked round-bottomed flask equipped with a constant addition funnel (60 mL) was cooled to 0° C. using an ice-bath. Bromoacetyl bromide (3.68 g, 1.6 mL, 18 mmol) was added dropwise, keeping the internal temperature between 0° and 5° C. over a ½ h period. After the addition of the bromoacetyl bromide was completed, the solution was warmed to rt, stirred overnight, and then the solution was slowly poured into 500 mL of ice-water, causing a solid to precipitate. The precipitate was filtered, washed with water, and then dried in a vacuum dessicator overnight to afford 4.90 g (95%) of the title compound as a white solid, mp 116°–118° C.: $^1$H NMR (DMSO-$d_6$) δ10.71 (s, 1H), 7.93 (d, J=8.8, 2H), 7.71 (d, J=8.8, 2H), 4.28 (q, J=7.2, 2H), 4.07 (s,2H) 1.30 (t, J=7.2, 3H); $^{13}$C NMR (DMSO-$d_6$) δ165.36, 165.23, 142.87, 130.32, 124.79, 118.64, 60.49, 30.26, 14.18; MS (EI, m/z) 287 (M$^+$).

Example 78
Ethyl 2-((Bromoacetyl)amino)benzoate

A solution of ethyl 2-aminobenzoate (3.0 g, 18 mmol) in a mixture of anhydrous DMF (30 mL) and anhydrous dioxane (30 mL) in a 250 mL 3-necked round-bottomed flask equipped with a constant addition funnel (60 mL) was cooled to 0° C. using an ice-bath. Bromoacetyl bromide (3.68 g, 1.6 mL, 18 mmol) was added dropwise, keeping the internal temperature between 0° and 5° C. over a ½ h period. After the addition of the bromoacetyl bromide was completed, the solution was warmed to rt, stirred overnight, and then the solution was slowly poured into 500 mL of ice-water, causing a solid to precipitate. The precipitate was filtered, washed with water, and then dried in a vacuum dessicator overnight to afford 3.32 g (65%) of the title compound as a white solid, mp 65°–66° C.: $^1$H NMR (DMSO-$d_6$) δ11.08 (s, 1H), 8.25 (dd, J=7.6, J=0.8, 1H), 7.95 (dd, J=8.0, J=1.2, 1H), 7.63 (t, J=8.4, 1H), 7.25 (dt, J=7.6, J=1.2, 1H), 4.33 (q, J=7.2, 2H), 4.23 (s, 2H), 1.33 (t, J=7.2, 3H); $^{13}$C NMR (DMSO-$d_6$) δ166.82, 165.02, 138.86, 133.95, 130.62, 123.93, 121.11, 118.23, 61.30, 30.40, 13.99; MS (EI, m/z) 287 (M$^+$).

Example 79
4-((Bromoacetyl)amino)-1-nitrobenzene

A solution of 4-nitroaniline (10.0 g, 72.4 mmol) in a mixture of anhydrous DMF (30 mL) and anhydrous dioxane (30 mL) in a 250 mL 3-necked round-bottomed flask equipped with a constant addition funnel (60 mL) was cooled to 0° C. using an ice-bath. Bromoacetyl bromide (14.60 g, 6.35 mL, 72.4 mmol) was added dropwise, keeping the internal temperature between 0° and 5° C. over a ½ h period. After the addition of the bromoacetyl bromide was completed, the solution was warmed to rt, stirred overnight, and then the solution was slowly poured into 500 mL of ice-water, causing a solid to precipitate. The precipitate was filtered, washed with water, and then dried in a vacuum dessicator overnight to afford 16.92 g (90%) of the title compound as a greenish yellow solid, mp 175°–178° C.: $^1$H NMR (DMSO-$d_6$) δ10.98 (s, 1H), 8.24 (d, J=9.2, 2H), 7.83 (d, J=9.2, 2H), 4.10 (s, 2H); $^{13}$C NMR (DMSO-$d_6$) δ165.77, 144.67, 142.62, 125.05, 119.01, 30.15; MS (EI, m/z) 285 (M$^+$).

Example 80
4-((Bromoacetyl)amino)benzyl cyanide

A solution of 4-aminobenzyl cyanide (7.5 g, 56.7 mmol) in a mixture of anhydrous DMF (30 mL) and anhydrous dioxane (30 mL) in a 250 mL 3-necked round-bottomed flask equipped with a constant addition funnel (60 mL) was cooled to 0° C. using an ice-bath. Bromoacetyl bromide (11.4 g, 4.98 mL, 56.7 mmol) was added dropwise, keeping the internal temperature between 0° and 5° C. over a ½ h period. After the addition of the bromoacetyl bromide was completed, the solution was warmed to rt, stirred overnight, and then the solution was slowly poured into 500 mL of ice-water, causing a solid to precipitate. The precipitate was filtered, washed with water, and then dried in a vacuum dessicator overnight to afford 10.5 g (95%) of the title compound as a pale-orange solid, mp 127°–135° C. (decomp): $^1$H NMR (DMSO-$d_6$) δ10.45 (s, 1H), 7.59 (d, J=9.2, 2H), 7.31 (d, J=9.2, 2H), 4.03 (s, 2H), 3.98 (s, 2H); $^{13}$C NMR (DMSO-$d_6$) δ164.83, 137.98, 128.60, 126.42, 119.61, 119.26, 30.31, 21.81; MS (EI, m/z) 252 (M$^+$).

Example 81
4-((Bromoacetyl)amino)-1-butoxyaniline

A solution of 4-butoxyaniline (3.0 g, 18 mmol) in a mixture of anhydrous DMF (30 mL) and anhydrous dioxane (30 mL) in a 250 mL 3-necked round-bottomed flask equipped with a constant addition funnel (60 mL) was cooled to 0° C. using an ice-bath. Bromoacetyl bromide (3.68 g, 1.60 mL, 18 mmol) was added dropwise, keeping the internal temperature between 0° and 5° C. over a ½ h period. After the addition of the bromoacetyl bromide was completed, the solution was warmed to rt, stirred overnight, and then the solution was slowly poured into 500 mL of ice-water, causing a solid to precipitate. The precipitate was filtered, washed with water, and then dried in a vacuum dessicator overnight to afford 3.38 g (65%) of the title compound as a pale purple solid, mp 131°–134° C.: $^1$H NMR (DMSO-d$_6$) δ10.23 (s, 1H), 7.45 (d, J=8.8, 2H), 6.88 (d, J=9.2, 2H), 3.99 (s, 2H), 3.92 (t, J=6.4, 2H), 1.68–1.65 (m, 2H), 1.42–1.40 (m, 2H), 0.92 (t, J=7.2, 3H); $^{13}$C NMR (DMSO-d$_6$) δ164.18, 155.01, 131.57, 120.70, 114.50, 67.22, 30.73, 30.38, 18.70, 13.66; MS (EI, m/z) 287 (M$^+$).

Example 82
4-((Bromoacetyl)amino)benzyl Alcohol

A solution of 4-(((tert-butyldimethylsilyl)oxy)methyl) aniline (14.0 g, 59 mmol) in a mixture of anhydrous DMF (30 mL) and anhydrous dioxane (30 mL) in a 250 mL 3-necked round-bottomed flask equipped with a constant addition funnel (60 mL) was cooled to 0° C. using an ice-bath. Bromoacetyl bromide (11.91 g, 5.18 mL, 59 mmol) was added dropwise, keeping the internal temperature between 0° and 5° C. over a ½ h period. After the addition of the bromoacetyl bromide was completed, the solution was warmed to rt, stirred overnight, and then the solution was slowly poured into 500 mL of ice-water. The resulting precipitate was filtered, washed with water, and then dried in a vacuum dessicator overnight to afford 8.73 g (61%) Of the title compound as a pale yellow crystals, mp 128°–134° C. (decomp), became wet at 89°–93° C.: $^1$H NMR (DMSO-d$_6$) δ10.35 (s, 1H), 7.52 (d, J=8.8, 2H), 7.26 (d, J=8.8, 2H), 4.43 (s, 2H), 4.04 (s, 2H); $^{13}$C NMR (DMSO-d$_6$) δ164.58, 138.00, 137.15, 126.97, 118.94, 62.51, 30.43; MS (EI, m/z) 243 (M$^+$).

Example 83
4-((Bromoacetyl)amino)-1-((tert-butyldimethylsilyl)oxy) benzene

A solution of 4-((tert-butyldimethylsilyl)oxy)methyl) aniline (14.0 g, 63 mmol) in a mixture of anhydrous DMF (30 mL) and anhydrous dioxane (30 mL) in a 250 mL 3-necked round-bottomed flask equipped with a constant addition funnel (60 mL) was cooled to 0° C. using an ice-bath. Bromoacetyl bromide (112.65 g, 5.50 mL, 63 mmol) was added dropwise, keeping the internal temperature between 0° and 5° C. over a ½ h period. After the addition of the bromoacetyl bromide was completed, the solution was warmed to rt, stirred overnight, and then the solution was slowly poured into 500 mL of ice-water. The resulting precipitate was filtered, washed with water, and then dried in a vacuum dessicator overnight to afford 9.76 g (45%) of the title compound as a pale brown solid, mp 112°–113° C.: $^1$H NMR (DMSO-d$_6$) δ10.26 (s, 1H), 7.45 (d, J=8.8, 2H), 6.81 (d, J=8.8, 2H), 3.99 (s, 2H), 0.93 (s, 9H), 0.16 (s, 6H); $^{13}$C NMR (DMSO-d$_6$) δ164.26, 151.19, 132.43, 120.70, 120.07, 119.91, 30.37, 25.55, 17.91, −4.58; MS (EI, m/z) 343 (M$^+$).

Example 84
4-((Bromoacetyl)amino)phenylacetic Acid

A solution of 4-aminophenylacetic acid (3.0 g, 19.8 mmol) in a mixture of anhydrous DMF (30 mL) and anhydrous dioxane (30 mL) in a 250 mL 3-necked round-bottomed flask equipped with a constant addition funnel (60 mL) was cooled to 0° C. using an ice-bath. Bromoacetyl bromide (4.00 g, 1.74 mL, 19.8 mmol) was added dropwise, keeping the internal temperature between 0° and 5° C. over a ½ h period. After the addition of the chloride was completed, the solution was warmed to rt, stirred overnight, and then the solution was slowly poured into 500 mL of ice-water. The resulting precipitate was filtered, washed with water, add then dried in a vacuum dessicator overnight to afford 2.75 (51%) of the title compound as a pale yellow crystals, mp 168°–171° C.: $^1$H NMR (DMSO-d$_6$) δ12.28 (bs, 1H), 10.36 (s, 1H), 7.50 (d, J=8.8, 2H), 7.20 (d, J=8.4, 2H), 4.02 (s, 2H), 3.51(s, 2H); $^{13}$C NMR (DMSO-d$_6$) δ172.70, 164.65, 137.12, 130.45, 129.76, 119.12, 40.12, 30.40; MS (EI, m/z) 271 (M$^+$).

Example 85
Methyl 2-((2-(phenylamino)acetyl)amino)benzoate (Compound BY)

A solution of methyl 2-((bromoacetyl)amino) benzoate (3.0 g, 11 mmol) and aniline (2.55 g, 2.5 mL, 27.5 mmol) in anhydrous DMF (60 mL) was heated to 90°–100° C. overnight with stirring under N$_2$. The solution was cooled, poured into 500 mL of ice-water, and then the resulting precipitate was filtered, washed with water, and then dried under a vacuum dessicator overnight to yield 3.08 g (98%) of the title compound, mp 140°–142° C.: $^1$H NMR (DMSO-d$_6$) δ11.41 (s, 1H), 8.61 (dd, J=8.8, J=1.2, 1H), 7.91 (dd, J=8.0, J=1.6, 1H), 7.62 (ddd, J=8.8, J=7.6, J=1.6, 1H), 7.17 (ddd, J=8.0, J=7.2, J=1.2, 1H), 7.15–7.10 (m, 2H) 6.65-6-60 (m, 3H), 6.50 (t, J=5.6, 1H), 3.83 (d, J=5.6, 2H), 3.72 (s, 3H); $^{13}$C NMR (DMSO-d$_6$) δ170.71, 166.99, 148.16, 139.61, 134.27, 130.80, 128.99, 123.03, 120.10, 117.28, 116.19, 112.59, 52.34, 49.07; MS (EI, m/z) 284 (M$^+$). Anal. Calcd for C$_{16}$H$_{16}$N$_2$O$_3$: C, 67.59; H, 5.67; N, 9.86. Found: C, 67.40; H, 5.61; N, 9.79.

Example 86
Methyl 2-(((2-(2,3-dichlorophenyl)amino)acetyl)amino) benzoate (Compound BZ)

A solution of methyl 2-((bromoacetyl)amino)benzoate (3.0 g, 11 mmol) and 2,3-dichloroaniline (4.45 g, 27.5 mmol) in anhydrous DMF (60 mL) was heated to 90°–100° C. overnight with stirring under N$_2$. The solution was cooled, poured into 500 mL of ice-water, and then extracted with 3×50 mL of ethyl acetate. The layers were separated and then the organic layer was dried (MgSO$_4$), filtered, and then concentrated. Purification by chromatography, eluting with hexane-ethyl acetate (3:1), afforded 1.01 g (26%) of the title compound, mp 136°–137° C.: $^1$H NMR (DMSO-d$_6$) δ11-19 (s, 1H), 8.49 (dd, J=8.4, J=1.2, 1H), 7.89 (d, J=8.0, J=1.6, 1H), 7.62 (ddd, J=8.8, J=7.2, J=1.6, 1H), 7.18 (ddd, J=8.4, J=8.0, J=1.2, 1H), 7.12 (t, J=8.0, 1H), 6.87 (dd, J=8.0, J=1.6, 1H), 6.6–6.52 (m, 2H), 4.02 (d, J=5.6, 2H), 3.73 (s, 3H); $^{13}$C NMR (DMSO-d$_6$) δ169.33, 167.13, 145.36, 139.34, 134.20, 131.73, 130.64, 128.44, 123.25, 120.39, 117.93, 116.62, 116.40, 109.71, 52.23, 48.16; MS (EI, m/z) 352 (M$^+$). Anal. Calcd for C$_{16}$H$_{14}$N$_2$O$_3$Cl$_2$: C, 54.41; H, 4.00; N, 7.93. Found: C, 54.32; H, 4.03; N, 7.72.

Example 87
Methyl 2-(((2-(4-(phenyl)phenyl)amino)acetyl)amino) benzoate (compound CA)

A solution of methyl 2-((bromoacetyl)amino)benzoate (3.0 g, 11 mmol) and 4-biphenylaniline (4.65 g, 27.5 mmol) in anhydrous DMF (60 mL) was heated to 90°–100° C. overnight with stirring under N$_2$. The solution was cooled, poured into 500 mL of ice-water, and extracted then with 3×50 mL of ethyl acetate. The layers were separated and the organic layer was dried (MgSO$_4$), filtered, and then concentrated. Purification by chromatography, eluting with hexane-ethyl acetate (3:1) afforded 2.28 g (57%) of the title compound, mp 143°–144° C.: $^1$H NMR (DMSO-d$_6$) δ11.43 (s, 1H), 8.63 (dd, J=8.0, J=0.8, 1H), 7.92 (dd, J=7.6, J=1.6, 1H), 7.63 (ddd, J=8.4, J=7.6, J=2.0, 1H), 7.54 (d, J=8.4, 1H), 7.53 (d, J=8.4, 1H), 7.46 (d, J=8.4, 2H), 7.37 (t, J=7.6, 2H), 7.22 (ddd, J=7.6, J=7.6, J=1.2, 1H), 7.17 (ddd, J=8.0, J=7.2, J=1.2, 1H), 6.71 (d, J=8.8, 3H), 3.89 (s, 2H), 3.74 (s, 3H); $^{13}$C NMR (DMSO-d$_6$) δ170.56, 167.04, 147.71, 140.29, 134.63, 134.27, 130.78, 129.09, 128.72, 127.29, 125.99, 125.55, 123.05, 120.10, 112.99, 52.35, 48.92; MS (EI, m/z) 360 (M$^+$). Anal. Calcd for C$_{22}$H$_{20}$N$_2$O$_3$: C, 73.31; H, 5.59; N, 7.77. Found: C, 73.27; H, 5.70; N, 7.61.

Example 88
Methyl 2-(((2-(4-(trifluoromethyl)phenyl)amino)acetyl) amino)benzoate (Compound CB)

A solution of methyl 2-((bromoacetyl)amino)benzoate (3.0 g, 11 mmol) and 4-(trifluoromethyl)aniline (4.43 g, 2.5 mL, 27.5 mmol) in anhydrous DMF (60 mL) was heated to 90°–100° C. overnight with stirring under N$_2$. The solution was cooled, poured into 500 mL of ice-water, and then extracted with 3×50 mL of ethyl acetate. The layers were separated and the organic layer was dried (MgSO$_4$), filtered, and then concentrated. Purification by chromatography, eluting with hexane-ethyl acetate (3:1) afforded 1.77 g (46%) of the title compound, mp 130°–131° C.: $^1$H NMR (DMSO-d$_6$) δ11.29 (s, 1H), 8.55 (dd, J=8.4, J=8, 1H), 7.91 (dd, J=8.0, J=1.6, 1H), 7.62 (ddd, J=9.2, J=7.6, J=2.0, 1H), 7.44 (d, J=8.8, 2H), 7.20–7.16 (m, 2H), 6.74 (d, J=8.8, 2H), 3.95 (s, 2H), 3.72 (s, 3H); $^{13}$C NMR (DMSO-d$_6$) δ169.73, 167.15, 151.20, 139.49, 134.25, 130.72, 126.30 (q, J=3.6), 123.19, 120.27, 116.42, 112.10, 52.32, 48.05; MS (EI, m/z) 352 (M$^+$). Anal. Calcd for C$_{17}$H$_{15}$N$_2$O$_3$F$_3$: C, 57.95; H, 4.29; N, 7.95. Found: C, 57.81; H, 4.33; N, 7.80.

Example 89
Methyl 4-((2-((2-fluorophenyl)amino)acetyl)amino) benzoate (Compound CC)

A solution of methyl 4-((bromoacetyl)amino)benzoate (6.0 g, 22 mmol) and aniline (6.10 g, 5.3 mL, 55 mmol) in anhydrous DMF (60 mL) was heated to 90°–100° C. overnight with stirring under N$_2$. The solution was cooled, poured into 500 mL of ice-water, and then the resulting precipitate was filtered, washed with water, and redissolved into ethyl acetate. The organic layer was washed with brine, dried over Na$_2$SO$_4$, and then concentrated in vacuo to yield 6.40 g (96%) of the title compound, mp 169°–171° C.: $^1$H NMR (DMSO-d$_6$) δ10.38 (s, 1H), 7.91 (d, J=9.2, 2H), 7.75 (d, J=8.8, 2H), 7.04 (ddd, J=9.6, J=8.4, J=1.6, 1H), 6.96 (ddd, J=7.6, J=7.6, J=0.8, 1H), 6.64–6.56 (m, 2H), 5.8 (bt, J=6.0, 1H), 3.98 (d, J=6.4, 2H), 3.81 (s, 3H); $^{13}$C NMR (DMSO-d$_6$) δ169.55, 165.77, 150.58 (d, J=235), 143.17, 136.30 (d, J=11.3), 130.40, 124.72 (d, J=3.5), 123.99, 118.59, 116.28 (d, J=7.0), 114.43 (d, J=12.0), 112.13 (d, J=3.6),51.86,46.72; MS (EI, m/z) 302 (M$^+$). Anal. Calcd for C$_{16}$H$_{15}$N$_2$O$_3$F: C, 63.57; H, 5.00; N, 9.27. Found: C, 63.22; H, 5.04; N, 9.20.

Example 90
4-(((2-(2-Fluorophenyl)amino)acetyl)amino)benzonitrile (Compound CD)

A solution of 4-((bromoacetyl)amino)benzonitrile (7.0 g, 29.3 mmol) and aniline (8.05 g, 7.0 mL, 72.4 mmol) in anhydrous DMF (60 mL) was heated to 90°–100° C. overnight with stirring under N$_2$. The solution was cooled, poured into 500 mL of ice-water, and then the resulting precipitate was filtered, washed with water, and redissolved in ethyl acetate. The organic layer was washed with brine, dried over Na$_2$SO$_4$, and then concentrated in vacuo to yield 7.30 g (92.5%) of the title compound, mp 133°–135° C.: $^1$H NMR (DMSO-d$_6$) δ10.47 (s, 1H), 7.81–7.75 (m, 4H), 7.04 (ddd, J=9.2, J=8.0, J=1.2, 1H), 6.95 (ddd, J=7.6, J=7.6, J=0.8, 1H), 6.64–6.56 (m, 2H), 5.80 (bs, 1H), 3.98 (s, 2H); $^{13}$C NMR (DMSO-d$_6$) δ169.85, 150.89 (d, J=236), 143.00, 136.31 (d, J=11.3), 133.29, 124.74 (d, J=3.5), 119.24, 119.02, 116.35 (d, J=6.4), 114.42 (d, J=17.6), 112.15 (d, J=3.5), 105.04, 46.74; MS (EI, m/z) 269 (M$^+$).

Example 91
Methyl 2-(((2-(2-(Trifluoromethyl)phenyl)amino)acetyl) amino)benzoate (Compound CE)

A solution of methyl 2-((bromoacetyl)amino)benzoate (3.0 g, 11 mmol) and 2-trifluoromethylaniline (4.37 g, 27 mmol) in anhydrous DMF (60 mL) was heated to 90°–100° C. overnight with stirring under N$_2$. The solution was cooled, poured into 500 mL of ice-water, and then extracted with 3×50 mL of ethyl acetate. The layers were separated and the organic layer was dried (MgSO$_4$), filtered, and then concentrated. Purification by chromatography, eluting with hexane-ethyl acetate (3:1), afforded 2.07 g (53%) of the title compound, mp 135°–136° C.: $^1$H NMR (DMSO-d$_6$) δ11.19 (s, 1H), 8.51 (dd, J=8.4, J=1.2, 1H), 7.90 (dd, J=8.0, J=1.6, 1H), 7.62 (ddd, J=8.8, J=7.2, J=1.6, 1H), 7.48 (dd, J=8.0, J=1.2, 1H), 7.40 (t, J=8.0, 1H), 7.18 (ddd, J=8.4, J=7.6, J=1.2, 1H), 6.77 (t, J=8.0, 1H), 6.64 (d, J=8.4, 1H), 6.26 (bt, J=5.6, 1H), 4.04 (d, J=5.6, 2H), 3.71 (s, 3H); $^{13}$C NMR (DMSO-d$_6$) δ169.52, 167.08, 144.83, 144.81, 139.38, 134.17, 133.64, 130.60, 126.35 (q, J=5.0), 123.25, 120.49, 116.67, 116.38, 112.06, 52.16, 48.15; MS (EI, m/z) 352 (M$^+$). Anal. Calcd for C$_{17}$H$_{15}$N$_2$O$_3$F: C, 57.95; H, 4.29; N, 7.95. Found: C, 57.71; H, 4.26; N, 7.90.

Example 92
Methyl 2-(((2-(4-(trifluoromethyl)phenyl)thio)acetyl) amino)benzoate (Compound CF)

To a solution of 4-(trifluoromethyl)thiophenol (1.0 g, 5.6 mmol) in 30 mL of dry THF under N$_2$ was added NaH (0.22 g, 5.61 mmol, 60% dispersion in oil). The reaction mixture was allowed to stir for ½ h at room temperature and then methyl 2((bromoacetyl)amino)benzoate was added. The reaction mixture was stirred overnight at rt, poured into 500 mL of ice-water, and then extracted with 3×50 mL of ethyl acetate. The layers were separated and the organic layer was dried (MgSO$_4$), filtered, and then concentrated. Purification by chromatography, eluting with hexane-ethyl acetate (3:1) afforded 0.58 g (60%) of the title compound, mp 74°–76° C.: $^1$H NMR (DMSO-d$_6$) δ11.18 (s, 1H), 8.29 (dd, J=8.0, J=0.8, 1H), 7.91 (dd, J=8.0, J=1.6, 1H), 7.67 (d, J=8.8, 2H), 7.61 (ddd, J=8.0, J=8.0, J=1.6, 1H), 7.56 (d, J=8.4, 2H), 7.21 (ddd, J=8.0, J=7.6, J=0.8, 1H), 4.14 (s, 2H), 3.82 (s, 3H); $^{13}$C NMR (DMSO-d$_6$) δ167.21, 166.79, 141.51, 139.06, 134.01, 130.59, 127.14, 125.75 (q, J=4.3), 123.63, 121.05, 117.64, 52.40, 36.50; MS (EI, m/z) 369 (M$^+$). Anal. Calcd for C$_{17}$H$_{14}$NO$_3$F$_3$S: C, 55.20; H, 3.82; N, 3.79. Found: C, 54.92; H, 4.10; N, 3.55.

Example 93
Ethyl 2-((2-((2-Fluorophenyl)amino)acetyl)amino)benzoate (Compound CG)

A solution of ethyl 2-((bromoacetyl)amino)benzoate (1.0 g, 3.5 mmol) and 2-fluoroaniline (1.0 g, 0.87 mL, 9 mmol) in anhydrous DMF (30 mL) was heated to 90°–100° C. overnight with stirring under N$_2$. The solution was cooled, poured into 500 mL of ice-water, and then extracted with 3×50 mL of ethyl acetate. The layers were separated, and then the organic layer was dried (MgSO$_4$), filtered and then concentrated. Purification by chromatography, eluting with hexane-ethyl acetate (3:1), afforded 0.75 g (68%) of the title compound, mp 79°–81° C.: $^1$H NMR (DMSO-d$_6$) δ11.41 (s, 1H), 8.59 (dd, J=8.4, J=0.8, 1H), 7.91 (dd, J=8.0, J=1.2, 1H), 7.61 (ddd, J=8.8, J=7.6, J=1.6, 1H), 7.17 (ddd, J=8.0, J=7.6, J=1.2, 1H), 7.08 (ddd, J=9.2, J=8.0, J=1.2, 1H), 6.93 (ddd, J=8.8, J=8.0, J=1.2, 1H), 6.63–6.54 (m, 2H), 6.34 (t, J=5.6, 1H), 4.18 (q, J=7.2, 2H), 3.90 (s, J=5.6, 1H), 1.21 (t, J=7.2, 3H); $^{13}$C NMR (DMSO-$d_6$) $\delta$170.08, 166.60, 151.12 (d, J=237), 139.59, 135.99 (d, J=11.3), 134.19, 130.67, 124.76 (d, J=3.1), 123.04, 120.08, 117.07 (d, J=6.9), 116.37, 114.49 (d, J=18.2), 112.12 (d, J=3.0), 61.13, 48.31, 13.86; MS (EI, m/z) 316 (M$^+$). Anal. Calcd for $C_{17}H_{17}N_2O_3F$: C, 64.54; H, 5.42; N, 8.86. Found: C, 64.18; H, 5.37; N, 8.83.

Example 94
Ethyl 4-((2-((2-Fluorophenyl)amino)acetyl)amino)benzoate (Compound CH)

A solution of ethyl 4-((bromoacetyl)amino) benzoate (1.0 g, 3.5 mmol) and 2-fluoroaniline (1.0 g, 0.87 mL, 9 mmol) in anhydrous DMF (30 mL) was heated to 90°–100° C. overnight with stirring under $N_2$. The solution was cooled, poured into 500 mL of ice-water, and then extracted with 3×50 mL of ethyl acetate. The layers were separated, and then the organic layer was dried (MgSO$_4$), filtered, and then concentrated. Purification by chromatography, eluting with hexane-ethyl acetate (3:1), afforded 0.58 g (52%) of the title compound, mp 169°–170° C. $^1$H NMR (DMSO-$d_6$) $\delta$10.40 (s, 1H), 7.90 (d, J=8.8, 2H), 7.75 (d, J=8.8, 2H), 7.05 (ddd, J=9.2, J=8.0, J=1.2, 1H), 6.95 (dt, 7.6, J=0.8, 1H), 6.65–6.58 (m, 2H), 5.80 (bs, 1H), 4.27 (q, J=7.2, 2H), 4.00 (d, J=8.2, 2H), 1.30 (t, J=7.2, 3H); $^{13}$C NMR (DMSO-$d_6$) $\delta$169.54, 165.28, 150.89 (d, J=236), 136.34 (d, J=12), 130.23, 124.73 (d, J=3.5), 124.27, 118.56, 116.28 (d, J=6.3), 114.40 (d, J=18.3), 112.13 (d, J=3.6), 60.40, 46.69, 14.18; MS (EI, m/z) 316 (M$^+$). Anal. Calcd for $C_{17}H_{17}N_2O_3F$: C, 64.54; H, 5.42; N, 8.86. Found: C, 64.14; H, 5.35; N, 8.83.

Example 95
Methyl 2-((2-((2-Bromophenyl)amino)acetyl)amino) benzoate (Compound CI)

A solution of methyl 2-((bromoacetyl)amino)benzoate (2.0 g, 7.35 mmol) and 2-bromoaniline (3.16 g, 18.4 mmol) in anhydrous DMF (30 mL) was heated to 90°–100° C. overnight with stirring under $N_2$. The solution was cooled, poured into 500 mL of ice-water, and then extracted with 3×50 mL of ethyl acetate. The layers were separated and the organic layer was dried (MgSO$_4$), filtered, and then concentrated. Purification by chromatography, eluting with hexane-ethyl acetate (3:1), afforded 0.81 g (30%) of the title compound, mp 89°–91° C.: $^1$H NMR (DMSO-$d_6$) $\delta$11.19 (s, 1H), 8.52 (dd, J=8.4, J=0.8, 1H), 7.90 (dd, J=8.0, J=1.6, 1H), 7.62 (ddd, J=8.8, J=7.6, J=1.6, 1H), 7.47 (dd, J=8.0, J=1.6, 1H), 7.20–7.14 (m, 2H), 6.60 (ddd, J=8.4, J=8.0, J=1.2, 1H), 6.53 (dd, J=8.4, J=1.6, 1H), 6.06 (bt, J=5.6, 1H), 4.00 (d, J=5.6, 2H), 3.73 (s, 3H); $^{13}$C NMR (DMSO-$d_6$) $\delta$169.70, 167.01, 144.53, 139.32, 134.16, 132.36, 130.68, 128.67, 123.21, 120.40, 118.35, 116.66, 111.51, 109.04, 52.26, 48.47; MS (EI, m/z) 363 (M$^+$). Anal. Calcd for $C_{16}H_{15}N_2O_3Br$: C, 52.91; H, 4.16; N, 7.71. Found: C, 52.22; H, 4.05; N, 7.40.

Example 96
Methyl 4-(((2-(4-(Trifluoromethyl)phenyl)amino)acetyl) amino)benzoate (Compound CJ)

A solution of methyl 4-((bromoacetyl)amino)benzoate (1.5 g, 5.51 mmol) and 4-(trifluoromethyl)aniline (2.22 g, 13.77 mmol) in anhydrous DMF (30 mL) was heated to 90°–100° C. overnight with stirring under $N_2$. The solution was cooled, poured into 500 mL of ice-water, and then the resulting precipitate was filtered, washed with water, and dried under a vacuum desiccator overnight to yield 1.78 g (92%) of the title compound, mp 204°–206° C.: $^1$H NMR (DMSO-$d_6$) $\delta$10.43 (s, 1H), 7.92 (d, J=8.8, 2H), 7.74 (d, J=8.8, 2H), 7.40 (d, J=8.4, 2H), 6.80 (bt, J=5.6, 1H), 6.70 (d, J=8.4, 2H), 4.00 (d, J=5.6, 2H), 3.81 (s, 3H); $^{13}$C NMR (DMSO-$d_6$) $\delta$169.24, 165.80, 151.43, 143.22, 130.32, 125.30 (q, J=268), 126.22 (q, J=3.5), 124.06, 118.59, 116.00 (q, J=31.7), 111.70, 51.88, 46.48; MS (EI, m/z) 352 (M$^+$).

Example 97
Methyl 4-(((2-(2-(Trifluoromethyl)phenyl)amino)acetyl) amino)benzoate (Compound CK)

A solution of methyl 4-((bromoacetyl)amino)benzoate (1.5 g, 5.51 mmol) and 2-(trifluoromethyl)aniline (2.0 g, 12.4 mmol) in anhydrous DMF (30 mL) was heated to 90°–100° C. overnight with stirring under $N_2$. The solution was cooled, poured into 500 mL of ice-water, and then the resulting precipitate was filtered, washed with water, and dried under a vacuum desiccator overnight to yield 1.38 g (71%) of the title compound, mp 174°–176° C.: $^1$H NMR (DMSO-$d_6$) $\delta$10.53 (dd, J=7.2, J=2.0, 2H), 7.73 (dd, J=7.2, J=2.0, 2H), 7.46–7.40 (m, 2H), 6.74 (t, J=7.2, 1H), 6.67 (d, J=8.4, 1H), 5.78 (bt, J=5.6, 1H), 4.07 (d, J=5.6, 2H), 3.82 (s, 3H); $^{13}$C NMR (DMSO-$d_6$) $\delta$168.70, 165.74, 148.99, 143.09, 133.64, 130.35, 126.23, 124.05, 118.50, 115.77, 112.20, 51.89, 46.32; MS (EI, m/z) 352 (M$^+$).

Example 98
4-(((2-(4-(Trifluoromethyl)phenyl)amino)acetyl)amino) benzoic Acid (Compound CL)

A solution of 4-((bromoacetyl)amino)benzoic acid (1.5 g, 5.8 mmol) and 4-(trifluoromethyl)aniline (2.5 g, 15.51 mmol) in anhydrous DMF (30 mL) was heated to 90°–100° C. overnight with stirring under $N_2$. The solution was cooled, poured into 500 mL of ice-water, and then a solution at 5% KOH was added until the pH of the solution was 10. The solution was extracted with $CH_2Cl_2$ (3×150 mL), the aqueous layer was acidified to pH=3 using 2N HCl, and then the precipitate which formed was filtered, washed with water, and dried in a vacuum desiccator overnight to yield 1.49 g (76%) of the title compound, mp 222°–223° C. (decomp): $^1$H NMR (DMSO-$d_6$) $\delta$12.72 (s, 1H), 10.39 (s, 1H), 7.89 (d, J=8.8, 2H), 7.72 (d, J=8.4, 2H), 7.40 (d, J=8.8, 2H), 6.77 (bt, J=6.0, 1H), 6.70 (d, J=8.8, 2H) 4.00 (d, J=6, 2H); $^{13}$C NMR (DMSO-$d_6$) $\delta$169.08, 166.83, 151.42, 142.81, 130.39, 126.19 (q, J=3.5), 125.20, 118.45, 111.67, 46.43; MS (EI, m/z) 338 (M$^+$).

Example 99
4-(((2-(2-(Trifluoromethyl)phenyl)amino)acetyl)amino) benzoic Acid (Compound CM)

A solution of 4-((bromoacetyl)amino)benzoic acid (1.5 g, 5.81 mmol) and 2-trifluoromethylaniline (2.0 g, 12.41 mmol) in anhydrous DMF (30 mL) was heated to 90°–100° C. overnight with stirring under $N_2$. The solution was cooled, poured into 500 mL of ice-water, and then a solution of 5% KOH was added until the pH of the solution was 10. The solution was extracted with $CH_2Cl_2$ (3×150 mL), the aqueous layer was acidified to pH=3 using 2N HCl, and then the precipitate which formed was filtered, washed with water, and dried in a vacuum desiccator overnight to yield 1.37 g (73%) of the title compound as a pale orange powder, mp 188°–190° C.: $^1$H NMR (DMSO-$d_6$) $\delta$12.72 (s, 1H), 10.50 (s, 1H), 7.90 (d, J=8.4, 2H), 7.71 (d, J=8.8, 2H), 7.46–7.40 (m, 2H), 6.74 (t, J=8.4, 1H), 6.67 (d, J=8.4, 1H), 4.08 (d, J=5.6, 2H); $^{13}$C NMR (DMSO-$d_6$) $\delta$168.62, 166.85, 145.00, 142.73, 133.65, 130.47, 126.34 (q, J=3.6), 125.27, 118.80, 118.39, 115.77, 112.21, 46.31; MS (EI, m/z) 338 (M$^+$).

Example 100
4-((2-((2-Fluorophenyl)amino)acetyl)amino)-1-butoxybenzene (Compound CN)

A solution of 4-((bromoacetyl)amino)-1-butoxybenzene (1.0 g, 3.5 mmol) and 2-fluoroaniline (1.0 g, 0.87 mL, 8.8 mmol) in anhydrous DMF (30 mL) was heated to 90°–100° C. overnight with stirring under $N_2$. The solution was cooled, poured into 500 mL of ice-water, and then extracted with $CH_2Cl_2$ (3×50 mL). The layers were separated and the organic layer was dried ($MgSO_4$), filtered and then concentrated to an oily residue. Purification by chromatography, eluting with hexane-ethyl acetate (2:1), afforded 0.50 g (45%) of the title compound, mp 92°–94° C.: 1H NMR (DMSO-$d_6$) $\delta$9.86 (s, 1H), 7.47 (d, J=8.8, 2H), 7.04 (ddd, J=9.6, J=8.0, J=1.2, 1H), 6.94 (dt, J=8.0, J=0.8, 1H), 6.86 (d, J=9.6, 2H), 6.63–6.58 (m, 2H), 5.73 (bt, J=2.0, 1H), 3.90 (q, J=6.0, 2H), 3.46 (s, 2H), 1.68–1.64 (m, 2H), 1.44–1.40 (m, 2H), 0.91 (t, J=5.6, 3H); $^{13}$C NMR (DMSO-$d_6$) $\delta$168.24, 154.69, 150.90 (d, J=236), 136.46, 131.79, 124.73 (d, J=3.5), 120.79, 116.22 (d, J=6.3), 114.48 (d, J=5.6), 114.33 (d, J=126), 112.11 (d, J=3.6), 67.21, 46.57, 30.75, 18.70, 13.66; MS (EI, m/z) 316 ($M^+$).

Example 101
4-((-2-((2-Fluorophenyl)amino)acetyl)amino)benzyl cyanide

A solution of 4-((bromoacetyl)amino)benzyl cyanide (8.5 g, 33.6 mmol) and 2-fluoroaniline (9.03 g, 81.3 mmol) in anhydrous DMF (60 mL) was heated to 90°–100° C. for 2 days with stirring under $N_2$. The solution was cooled, poured into 500 mL of ice-water, and then extracted with $CH_2Cl_2$ (200 mL). The separated organic layer was dried ($MgSO_4$) and filtered, a small amount of silica gel was added to the $CH_2Cl_2$ solution, and then the mixture was concentrated. Purification by chromatography, eluting with hexane-ethyl acetate (2:1), afforded 7.0 g (73.5%) of the title compound, mp 111°–113° C.: 1H NMR (DMSO-$d_6$) $\delta$10.09 (s, 1H), 7.61 (d, J=8.4, 2H), 7.27 (d, J=8.8, 2H), 7.05 (ddd, J=9.6, J=8.0, J=1.6, 1H), 6.94 (t, J=7.1, 1H), 6.63–6.58 (m, 2H), 5.76 (bt, J=6.0, 1H); 3.96 (s, 2H), 3.93 (d, J=6.0, 2H); $^{13}$C NMR (DMSO-$d_6$) $\delta$168.92, 150.87 (d, J=236), 138.18, 136.37 (d, J=11.0), 128.47, 125.85, 124.72 (d, J=3.0), 119.61, 119.32, 116.24 (d, J=6.8), 114.37 (d, J=17), 112.13, 46.62, 21.79; MS (EI, m/z) 283 ($M^+$).

Example 102
4-((-2-((2-Fluorophenyl)amino)acetyl)amino)-1-nitrobenzene (Compound CO)

A solution of 4-((bromoacetyl)amino)nitrobenzene (12.0 g, 46.3 mmol) and 2-fluoroaniline (11.0 g, 102 mmol) in anhydrous DMF (60 mL) was heated to 90°–100° C. for 2 days with stirring under $N_2$. The solution was cooled, poured into 500 mL of ice-water, and then extracted with $CH_2Cl_2$ (200 mL). The organic layer was dried ($MgSO_4$) and filtered, a small amount of silica gel was added to the $CH_2Cl_2$ solution, and then the mixture was concentrated. Purification by chromatography, eluting with hexane-ethyl acetate (3:1), afforded 8.54 g (63.7%) of the title compound as yellow crystals, mp 150°–153° C.; $^1$H NMR (DMSO-$d_6$) $\delta$10.65 (s, 1H), 8.22 (d, J=9.2, 2H), 7.86 (d, J=9.2, 2H), 7.04 (ddd, J=9.6, J=8.4, J=1.6, 1H), 6.94 (dt, J=7.2, J=1.2, 1H), 6.65–6.61 (m, 2H), 5.80 (bs, 1H), 4.02 (s, 2H); $^{13}$C NMR (DMSO-$d_6$) $\delta$170.06, 150.91 (d, J=236), 144.99, 142.23, 136.31 (d, J=11.3), 124.98, 124.75 (d, J=3.5), 118.90, 116.36 (d, J=6.4), 114.44 (d, J=17.6), 112.17 (d, J=14.0), 46.79; MS (EI, m/z) 289 ($M^+$). Anal. Calcd for $C_{14}H_{12}N_3O_3F$: C, 58.12; H, 4.18; N, 14.53. Found: C, 58.04; H, 4.20; N, 14.36.

Example 103
4-((2-((2-Fluorophenyl)amino)acetyl)amino)phenol (Compound CP)

A solution of 4-((bromoacetyl)amino)-1-((tert-butyldimethyl)silyl)oxy)benzene (9.0 g, 26.1 mmol) and 2-fluoroaniline (7.0 g, 63.0 mmol) in anhydrous DMF (30 mL) was heated to 90°–100° C. overnight with stirring under $N_2$. The solution was cooled, poured into 500 mL of ice-water, and then extracted with $CH_2Cl_2$ (200 mL). The separated organic layer was dried ($MgSO_4$), filtered, a small amount of silica gel was added to the $CH_2Cl_2$ solution, and then the mixture was concentrated. Purification by chromatography, eluting with hexane-ethyl acetate (3:1), afforded a brown oil. The oil was triturated with ether and the resulting pale-greenish solid was filtered, washed with cold ether, and then dried to afford 2.60 g (38%) of the title compound, mp 143°–146° C.: 1H NMR (DMSO-$d_6$) $\delta$9.75 (s, 1H), 9.19 (s, 1H), 7.36 (d, J=8.4, 2H), 7.04 (ddd, J=9.2, J=8.0, J=1.2, 1H), 6.96 (t, J=7.6, 1H) 6.68 (d, J=8.8, 2H, 6.66–6.56 (m, 2H), 5.71 (bt, J=6.4, 1H), 3.86 (d, J=6.4, 2H); $^{13}$C NMR (DMSO-$d_6$) $\delta$170.51, 155.88, 153.40 (d, J=236), 138.91 (d, J=47.6), 132.89, 127.23 (d, J=14), 123.54, 118.70 (d, J=28), 117.53, 116.85 (d, J=70), 114.61 (d, J=14), 49.05; MS (EI, m/z) 260 ($M^+$).

Example 104
Methyl 4-((2-((2-Fluorophenyl)amino)acetyl)amino)phenyl Acetate (Compound CQ)

A solution of 4-((bromoacetyl)amino)phenylacetic acid (2.0 g, 7.35 mmol) and 2-fluoroaniline (2.04 g, 18.38 mmol) in anhydrous DMF (30 mL) was heated to 90°–100° C. overnight with stirring under $N_2$. The solution was cooled, poured into 500 mL of ice-water, and then extracted with $CH_2Cl_2$ (2×150 mL). The layers were separated, and then the organic layer was dried ($MgSO_4$), filtered, and then concentrated. The resulting oil was dissolved in ether, and then an etheral solution of diazomethane was added dropwise with stirring until the ether solution turned slightly yellow and no more bubbling occurred. The solution was filtered and then the filtrate was concentrated to give an oil. A small amount of silica gel was added together with a small amount of $CH_2Cl_2$, and then the mixture was concentrated. Purification by chromatography, eluting with hexane-ethyl acetate (2:1), afforded 1.16 g (50%) of the title compound, mp 125°–130° C.: $^1$H NMR (DMSO-$d_6$) $\delta$10.01 (s, 1H), 7.53 (d, J=8.4, 2H), 7.18 (d, J=8.4, 2H), 7.04 (ddd, J=9.6, J=8.0, J=1.2, 1H), 6.96 (dt, J=8.4, J=1.2, 1H), 6.63–6.57 (m, 2H), 5.73 (bs, 1H), 3.91 (d, J=6.0, 2H), 3.61 (s, 5H); $^{13}$C NMR (DMSO-$d_6$) $\delta$171.67, 168.74, 150.88 (d, J=235), 137.51, 136.37 (d, J=11), 129.60, 129.18, 124.72 (d, J=2.8), 118.23, 116.23 (d, J=6.3), 114.35 (d, J=17.6), 112.10 (d, J=3.5), 51.61, 46.61, 1 $CH_2$ peak coincident under DMSO-$d_6$; MS (EI, m/z) 316 ($M^+$). Anal. Calcd for $C_{17}H_{17}N_2O_3F$: C, 64.64; H, 5.42; N, 8.86. Found: C, 64.09; H, 5.53; N, 8.52.

Example 105
4,5-Difluoro-2-((bromoacetyl)amino)benzoic Acid

A solution of 4,5-difluoro-2-aminobenzoic acid (20.0 g, 115.5 mmol) in a mixture of anhydrous DMF (50 mL) and anhydrous dioxane (50 mL) was cooled to 0° C. under $N_2$ using an ice-bath. Bromoacetyl bromide (23.3 g, 10.1 mL, 115.5 mmol) was added dropwise, keeping the internal temperature between 0° and 5° C. over a ¾ h period. After the addition of bromide was completed, the solution was warmed to rt, stirred overnight, and then the solution was slowly poured into 200 mL of ice-water. The resulting precipitate was filtered, washed with water, and then dried in a vacuum desiccator overnight to afford 31.24 g (92%) of the title compound as a white solid, mp 177°–180° C.: $^1$H NMR (DMSO-d$_6$) δ14.17 (bs, 1H), 11.66 (s, 1H), 8.47 (dd, J=13.6, J=7.6, 1H), 7.97 (dd, J=11.2, J=9.2, 1H), 4.28 (s, 2H); $^{13}$C NMR (DMSO-d$_6$) δ167.55, 165.45, 151.99 (dd, J=249, J=12.9), 144.53 (dd, J=242, J=12.9), 137.58 (dd, J=7.5, 1=3), 119.75 (d, J=18.9), 114.18 (t, J=3), 108.96 (d, J=23.5), 30.43; MS (EI m/z) 293 (M$^+$).

Example 106
4,5-Difluoro-2-((2-(phenylamino)acetyl)amino)benzoic Acid

A solution of 4,5-difluoro-2-((bromoacetyl)amino) benzoic acid (31.0 g 105.4 mmol) and aniline (24 mL, 24.5 g, 263.4 mmol) in anhydrous DMF (100 mL) was heated to 95°–100° C. overnight with stirring under N$_2$. The solution was cooled, poured into 500 mL of ice-water, and then a solution of 5% KOH was added until the pH of the solution was 10. The solution was extracted with 3×150 mL of CH$_2$Cl$_2$, and then the aqueous layer was separated and acidified to pH=3 using 2N HCl. The yellow precipitate which formed was filtered, washed with water, and then dried in a vacuum desiccator to yield 32.01 g (99%) of the title compound as a light-yellow solid, mp 124°–126° C.: $^1$H NMR (DMSO-d$_6$) δ12.10 (s, 1H), 8.75 (dd, J=14.0, J=7.6, 1H), 7.86 (dd, J=11.6, J=1.2, 1H), 7.09 (t, J=7.2, 2H), 6.63–6.40 (m, 4H), 3.85 (s, 2H); $^{13}$C NMR (DMSO-d$_6$) δ171.40, 167.44, 152.18 (dd, J=249, J=12.7), 148.02, 144.02 (dd, J=242, J=12.6), 138.18 (dd, J=10.6, J=2.1), 129.01, 119.66 (d, J=19), 117.22, 113.10, 112.48, 108.21 (d, J=23), 48.82; MS (EI, m/z) 306 (M$^+$).

Example 107
(2-Bromoacetyl)amino benzene

Aniline (19.4 g, 0.043 mol) was dissolved in the mixture of DMF (25 mL) and dioxane (25 mL). The solution was cooled to +5° C. and bromoacetyl bromide (3.8 mL=8.7 g, 100 mol %) was added dropwise over 30 min. The reaction mixture was warmed to room temperature and stirred for 7 h. The mixture was poured into ice-water, and the white crystalline compound which precipitated was filtered, washed several times with cold water, and then air dried for 24 h, giving 6.2 g (68%) of title compound: $^1$H NMR (CDCl$_3$) δ8.20 (bs, 1H), 7.54 (dd, J=8.8, J=1.2, 2H), 7.37 (t, J=7.2, 1H), 7.18 (t, J=8, 1H), 4.03 (s, 2H): $^{13}$C NMR (CDCl$_3$) δ163.35, 136.88, 129.21, 129.18, 129.11, 125.21, 120.03, 29.47; MS (EI, m/z) 213 (M$^+$).

Example 108
2-((2-(Fluorophenyl)amino)acetyl)aminobenzene (Compound CR)

To a solution of (2-bromoacetyl)aminobenzene (1 g, 4.7 mmol) in 20 mL of DMF was added 2-fluoroaniline (0.9 mL, 200 mol %). The reaction mixture was stirred at 93°–94° C. for 7 h, cooled to +40° C., and then poured into ice-water. The oily mixture was allowed to stand for 20 h, and the light crystalline compound which precipitated was filtered and air dried for several days. Purification by column chromatography (eluent EtOAc/Hex, 1:1) gave 0.5 g (44%) of the title compound as a light crystalline compound after drying for 5 h under high vacuum, mp 91.8°–93.2° C.: $^1$H NMR (CDCl$_3$) δ10.03 (s, 1H), 7.60 (dd, J=8.8, J=3.0, 2H), 7.30 (t, J=7.6; 2H), 7.08–7.02 (m, 2H), 6.96 (pseudo t J=8.0, 1H), 6.65–6.55 (m, 2H), 5.76 (bs, 1H), 3.93 (s, 2H); $^{13}$C NMR (CDCl$_3$) δ168.74, 151.17 (d, J=239), 138.73, 136.34 (d, J=11.4), 128.65, 124.69 (d, J=31), 123.26, 119.20, 116.23 (d, J=6.9), 114.12 (d, J=18.2), 112.12 (d, J=2.0), 46.64; MS (EI, m/z) 244 (M$^+$).

Example 109
4-(Tetrazol-5-yl)-1-(((2-(2-fluorophenyl)amino)acetyl)amino)benzene (Compound CS)

4-(((2-(2-Fluorophenyl)amino)acetyl)amino)benzonitrile (0.63 g, 2.34 mmol) was dissolved in DMF (10 mL) and to this solution was added 0.2 g (130 mol %) of NaN$_3$,0.16 g (130 mol %) of NH$_4$Cl, and a catalytic amount of LiCl. This mixture was heated to 125° C. in the oil bath and stirred at this temperature for 30 h before TLC analysis showed the disappearance of the starting material. The reaction mixture was poured into ice-water, acidified to pH=3, and then the light crystalline compound which precipitated was filtered, washed several times with cold water, washed several times with ether, and then air dried to afford 0.38 g (42%) of a light crystalline compound, mp 244.6°–246° C. (decomp): $^1$H NMR (DMSO-d$_6$) δ10.36 (s, 1H), 7.98 (d, J=8.8, 2H), 7.84 (d, J=8.8, 2H), 7.08–6.95 (m, 2H), 6.66–6.57 (m, 2H), 5.81 (bs, 1H), 3.98 (s, 2H); $^{13}$C NMR (DMSO-d$_6$) δ169.45, 150.90 (d, J=237.86), 141.38, 136.36 (d, J=10.56), 127.93, 127.75, 124.75 (d, J=2.0), 119.49, 119.23, 116.32 (d, J=6.34), 114.42 (d, J=17.7), 112.17 (d, J=2.8), 46.72; MS (EI, m/z) 312 (M$^+$).

7. EXAMPLE: ANTIHYPERGLYCEMIC ACTIVITY

7.1 IN VIVO ACTIVITY OF THE ANILINE DERIVATIVES

Representative aniline derivatives of the present invention were tested in the in vivo model described below.

7.7.1 PROTOCOL

Genetically altered obese diabetic mice (designated C57BL/Ks-db/db) were purchased from the Jackson Laboratory (Bar Harbor, Me., USA), and served as experimental animals. Male animals between the ages of 8–9 weeks were employed in the studies described here. Animals were housed (4 mice/cage) under standard laboratory conditions at 22° C. and provided with Purina rodent chow and water ad libitum. Prior to treatment, blood was collected from the tail vein of each animal. Mice that had plasma glucose levels between 350 and 600 mg/dL were used in these studies. Each treatment group consisted of eight mice that were distributed so that mean glucose levels were equivalent in each group at the start of the study. Diabetic designated C57BL/Ks-db/db mice were dosed orally by gavage once daily for 1 or 2 days with either vehicle, the experimental compound administered at 100 mg/kg/day (unless otherwise noted), or metformin (250 mg (1510 mmol) /kg/day). Compounds were delivered in aqueous vehicle formulation, including components such as cremephor, HPMC, RH40, 0.25% (w/v) carboxymethylcellulose, 1% (v/v) Tween™ 60, and up to 10% (v/v) dimethyl sulfoxide (DMSO) in a volume of 10 mL/kg. Blood was sampled from the tail vein three hours post-dosing, and analyzed for plasma glucose levels. Individual body weights and mean food consumption (each cage) were also measured after 24–27 h.

The aniline derivatives tested for antihyperglycemic activity were prepared as described above in Sections 5.1 or 6.2 above. Metformin (1,1-dimethylbiguanide) was purchased from Sigma Chemical Co. (St. Louis, Mo., USA; catalog #D-5035).

Plasma glucose levels were determined colorimetrically using a glucose oxidase assay (Sigma Chemical Co.; Sigma catalog #325). Significant differences between groups (comparing compound-treated to vehicle-treated) were evaluated using analysis of variance and Fisher's post-hoc test.

The following compounds were evaluated in diabetic C57BL/Ks-db/db animals for their ability to lower glucose:

2-(2-(((2-fluorophenyl)amino)acetyl)amino)benzoic acid (Compound AB);

2-(2-(((3-fluorophenyl)amino)acetyl)amino)benzoic acid (Compound AC);

2-(2-(((4-fluorophenyl)amino)acetyl)amino)benzoic acid (Compound AD);

2-(2-(((4-(phenyl)phenyl)amino)acetyl)amino)benzoic acid (Compound AE);

2-(2-(((4-methoxyphenyl)amino)acetyl)amino)benzoic acid (Compound AF);

2-(2-((phenylamino)acetyl)amino)-5-bromobenzoic acid (Compound BF);

2-(2-((phenylamino)acetyl)amino)-6-fluorobenzoic acid (Compound AV);

2-(2-(((4-(trifluoromethyl)phenyl)amino)acetyl)amino) benzoic acid (Compound AG);

2-(2-(((2,3-dimethylphenyl)amino)acetyl)amino)benzoic acid (Compound AH);

2-(2-(((2,3-dichlorophenyl)amino)acetyl)amino)benzoic acid (Compound AI);

2-(2-(((2-methoxyphenyl)amino)acetyl)amino)benzoic acid (Compound AJ);

2-(2-((phenylamino)acetyl)amino)benzoic acid (Compound AK);

2-(2-(((2-(trifluoromethyl)phenyl)amino)acetyl)amino) benzoic acid (Compound AL);

2-(2-(((2-fluorophenyl)amino)acetyl)amino)-5-fluorobenzoic acid (Compound AU);

2-(2-(((2-fluorophenyl)amino)acetyl)amino)-6-fluorobenzoic acid (Compound AW);

2-(2-(((2-fluorophenyl)amino)acetyl)amino)-4-chlorobenzoic acid (Compound AZ);

2-(2-(((2-fluorophenyl)amino)acetyl)amino)-5-bromobenzoic acid (Compound BG);

2-(2-(((2-fluorophenyl)amino)acetyl)amino)-5-chlorobenzoic acid (Compound BB);

((2-fluorophenyl)amino)acetic acid (Compound BK);

2-(2-(((2-fluorophenyl)amino)acetyl)amino)-5-methoxybenzoic acid (Compound BE);

4-(2-(((2-fluorophenyl)amino)acetyl)amino)benzoic acid (Compound AP);

2-(2-(((4-(trifluoromethyl)phenyl)thio)acetyl)amino) benzoic acid (Compound AN);

methyl 2-(2-(((2-fluorophenyl)amino)acetyl)amino) benzoate (Compound BL);

1,2-bis((2-carboxyphenyl)amino)ethane (Compound BM);

4-(2-(((2-fluorophenyl)amino)acetyl)amino)phenylacetic acid (Compound BO);

2-((2-carboxyphenyl)amino)-2-((2-fluorophenyl)amino) ethane (Compound BN);

2-(2-(((2-fluorophenyl)thio)acetyl)amino)benzoic acid (Compound AO);

4-(2-(((2-fluorophenyl)amino)acetyl)amino) benzyltetrazole (Compound BQ);

3-(2-(((2-fluorophenyl)amino)acetyl)amino)pyridine (Compound BR);

Methyl 2-((2-(phenylamino)acetyl)amino)benzoate (Compound BY);

Methyl 2-(((2-(4-(phenyl)phenyl)amino)acetyl)amino) benzoate (Compound CA);

Methyl 2-(((2-(4-(trifluoromethyl)phenyl)amino)acetyl) amino)benzoate (Compound CB);

Methyl 2-(((2-(2,3-dichlorophenyl)amino)acetyl)amino) benzoate (Compound BZ);

Methyl 4-((2-((2-fluorophenyl)amino)acetyl)amino) benzoate (Compound CC);

Methyl 2-(((2-(2-(Trifluoromethyl)phenyl)amino)acetyl) amino)benzoate (Compound CE);

Methyl 4-(((2-(4-(Trifluoromethyl)phenyl)amino)acetyl) amino)benzoate (Compound CJ);

Methyl 4-(((2-(2-(Trifluoromethyl)phenyl)amino)acetyl) amino)benzoate (Compound CK);

4-(((2-(4-(Trifluoromethyl)phenyl)amino)acetyl)amino) benzoic Acid (Compound CL);

4-(((2-(2-(Trifluoromethyl)phenyl)amino)acetyl)amino) benzoic Acid (Compound CM);

Methyl 2-(((2-(4-(trifluoromethyl)phenyl)thio)acetyl) amino)benzoate (Compound CF);

Ethyl 2-((2-((2-Fluorophenyl)amino)acetyl)amino) benzoate (Compound CG);

Ethyl 4-((2-((2-Fluorophenyl)amino)acetyl)amino) benzoate (Compound CH);

Methyl 2-((2-((2-Bromophenyl)amino)acetyl)amino) benzoate (Compound CI);

2-((2-(Fluorophenyl)amino)acetyl)aminobenzene (Compound CR);

4-((2-((2-Fluorophenyl)amino)acetyl)amino)phenol (Compound CP);

4-(Tetrazol-5-yl)-1-(((2-(2-fluorophenyl)amino)acetyl) amino)benzene (Compound CS); and 4-((2-((2-Fluorophenyl)amino)acetyl)amino)-1-butoxybenzene (Compound CN).

7.1.2 RESULTS FROM IN VIVO TESTING

The compounds were evaluated in a series of experiments as described in Section 7.1.1. The results are summarized in Tables 1 and 1a.

In the experiments in which a single daily dose of test compound was administered orally to diabetic C57BL/Ks-db/db mice for 1–2 days at a dosage level of 100 mg/kg (Table 1), or 100 or 250 mg/kg, as indicated (Table 1a), the following compounds resulted in statistically significant reductions in plasma glucose relative to vehicle control at either the 3 or 27 h after oral administration: Compound AB, Compound AE, Compound AG, Compound AK, Compound BE, Compound AP, Compound AW, Compound AN, Compound BL, Compound CB, Compound CL, Compound CM, Compound CN, and Compound CR. Compounds that trended to significant reductions, i.e., p value greater than 0.05 but less than 0.1, included Compound AF, Compound AU, Compound AL, Compound BB, Compound CJ and Compound CP.

In experiments in which the vehicle control values did not fluctuate significantly during the experiment, the maximum decline in glucose seen with 100 mg/kg doses of experimental compound was 113.8 mg/dL with Compound AN (27 h), and with 250 mg/kg doses of experimental compound was 135.5 mg/dL with Compound CL (3 h). By comparison, the known antihyperglycemic agent metformin, given at 250 mg/kg, caused reductions in plasma glucose levels ranging from 72.9 to 242.6 mg/dL.

TABLE 1

Effects of Aniline derivatives on Blood Glucose in Diabetic db/db Mice

| Exp. No. | Treatment | Change in Glucose (mg/dL) 3 h | P Value* | Change in Glucose (mg/dL) 27 h | P Value* |
|---|---|---|---|---|---|
| 1 | Metformin | −102.4 | 0.0001 | −116.4 | 0.0002 |
|   | Compound AB | −29.1 | 0.057 | −61.3 | 0.023 |
| 2 | Metformin | −197.1 | 0.0001 | N.T. | — |
|   | Compound AC | −7.5 | N.S. | N.T. | — |
| 3 | Metformin | −56.6[1] | 0.0001 | N.T. | — |
|   | Compound AD | 43.3[1] | N.S. | N.T. | — |
|   | Compound AF | 31.6[1] | 0.072 | N.T. | — |
| 4 | Metformin | −48.7[1] | 0.0001 | −142.1 | 0.0001 |
|   | Compound AE | −87.8[1] | 0.0001 | N.T. | — |
|   | Compound BN | 71.4[1] | N.S. | N.T. | — |
| 5 | Metformin | −62.8[1] | 0.0063 | N.T. | — |
|   | Compound BF | 24.1[1] | N.S. | N.T. | — |
|   | Compound AV | 41.8[1] | N.S. | N.T. | — |
| 6 | Metformin | −202.3 | 0.0001 | −200.4 | 0.0001 |
|   | Compound AG | −37.7 | N.S. | −112.7 | 0.018 |
| 7 | Metformin | −77.5 | 0.0007 | −62.9 | 0.0039 |
|   | Compound AH | −17.5 | N.S. | 15.1 | N.S. |
|   | Compound AI | 9.2 | N.S. | 12.4 | N.S. |
| 8 | Metformin | −104.0 | 0.032 | N.T. | — |
|   | Compound AJ | 6.3 | N.S. | N.T. | — |
| 9 | Metformin | −194.3 | 0.0001 | N.T. | — |
|   | Compound AK | −61.1 | 0.004 | −212.4[2] | 0.032 |
|   | Compound BE | −61.1 | 0.0041 | −160.0[2] | N.S. |
|   | Compound AP | −73.5 | 0.0018 | −131.8[2] | N.S. |
| 10 | Metformin | −71.0[1] | 0.009 | −37.3[1] | 0.0038[1] |
|    | Compound AU | 63.6[1] | N.S. | 2.4[1] | 0.056[1] |
|    | Compound AW | 68.4[1] | N.S. | −40.5[1] | 0.003[1] |
| 11 | Metformin | −85.7 | 0.026 | −77.7 | 0.08 |
|    | Compound AZ | −12.4 | N.S. | −19.2 | N.S. |
|    | Compound BG | 96.5 | N.S. | 29.6 | N.S. |
| 12 | Metformin | −134.3 | 0.0001 | −112.9 | 0.042 |
|    | Compound AL | −14.7 | 0.053 | 3.2 | N.S. |
|    | Compound BB | −8.0 | 0.061 | 14.9 | N.S. |
| 13 | Metformin | −169.5 | 0.0038 | −244.2 | 0.0001 |
|    | Compound BK | −15.8 | N.S. | 22.3 | N.S. |
| 14 | Metformin | −131.9 | 0.0006 | −178.0 | 0.0001 |
|    | Compound AN | −22.6 | N.S. | −113.8 | 0.00074 |
| 15 | Metformin | −21.8 | 0.0026 | −118.6 | 0.0011 |
|    | Compound BL | 2.3 | N.S. | −69.2 | 0.032 |
| 16 | Metformin | −123.3 | 0.0024 | −183.1 | 0.0001 |
|    | Compound AO | 34.3 | N.S | 30.4 | N.S. |
|    | Compound BQ | −37.8 | N.S. | 18.3 | N.S. |
| 17 | Metformin | −98.7 | 0.1490 | −103.7 | 0.0008 |
|    | Compound BM | 58.9 | N.S. | −7.0 | N.S. |
| 18 | Metformin | −87.5 | 0.0068 | −139.6 | 0.0242 |
|    | Compound BR | † | — | † | — |

TABLE 1a

Effects of Aniline derivatives on Blood Glucose in Diabetic db/db Mice

| Exp. No. | Treatment | Change in Glucose (mg/dL) 3 h | P Value* | Change in Glucose (mg/dL) 27 h | P Value* | Dose (mg/kg) |
|---|---|---|---|---|---|---|
| 19 | Metformin | −143.5 | <0.001 | −180.6 | <0.001 | 250 |
|    | Compound BY | 7.7 | N.S. | −32.6 | N.S. | 100 |
|    | Compound CA | −47.8 | N.S. | −9.4 | N.S. | 100 |
|    | Compound CB | −50.5 | N.S. | −65.6 | N.S. | 100 |
|    | Compound BZ | 30.0 | N.S. | −1.4 | N.S. | 100 |
| 20 | Metformin | −138.8 | 0.0018 | −206.9 | <0.0001 | 250 |
|    | Compound CC | −5.5 | N.S. | −32.4 | N.S. | 100 |
| 21 | Metformin | −169.8 | <0.0001 | −172.9 | <0.0001 | 250 |
|    | Compound CB | −75.3 | 0.0082 | N.T. | — | 250 |
|    | Compound CE | 16.8 | N.S. | 5.8 | N.S. | 100 |
| 22 | Metformin | −226.9 | <0.0001 | −187.8 | <0.0001 | 250 |
|    | Compound CJ | −90.6 | 0.0637 | −84.3 | 0.0956 | 250 |
|    | Compound CK | −13.1 | N.S. | −54.2 | N.S. | 250 |
|    | Compound CL | −135.5 | 0.0041 | N.T. | — | 250 |
|    | Compound CM | −75.4 | 0.1406 | −158.4 | 0.0005 | 250 |
| 23 | Metformin | −207.0 | <0.0001 | −180.4 | 0.0003 | 250 |
|    | Compound CF | −30.9 | N.S. | −79.9 | 0.1592 | 250 |
| 24 | Metformin | −242.6 | <0.0001 | −212.1 | 0.0002 | 250 |
|    | Compound CC | 0.8 | N.S. | −47.9 | N.S. | 250 |
|    | Compound CG | −3.3 | N.S. | −69.7 | N.S. | 250 |
|    | Compound CH | 5.9 | N.S. | −38.6 | N.S. | 250 |
|    | Compound CI | 43.6 | N.S. | −19.3 | N.S. | 250 |
| 25 | Metformin | −72.9 | 0.0036 | −128.4 | <0.0001 | 250 |
|    | Compound CR | −3.8 | N.S. | −55.6 | 0.0154 | 250 |
| 26 | Metformin | −201.3 | 0.0176 | −193.0 | 0.0003 | 250 |
|    | Compound CP | −156.8[2] | N.S. | −111.2[2] | 0.0861 | 250 |
|    | Compound CS | −95.0[2] | N.S. | −64.9[2] | N.S. | 250 |

TABLE 1a-continued

Effects of Aniline derivatives on Blood Glucose in Diabetic db/db Mice

| Exp. No. | Treatment | Change in Glucose (mg/dL) 3 h | P Value* | Change in Glucose (mg/dL) 27 h | P Value* | Dose (mg/kg) |
|---|---|---|---|---|---|---|
| 27 | Metformin | −140.2 | <0.001 | −122.2 | 0.0036 | 250 |
|  | Compound CP | −40.6 | 0.1027 | −23.2 | N.S. | 250 |
|  | Compound CN | −85.7 | 0.0010 | −104.6 | 0.0112 | 250 |

*Statistical significance evaluated using analysis of variance and Fisher's post-hoc test.
N.T. - Not tested
N.S. - not significant at p<0.05 level
[1]Vehicle control increased substantially vs. baseline value at this time point
[2]Vehicle control decreased substantially vs. baseline value at this time point
†¼ Animals died In the described experiments, body weights were not adversely affected by any of the test compounds (Table 2). Food consumption was adversely affected in animals treated with Compound BG and Compound CN.

Although several of the test compounds did not result in a substantial reduction in plasma glucose in the 3–27 h time period under the conditions of the in vivo experiments, as described below Section 7.2, Compounds AC, AD, BN, BF, AV, AH, AI, AJ, AZ, BG, BK, AO, and BM did result in increased glucose transport in an in vitro, art-recognized system. This in vitro system represents an important mode of action for glucose utilization and disposal in mammals.

Additionally, it would be recognized by those skilled in the art that under the conditions in which Compounds AC, AD, BN, BF, AV, AH, AI, AJ, AZ, BG, BK, AO, BQ, and BM were evaluated in vivo, i.e., 1–2 doses, differences in pharmacokinetics, absorption, or pharmacology could explain the lower activity of these compounds compared to the more potently "active" compounds.

TABLE 2

Effects of Aniline derivatives on Body Weights and Food Consumption in Diabetic db/db Mice

| Exp. No. | Treatment | Body weight (g/mouse mean) 0 h | Body weight (g/mouse mean) 24/27 h | Food Intake (g/mouse) 0–24/27 h |
|---|---|---|---|---|
| 1 | Vehicle | 43.0 | 43.8 | 5.4 |
|  | Metformin | 42.4 | 42.9 | 4.9 |
|  | Compound AB | 42.5 | 43.2 | 6.0 |
| 2 | Vehicle | 41.2 | 41.2 | 5.5 |
|  | Metformin | 41.2 | 41.4 | 4.4 |
|  | Compound AC | 42.6 | 42.4 | 5.7 |
| 3 | Vehicle | 40.8 | 40.8 | 5.9 |
|  | Metformin | 40.8 | 40.4 | 4.6 |
|  | Compound AD | 41.8 | 41.1 | 5.6 |
|  | Compound AF | 41.0 | 40.8 | 5.3 |
| 4 | Vehicle | 38.3 | 38.8 | 5.4 |
|  | Metformin | 39.2 | 39.5 | 4.9 |
|  | Compound AE | 38.3 | 40.0 | 4.3 |
|  | Compound BN | N.T. | N.T. | N.T. |
| 5 | Vehicle | 40.6 | 40.4 | 6.4 |
|  | Metformin | 41.7 | 41.3 | 6.1 |
|  | Compound BF | 42.2 | 41.9 | 6.1 |
|  | Compound AV | 41.9 | 41.3 | 5.1 |
| 6 | Vehicle | 38.4 | 38.3 | 4.9 |
|  | Metformin | 39.2 | 38.8 | 4.1 |
|  | Compound AG | 41.4 | 41.5 | 5.2 |
| 7 | Vehicle | 40.7 | 41.1 | 6.2 |
|  | Metformin | 41.3 | 41.1 | 5.0 |

TABLE 2-continued

Effects of Aniline derivatives on Body Weights and Food Consumption in Diabetic db/db Mice

| Exp. No. | Treatment | Body weight (g/mouse mean) 0 h | Body weight (g/mouse mean) 24/27 h | Food Intake (g/mouse) 0–24/27 h |
|---|---|---|---|---|
|  | Compound AH | 40.0 | 40.2 | 6.2 |
|  | Compound AI | 41.5 | 41.5 | 6.1 |
| 8 | Vehicle | 42.6 | 43.2 | 6.3 |
|  | Metformin | 42.5 | 42.9 | 5.7 |
|  | Compound AJ | 43.5 | 43.8 | 6.2 |
| 9 | Vehicle | 40.1 | 40.3 | 3.9 |
|  | Metformin | 38.5 | 38.6 | 3.8 |
|  | Compound AK | 39.0 | 39.4 | 3.8 |
|  | Compound BE | 39.9 | 40.2 | 4.4 |
|  | Compound AP | 39.4 | 40.2 | 4.6 |
| 10 | Vehicle | 40.8 | 41.1 | 5.9 |
|  | Metformin | 40.9 | 40.9 | 5.9 |
|  | Compound AU | 40.2 | 40.3 | 5.3 |
|  | Compound AW | 41.3 | 41.0 | 5.5 |
| 11 | Vehicle | 41.1 | 41.2 | 5.4 |
|  | Metformin | 39.8 | 40.0 | 6.3 |
|  | Compound AZ | 39.1 | 39.1 | 4.8 |
|  | Compound BG | 39.7 | 39.5 | 5.5 |
| 12 | Vehicle | 40.5 | 40.5 | 6.4 |
|  | Metformin | 40.7 | 40.3 | 4.6 |
|  | Compound AL | 40.7 | 40.8 | 8.0 |
|  | Compound BB | 41.4 | 41.7 | 2.9 |
| 13 | Vehicle | 38.5 | 38.8 | 5.3 |
|  | Metformin | 39.3 | 39.1 | 5.2 |
|  | Compound BK | 40.0 | 40.1 | 4.7 |
| 14 | Vehicle | 40.4 | 40.1 | 6.4 |
|  | Metformin | 40.4 | 40.4 | 4.6 |
|  | Compound AN | 41.0 | 41.2 | 6.0 |
| 15 | Vehicle | 39.5 | 40.0 | 5.2 |
|  | Metformin | 40.1 | 40.3 | 5.2 |
|  | Compound BL | 39.3 | 39.6 | 5.0 |
| 16 | Vehicle | 39.5 | 39.5 | 7.1 |
|  | Metformin | 39.2 | 38.8 | 5.4 |
|  | Compound AO | 39.6 | 40.0 | 7.3 |
|  | Compound BQ | 40.1 | 40.2 | 7.0 |
| 17 | Vehicle | 36.4 | 38.2 | 6.6 |
|  | Metformin | 37.5 | 39.3 | 6.3 |
|  | Compound BM | 37.3 | 39.6 | 7.2 |
| 18 | Vehicle | 40.1 | 40.1 | 5.4 |
|  | Metformin | 41.1 | 41.0 | 5.8 |
|  | Compound BR | 38.3 | * | * |
| 19 | Vehicle | 41.1 | 40.8 | 6.2 |
|  | Metformin | 41.9 | 41.8 | 4.6 |
|  | Compound BY | 39.7 | 39.8 | 5.9 |
|  | Compound CA | 40.7 | 40.6 | 4.9 |
|  | Compound CB | 40.4 | 40.3 | 6.0 |
|  | Compound BZ | 41.5 | 41.7 | 6.6 |

TABLE 2-continued

Effects of Aniline derivatives on Body Weights and Food Consumption in Diabetic db/db Mice

| Exp. No. | Treatment | Body weight (g/mouse mean) 0 h | Body weight (g/mouse mean) 24/27 h | Food Intake (g/mouse) 0–24/27 h |
|---|---|---|---|---|
| 20 | Vehicle | 39.9 | 39.5 | 5.5 |
|  | Metformin | 39.5 | 39.1 | 4.2 |
|  | Compound CC | 39.7 | 39.6 | 4.4 |
| 21 | Vehicle | 40.2 | 40.0 | 5.1 |
|  | Metformin | 40.2 | 39.9 | 4.4 |
|  | Compound CB | 41.1 | 40.9 | 6.9 |
|  | Compound CE | 40.5 | 40.5 | 5.6 |
| 22 | Vehicle | 39.4 | 39.1 | 5.9 |
|  | Metformin | 38.5 | 38.7 | 3.8 |
|  | Compound CJ | 38.8 | 39.1 | 5.1 |
|  | Compound CK | 39.5 | 39.7 | 5.0 |
|  | Compound CL | 39.2 | 40.2 | 5.0 |
|  | Compound CM | 38.4 | 38.9 | 5.5 |
| 23 | Vehicle | 38.9 | 38.5 | 4.4 |
|  | Metformin | 39.1 | 38.8 | 4.8 |
|  | Compound CF | 38.8 | 39.0 | 4.9 |
| 24 | Vehicle | 38.9 | 39.0 | 5.8 |
|  | Metformin | 38.3 | 38.3 | 4.7 |
|  | Compound CC | 39.5 | 39.2 | 5.4 |
|  | Compound CG | 39.9 | 39.7 | 5.5 |
|  | Compound CH | 39.0 | 39.2 | 6.3 |
|  | Compound CI | 39.2 | 39.1 | 6.0 |
| 25 | Vehicle | 38.4 | 38.6 | 5.6 |
|  | Metformin | 37.4 | 37.4 | 4.8 |
|  | Compound CR | 39.3 | 39.5 | 5.2 |
| 26 | Vehicle | 37.1 | 37.7 | 5.3 |
|  | Metformin | 37.8 | 38.0 | 4.4 |
|  | Compound CP | 37.1 | 37.2 | 4.6 |
|  | Compound CS | 37.8 | 37.8 | 4.8 |
| 27 | Vehicle | 38.8 | 38.5 | 5.8 |
|  | Metformin | 39.7 | 39.8 | 5.4 |
|  | Compound CP | 39.2 | 39.5 | 5.6 |
|  | Compound CN | 39.4 | 39.1 | 0.8 |

*⅞ Animals died

7.2 IN VITRO ACTIVITY OF THE ANILINE DERIVATIVES

The following examples illustrate the ability of the aniline derivatives described herein to directly stimulate glucose transport in 3T3-L1 adipocytes, an art recognized in vitro system that represents an important mode of action for glucose utilization and disposal in mammals (Frost and Lane, J. Biol. Chem. 1985, 260, 2646–2653). Metformin, a drug that enhances glucose disposal and one that is currently used to treat NIDDM, exhibits significant stimulatory activity in this model system.

7.2.1 PROTOCOLS

The following protocols were used to evaluate the aniline derivatives in vitro.

Murine 3T3-L1 preadipocytes (American Type Culture Collection CL 173) were maintained in Dulbecco's modified Eagles medium (DMEM) containing 10% (v/v) supplemented calf serum, antibiotics, and 25 mM glucose. Cells were seeded in 24-well cluster plates (10,000 cells/well), grown to confluence (typically 5 days), and induced to differentiate 2 days post-confluence (day 0) according to the standard protocol of Frost and Lane (Frost, S. and Lane, M. D. *J. Biol. Chem.* 1985, 260, 2646–2652). Following differentiation, adipocytes were maintained in DMEM containing 10% fetal bovine serum, and provided with fresh medium every 2–3 days. Adipocytes employed in this study were used on days 7–10 post-differentiation. On the day before the experiment, adipocytes were washed with phosphate-buffered saline and switched to serum-free DMEM medium.

Concentrated stock solutions of the aniline derivatives were freshly prepared in dimethyl sulfoxide (DMSO) and diluted into culture medium. The final concentration of DMSO was 0.5% (v/v) which was also included in basal and insulin controls. Metformin was dissolved directly into culture medium and further diluted into the same medium. Adipocytes were treated (in triplicate) for 18 h with a test compound, i.e., an aniline derivative (at 3, 10, and 30 μM final concentrations) or metformin.

7.2.1.1 METHOD A

CELL CULTURE AND 2-DEOXY-D-GLUCOSE UPTAKE IN DIFFERENTIATED 3T3-L1 ADIPOCYTES WITHOUT EXOGENOUSLY ADDED INSULIN

The in vitro assay according to Method A was conducted as follows: After overnight (18 h) treatment, the adipocyte cell monolayers were washed, and the medium was switched to Krebs-Ringer Hepes (KRH) buffer. The compounds were tested at 3, 10 and 30 μm (triplicate incubations). Compound treated adipocytes were given the insulin vehicle KRH/1% Bovine Serum Albumin (KRH/1% BSA) (containing no insulin). The final concentration of KRH/1% BSA was 4%, which was also included in the basal control.

For the insulin control adipocytes, a concentrated porcine insulin stock was freshly diluted into KRH/1% BSA. The final concentration of insulin in the insulin control was 0.5 nM in 4% KRH/1% BSA. The plates were then incubated for 30 min at 37° C.

To assess the effects of the compounds on glucose transport, 2-deoxy-D-glucose uptake (a non-metabolizable analogue of glucose) was measured in the absence of insulin stimulation. Glucose transport assays were initiated by the addition of 2-deoxy-D-($^3$H)glucose (0.5 Mci/mL; 100 mM final concentrations) to each well followed by incubation for 10 min at 22° C. Assays were terminated by aspirating the media and rapidly washing the monolayer two times with ice-cold phosphate-buffered saline solution. Cell monolayers were solubilized in 0.1N NaOH, transferred to scintillation vials, and radioactivity was determined by liquid scintillation counting. All data were corrected for non-specific hexose uptake determined in parallel samples treated for 5 min with 200 mM cytochalasin B.

The following compounds were tested in the in vitro assay of Method A:

2-(2-(((2-fluorophenyl)amino)acetyl)amino)benzoic acid (Compound AB);

2-(2-((phenylamino)acetyl)amino)-5-fluorobenzoic acid (Compound AQ);

2-(2-((phenylthio)acetyl)amino)benzoic acid (Compound BJ);

2-(2-((phenyloxy)acetyl)amino)benzoic acid (Compound BI)

2-(2-((phenylamino)acetyl)amino)-6-chlorobenzoic acid (Compound BC);

2-(2-((phenylamino)acetyl)amino)-5-methoxybenzoic acid (Compound BD);

2-(2-((phenylamino)acetyl)amino)-5-chlorobenzoic acid (Compound BA);

2-((2-bromoacetyl)amino)benzoic acid (Compound AA);

2-(2-((phenylamino)acetyl)amino)-3-chlorobenzoic acid (Compound AX);

2-(2-(((3-fluorophenyl)amino)acetyl)amino)benzoic acid (Compound AC);

2-(2-(((4-fluorephenyl)amino)acetyl)amino)benzoic acid (Compound AD);

2-(2-(((4-(phenyl)phenyl)amino)acetyl)amino)benzoic acid (Compound AE);

2-(2-(((4-methoxyphenyl)amino)acetyl)amino)benzoic acid (Compound AF);

2-(2-((phenylamino)acetyl)amino)-5-bromobenzoic acid (Compound BF);

2-(2-(((4-fluorephenyl)amino)acetyl)amino)-5-fluorobenzoic acid (Compound AR);

2-(2-(((4-methylphenyl)amino)acetyl)amino)-5-fluorobenzoic acid (Compound AS);

2-(2-(((4-chlorophenyl)amino)acetyl)amino)-5-fluorobenzoic acid (Compound AT);

2-(2-((phenylamino)acetyl)amino)-6-fluorobenzoic acid (Compound AV);

2-(2-(((4-(trifluoromethyl)phenyl)amino)acetyl)amino) benzoic acid (Compound AG);

2-(2-(((2,3-dimethylphenyl)amino)acetyl)amino)benzoic acid (Compound AH);

2-(2-(((2,3-dichlorophenyl)amino)acetyl)amino)benzoic acid (Compound AI);

2-(2-(((2-methoxyphenyl)amino)acetyl)amino)benzoic acid (Compound AJ);

2-(2-((phenylamino)acetyl)amino)benzoic acid (Compound AK);

2-(2-(((2-(trifluoromethyl)phenyl)amino)acetyl)amino) benzoic acid (Compound AL);

2-(2-(((2-fluorophenyl)amino)acetyl)amino)-5-fluorobenzoic acid (Compound AU);

2-(2-(((2-fluorophenyl)amino)acetyl)amino)-6-fluorobenzoic acid (Compound AW);

2-(2-(((2-fluorophenyl)amino)acetyl)amino)-4-chlorobenzoic acid (Compound AZ);

2-(2-(((2-fluorophenyl)amino)acetyl)amino)-5-hydroxybenzoic acid (Compound BH);

2-(2-(((2-fluorophenyl)amino)acetyl)amino)-5-bromobenzoic acid (Compound BG);

2-(2-(((2-fluorophenyl)amino)acetyl)amino)-5-chlorobenzoic acid (Compound BB);

2-(2-((phenylamino)acetyl)amino)-4-chlorobenzoic acid (Compound AY);

2-((2-fluorophenyl)amino)acetic acid (Compound BK);

2-(2-(((2-fluorophenyl)amino)acetyl)amino)-5-methoxybenzoic acid (Compound BE);

4-(2-(((2-fluorophenyl)amino)acetyl)amino)benzoic acid (Compound AP);

2-(2-(((2-fluorophenyl)oxy)acetyl)amino)benzoic acid (Compound AM);

2-(2-(((4-(trifluoromethyl)phenyl)thio)acetyl)amino) benzoic acid (Compound AN);

methyl 2-(2-(((2-fluorophenyl)amino)acetyl)amino) benzoate (Compound BL);

1,2-bis((2-carboxyphenyl)amino)ethane (Compound BM);

4-(2-(((2-fluorophenyl)amino)acetyl)amino) phenylacetic acid (Compound BO);

1-((2-carboxyphenyl)amino)-2-((2-fluorophenyl)amino) ethane (Compound BN);

2-(2-(((2-fluorophenyl)thio)acetyl)amino)benzoic acid (Compound AO);

4-(2-(((2-fluorophenyl)amino)acetyl)amino)benzyl tetrazole (Compound BQ);

4-(2-(((2-fluorophenyl)amino)acetyl)amino)benzyl cyanide (Compound BP);

3-(2-(((2-fluorophenyl)amino)acetyl)amino)pyridine (Compound BR).

7.2.1.2 METHOD B:

CELL CULTURE AND 2-DEOXY-D-GLUCOSE UPTAKE IN DIFFERENTIATED 3T3-L1 ADIPOCYTES WITH EXOGENOUSLY ADDED INSULIN

The in vitro assay according to Method B was conducted as follows: After overnight (18 h) treatment, the cell monolayers were washed, and the medium was switched to Krebs-Ringer Hepes (KRH) buffer. The compounds were tested at 3, 10 and 30 µM (triplicate incubations). Basal control adipocytes were given the insulin vehicle KRH/1% bovine serum albumin (KRH/1% BSA). The final concentration of KRH/1% BSA was 4%. A concentrated porcine insulin stock was freshly diluted into KRH/1% BSA and given to the compound treated adipocytes and to the insulin control adipocytes. The final concentration of insulin was 0.5 nM in 4% KRH/1% bsa. The plates were then incubated for 30 min at 37° C.

To assess the effects of the compounds on glucose transport, 2-deoxy-d-glucose uptake (a non-metabolizable analogue of glucose) was measured in the presence of insulin stimulation. Glucose transport assays were initiated by the addition of 2-deoxy-d-($^3$H)glucose (0.5 Mci/mL; 100 mM final concentrations) to each well followed by incubation for 10 min at 22° C. Assays were terminated by aspirating the media and rapidly washing the monolayer two times with ice-cold phosphate-buffered saline solution. Cell monolayers were solubilized in 0.1N NaOH, transferred to scintillation vials, and radioactivity was determined by liquid scintillation counting. All data were corrected for non-specific hexose uptake determined in parallel samples treated for 5 minutes with 200 mM cytochalasin B.

The following compounds were tested in the in vitro assay of Method B:

2-(2-(((2-fluorophenyl)amino)acetyl)amino)benzoic acid (Compound AB);

2-(2-((phenylamino)acetyl)amino)-5-fluorobenzoic acid (Compound AQ);

2-(2-((phenylthio)acetyl)amino)benzoic acid (Compound BJ);

2-(2-((phenylamino)acetyl)amino)-6-chlorobenzoic acid (Compound BC);

2-(2-((phenylamino)acetyl)amino)-5-methoxybenzoic acid (Compound BD);

2-(2-((phenylamino)acetyl)amino)-5-chlorobenzoic acid (Compound BA);

2-(2-((phenylamino)acetyl)amino)-3-chlorobenzoic acid (Compound AX);

2-(2-(((3-fluorophenyl)amino)acetyl)amino)benzoic acid (Compound AC);

2-(2-(((4-fluorophenyl)amino)acetyl)amino)benzoic acid (Compound AD);

2-(2-(((4-(phenyl)phenyl)amino)acetyl)amino)benzoic acid (Compound AE);

5-(2-(((4-methoxyphenyl)amino)acetyl)amino)benzoic acid (Compound AF);

2-(2-((phenylamino)acetyl)amino)-5-bromobenzoic acid (Compound BF);

2-(2-(((4-(trifluoromethyl)phenyl)amino)acetyl)amino) benzoic acid (Compound AG);

2-(2-(((2,3-dichlorophenyl)amino)acetyl)amino)benzoic acid (Compound AI);

2-(2-((phenylamino)acetyl)amino)benzoic acid (Compound AK);

2-(2-(((2-(trifluoromethyl)phenyl)amino)acetyl)amino) benzoic acid (Compound AL);

2-(2-(((2-fluorophenyl)amino)acetyl)amino)-5-fluorobenzoic acid (Compound AU);

2-(2-(((2-fluorophenyl)amino)acetyl)amino)-6-fluorobenzoic acid (Compound AW);

2-(2-(((2-fluorophenyl)amino)acetyl)amino)-4-chlorobenzoic acid (Compound AZ);

2-(2-(((2-fluorophenyl)amino)acetyl)amino)-5-hydroxybenzoic acid (Compound BH);

2-(2-(((2-fluorophenyl)amino)acetyl)amino)-5-chlorobenzoic acid (Compound BB);

2-(2-((phenylamino)acetyl)amino)-4-chlorobenzoic acid (Compound AY);

2-(2-(((2-fluorophenyl)amino)acetyl)amino)-5-methoxybenzoic acid (Compound BE);

4-(2-(((2-fluorophenyl)amino)acetyl)amino)benzoic acid (Compound AP);

2-(2-(((2-fluorophenyl)oxy)acetyl)amino)benzoic acid (Compound AM);

2-(2-(((4-(trifluoromethyl)phenyl)thio)acetyl)amino) benzoic acid (Compound AN);

methyl 2-(2-(((2-fluorophenyl)amino)acetyl)amino) benzoate (Compound BL);

1,2-bis((2-carboxyphenyl)amino)ethane (Compound BM);

4-(2-(((2-fluorophenyl)amino)acetyl)amino)phenylacetic acid (Compound BO);

1-((2-carboxyphenyl)amino)-2-((2-fluorophenyl)amino) ethane (Compound BN);

2-(2-(((2-fluorophenyl)thio)acetyl)amino)benzoic acid (Compound AO);

4-(2-(((2-fluorophenyl)amino)acetyl)amino)benzyl tetrazole (Compound BQ);

4-(2-(((2-fluorophenyl)amino)acetyl)amino)benzyl cyanide (Compound BP).

7.2.2 RESULTS USING METHOD A

The ability of the aniline derivatives to significantly stimulate glucose transport in 3T3-L1 adipocytes in the absence of insulin (Method A) is shown in Table 3. The magnitude of stimulation ranged from approximately 110% of basal to approximately 160%. Under these experimental conditions, 3 mM metformin (the maximally effective concentration) stimulates glucose transport by approximately 350%. As would be recognized by those skilled in the art, these data indicate that the aniline derivatives listed in Table 3 directly stimulate glucose transport in vitro, an effect that is consistent the enhancement of glucose disposal and the ability to lower blood glucose in vivo. This results demonstrate that the compounds "active" in this assay, are useful for treating Type I and Type II diabetes (i.e., insulin dependent diabetes mellitus and non-insulin dependent diabetes mellitus).

TABLE 3

Stimulatory effects of aniline derivatives on 2-deoxy-d-glucose uptake in 3T3-L1 adipocytes in the absence of insulin

| Compound Code | Concentration (μM) | Stimluatory Activity (% Basal) | (p) value |
| --- | --- | --- | --- |
| Compound AB | 3 | 128 | p < 0.03 |
| Compound BD | 3 | 136 | p < 0.04 |
| Compound BA | 30 | 158 | p < 0.007 |
| Compound AA | 10 | 130 | p < 0.01 |
| Compound AC | 10 | 148 | p < 0.03 |
| Compound AD | 3 | 135 | p < 0.03 |
| Compound AE | 10 | 129 | p < 0.03 |
| Compound AF | 3 | 121 | p < 0.04 |
| Compound BF | 30 | 110 | p < 0.02 |
| Compound AV | 3 | 108 | p < 0.04 |
| Compound AH | 30 | 142 | p < 0.0001 |
| Compound AI | 30 | 169 | p < 0.0003 |
| Compound AJ | 3 | 120 | p < 0.04 |
| Compound AU | 10 | 118 | p < 0.0004 |
| Compound AZ | 10 | 117 | p < 0.04 |
| Compound BG | 3 | 164 | p < 0.009 |
| Compound BK | 10 | 123 | p < 0.05 |
| Compound BN | 30 | 144 | p < 0.03 |
| Compound BJ | 30 | 145 | p < 0.009 |

Values shown for stimulatory activity are expressed as a percent of basal glucose transport (typically 0.15 nmoles 2-deoxyglucose/10 min/well), and represent the maximum stimulation observed along with the corresponding concentration). All compounds listed above demonstrated significant stimulation of glucose transport P<0.05 or better) as judged using a student's t-test (one-tailed, independent).

In addition to the compounds listed in Table 3, the following aniline derivatives did not demonstrate statistically significant glucose transport stimulatory activity in the absence of insulin (Method A): Compound AQ, Compound BC, Compound AX, Compound AR, Compound AS, Compound AT, Compound AG, Compound AK, Compound AL, Compound AW, Compound BH, Compound BB, Compound AY, Compound BE, Compound AP, Compound AM, Compound AN, Compound BL, Compound BM, Compound BO, Compound AO, Compound BP, Compound BQ and Compound BR.

7.2.3 RESULTS USING METHOD B

The ability of the aniline derivatives to significantly stimulate glucose transport in 3T3-L1 adipocytes in the presence of insulin (Method B) is shown in Table 4. The magnitude of stimulation ranged from approximately 120% of insulin control to approximately 170%. Under these experimental conditions, 3 mM metformin (the maximally effective concentration) stimulates glucose transport by approximately 150%. As would be recognized by those skilled in the art, these data indicate that the aniline derivatives listed in Table 4 directly stimulate glucose transport in the presence of insulin in vitro, an effect that is consistent the enhancement of glucose disposal and the ability to lower blood glucose in vivo. These results demonstrate that the compounds "active" in this assay (those listed in Table 4) are useful for treating Type II diabetes.

TABLE 4

Stimulatory effects of aniline derivatives on 2-deoxy-D-glucose uptake in 3t3-11 adipocytes in the presence of insulin

| Compound Code | Concentration (µM) | Stimulatory Activity (% Basal) | (p) value |
|---|---|---|---|
| Compound AB | 30 | 126 | p < 0.006 |
| Compound BJ | 3 | 146 | p < 0.0045 |
| Compound BA | 30 | 120 | p < 0.008 |
| Compound AG | 3 | 116 | p < 0.04 |
| Compound AI | 10 | 140 | p < 0.003 |
| Compound AK | 30 | 134 | p < 0.01 |
| Compound AL | 30 | 134 | p < 0.04 |
| Compound BM | 30 | 134 | p < 0.03 |
| Compound BN | 3 | 133 | p < 0.03 |
| Compound AO | 3 | 126 | p < 0.04 |
| Compound AR | 30 | 125 | p < 0.01 |
| Compound BG | 30 | 125 | p < 0.02 |

Values shown for stimulatory activity are expressed as a percent of insulin control glucose transport (typically 0.3 nmoles 2-deoxyglucose/10 min/well), and represent the maximum stimulation observed along with the corresponding concentration). All compounds listed above demonstrated significant stimulation of glucose transport (P<0.05 or better) as judged using a Student's t-test (one-tailed, independent).

In addition to the compounds listed in Table 4, the following aniline derivatives did not demonstrate statistically significant glucose transport stimulatory activity in the presence of insulin (Method B): Compound AQ, Compound BC, Compound BD, Compound AX, Compound AC, Compound AD, Compound AE, Compound AF, Compound BF, Compound AU, Compound AW, Compound AZ, Compound BH, Compound BB, Compound AY, Compound BK, Compound BE, Compound AP, Compound AM, Compound AN, Compound BL, Compound BO, Compound BQ, Compound BP, Compound BR.

The present invention is not to be limited in scope by the specific embodiments disclosed in the examples which are intended as illustrations of a number of aspects of the invention and any embodiments which are functionally equivalent are within the scope of this invention. Indeed, various modifications of the invention in addition to those shown and described herein will become apparent to those skilled in the art and are intended to fall within appended claims.

A number of references have been cited, the entire disclosures of which are incorporated herein by reference.

What is claimed is:

1. A compound selected from the group consisting of:

2-(2-(((2-fluorophenyl)amino)acetyl)amine)benzoic Acid;

2-(2-(((4-(Phenyl)phenyl)amine)acetyl)amine)benzoic Acid;

2-(2-(((4-(Trifluoromethyl)phenyl)amino)acetyl)amine) benzoic Acid;

2-(2-(((2-Fluorophenyl)amino)acetyl)amino)-5-methoxybenzoic Acid;

4-(2-(((2-Fluorophenyl)amino)acetyl)amino)benzoic Acid;

2-(2-(((2-Fluorophenyl)amino)acetyl)amino)-5-fluorobenzoic Acid;

2-(2-(((2-Fluorophenyl)amino)acetyl)amine)-6-fluorobenzoic Acid;

2-(2-(((2-(Trifluoromethyl)phenyl)amino)acetyl)amino) benzoic Acid;

2-(2-(((2-Fluorophenyl)amino)acetyl)amino)-5-chlorobenzoic Acid;

2-(2-((4-(Trifluoromethyl)phenyl)thio)acetyl)amino) benzoic Acid;

Methyl 2-(2-(((2-Fluorophenyl)amino)acetyl)amino) benzoate;

2-(2-((Phenylamino)acetyl)amino)-5-methoxybenzoic Acid;

2-(2-((phenylamino)acetyl)amino)-5-chlorobenzoic Acid;

2-(2-(((3-fluorophenyl)amino)acetyl)amino)benzoic Acid;

2-(2-((Phenylamino)acetyl)amino)-5-bromobenzoic Acid;

2-(2-((Phenylamino)acetyl)amino)-6-fluorobenzoic Acid;

2-(2-((2,3-Dimethylphenyl)amino)acetyl)amino)benzoic Acid;

2-(2-(((2,3-Dichlorophenyl)amino)acetyl)amino)benzoic Acid;

2-(2-(((2-Methoxyphenyl)amino)acetyl)amino)benzoic Acid;

2-(2-(((2-Fluorophenyl)amino)acetyl)amino)-4-chlorobenzoic Acid;

2-(2-(((2-Fluorophenyl)amino)acetyl)amino)-5-bromobenzoic Acid;

2-((2-Carboxyphenyl)amino)-2-((2-fluorophenyl)amino) ethane;

2-(2-(((2-fluorophenyl)thio)acetyl)amino)benzoic Acid;

2-(2-(((4-Fluorophenyl)amino)acetyl)amino)-5-fluorobenzoic Acid; 2-((Fluorophenyl)amino)acetyl) amine benzene; and 4-((2-((Fluorophenyl)amino) acetyl)amino)phenol; and pharmaceutically acceptable salts thereof.

2. A method for reducing the blood glucose of a mammal, comprising administering to said mammal an antihyperglycemically effective amount of a composition comprising a compound selected from the group consisting of:

2-(2-(((2-fluorophenyl)amino)acetyl)amino)benzoic acid;

2-(2-(((4-methoxyphenyl)amino)acetyl)amino)benzoic acid;

2-(2-(((4-(phenyl)phenyl)amino)acetyl)amino)benzoic acid;

2-(2-(((4-(trifluoromethyl)phenyl)amino)acetyl)amino) benzoic acid;

2-(2-((phenylamino)acetyl)amino)benzoic acid;

2-(2-(((2-fluorophenyl)amino)acetyl)amino)-5-methoxybenzoic acid;

4-(2-(((2-fluorophenyl)amino)acetyl)amino)benzoic acid;

2-(2-((2-fluorophenyl)amino)acetyl)amino)-5-fluorobenzoic acid;

2(2-(((2-fluorophenyl)amino)acetyl)amino)-6-fluorobenzoic acid;

2-(2-(((2-(trifluoromethyl)phenyl)amino)acetyl)amino) benzoic acid;

2-(2-((2-fluorophenyl)amino)acetyl)amino)-5-chlorobenzoic acid;

2-(2-(((4-(trifluoromethyl)phenyl)thio)acetyl)amino) benzoic acid;

methyl 2-(2-(((2-fluorophenyl)amino)acetyl)amino) benzoate;

Methyl 2-(((2-(4-(trifluoromethyl)phenyl)amino)acetyl) amino)benzoate;

Methyl 4-(((2-(4-(Trifluoromethyl)phenyl)amino)acetyl)amino)benzoate;

4-(((2-(4-(Trifluoromethyl)phenyl)amino)acetyl)amino)benzoic Acid;

4-(((2-(2-(Trifluoromethyl)phenyl)amino)acetyl)amino)benzoic Acid;

4-((2-((2-Fluorophenyl)amino)acetyl)amino)-1-butoxybenzene;

2-((2-(Fluorophenyl)amino)acetyl)aminobenzene; and 4-((2-((2-Fluorophenyl)amino)acetyl)amino)phenol, and pharmaceutically acceptable salts thereof.

3. A method for reducing the blood glucose of a mammal, comprising administering to said mammal an antihyperglycemically effective amount of a composition comprising a compound selected from the group consisting of:

2-(2-((Phenylamino)acetyl)amino)-5-methoxybenzoic Acid;

2-(2-((phenylamino)acetyl)amino)-5-chlorobenzoic acid;

2-(2-(((3-fluorophenyl)amino)acetyl)amino)benzoic acid;

2-(2-(((4-Fluorophenyl)amino)acetyl)amino)benzoic Acid;

2-(2-((Phenylamino)acetyl)amino)-5-bromobenzoic Acid;

2-(2-((Phenylamino)acetyl)amino)-6-fluorobenzoic Acid;

2-(2-(((2,3-dimethylphenyl)amino)acetyl)amino)benzoic acid;

2-(2-(((2,3-dichlorophenyl)amino)acetyl)amino)benzoic acid;

2-(2-(((2-Methoxyphenyl)amino)acetyl)amino)benzoic Acid;

2-(2-((2-fluorophenyl)amino)acetyl)amino)-4-chlorobenzoic acid;

2-(2-(((2-fluorophenyl)amino)acetyl)amino)-5-bromobenzoic acid;

1-(2-carboxyphenyl)amino)-2-((2-fluorophenyl)amino)ethane;

2-((2-(Phenylthio)acetyl)amino)benzoic Acid;

1,2-Bis((2-Carboxyphenyl)amino)ethane;

2-(2-(((2-fluorophenyl)thio)acetyl)amino)benzoic acid; and 2-(2-(((4-Fluorophenyl)amino)acetyl)amino)-5-fluorobenzoic Acid, and pharmaceutically acceptable salts thereof.

4. A pharmaceutical composition useful for lowering the blood glucose level of a mammal, said composition comprising an antihyperglycemically effective amount of a compound of claim 1.

* * * * *